US011377484B2

(12) United States Patent
Remaut et al.

(10) Patent No.: US 11,377,484 B2
(45) Date of Patent: Jul. 5, 2022

(54) COMPOUNDS TO INHIBIT BACTERIAL S-LAYER PROTEIN ASSEMBLY

(71) Applicants: VIB VZW, Ghent (BE); VRIJE UNIVERSITEIT BRUSSEL, Brussels (BE)

(72) Inventors: Han Remaut, Roosbeek (BE); Antonella Fioravanti, Brussels (BE)

(73) Assignees: VIB VZW, Ghent (BE); Vrij Universiteit Brussel, Brussels (BE)

( * ) Notice: Subject to any disclaimer, the term of this patent is extended or adjusted under 35 U.S.C. 154(b) by 0 days.

(21) Appl. No.: 16/651,713

(22) PCT Filed: Oct. 2, 2018

(86) PCT No.: PCT/EP2018/076727
§ 371 (c)(1),
(2) Date: Mar. 27, 2020

(87) PCT Pub. No.: WO2019/068677
PCT Pub. Date: Apr. 11, 2019

(65) Prior Publication Data

US 2020/0255501 A1 Aug. 13, 2020

(30) Foreign Application Priority Data

Oct. 2, 2017 (GB) ..................................... 1716059
Apr. 25, 2018 (EP) .................................... 18169187

(51) Int. Cl.
*C07K 16/12* (2006.01)
*A61K 39/00* (2006.01)
*A61P 31/04* (2006.01)

(52) U.S. Cl.
CPC .......... *C07K 16/1278* (2013.01); *A61P 31/04* (2018.01); *A61K 2039/505* (2013.01); *C07K 2317/565* (2013.01); *C07K 2317/569* (2013.01)

(58) Field of Classification Search
None
See application file for complete search history.

(56) References Cited

U.S. PATENT DOCUMENTS 6,828,110 B2 * 12/2004 Lee ........................ C07K 14/32 424/246.1
7,329,738 B1 * 2/2008 Lee .................. G01N 33/56911 424/234.1
7,374,888 B2 * 5/2008 Valkirs ............... C07K 16/1278 435/69.7
7,393,647 B2 * 7/2008 Valkirs ............... G01N 33/6854 435/69.7
10,054,598 B2 * 8/2018 Steyaert .................. A61P 35/00
10,463,711 B2 * 11/2019 Hamill .................... A61K 38/10
10,583,186 B2 * 3/2020 Vedantam .............. A61K 39/08
2004/0072241 A1 * 4/2004 Valkirs ............. G01N 33/56911 435/7.1
2005/0233408 A1 * 10/2005 Pouwels .............. C07K 14/335 435/34
2008/0012474 A1 1/2008 Sung et al.
2008/0124747 A1 * 5/2008 Valkirs ................... C07K 17/00 435/7.32
2010/0172938 A1 * 7/2010 Pouwels ................. A61P 31/04 424/234.1
2018/0000919 A1 * 1/2018 Vedantam .............. A61K 39/08
2020/0237888 A1 * 7/2020 Vedantam ............... A61P 31/04
2020/0239527 A1 * 7/2020 Vedantam .............. A61K 39/09
2020/0255501 A1 * 8/2020 Remaut .............. C07K 16/1282
2020/0306342 A1 * 10/2020 Hamill ..................... A61P 31/18

FOREIGN PATENT DOCUMENTS

CA 3076250 A1 * 4/2019 ............. G01N 33/53
EP 3691684 A1 * 8/2020 ......... C07K 16/1282
WO WO-03055906 A1 * 7/2003 ............. A61P 37/04
WO 2007007086 A2 1/2007
WO WO-2007044607 A2 * 4/2007 .............. A61P 31/04
WO WO-2015048332 A2 * 4/2015 ................ A61P 3/10
WO WO-2016118900 A1 * 7/2016 ............. A61K 39/08
WO WO-2019068677 A1 * 4/2019 ......... C07K 16/1278

OTHER PUBLICATIONS

Baranova et al, Nature, Jul. 5, 2012. 487:119-124 (Year: 2012).*
Chateau et al, Microorganisms. 2020, 8:1864, pp. 25 (Year: 2020).*
Kandalaft et al, Appl. Microbiol. Biotechnol., 2015. 99:8549-8562. published online: May 5, 2015 (Year: 2015).*
Baranove et al, Nature, Jul. 5, 2012 4877:119-124 (Year: 2012).*
Chateau et al. Microorganisms. 2020, 8., 1864, 25 pages. published; Nov. 26, 2020 . . . (Year: 2020).*
Fioravanti et al, Nature Microbiology, Nov. 2019, 4:1805-1814 (Year: 2019).*
Stuknyte etal, Applied and Environmental Microbiology, Jan. 2014, 80/2:694-703. published ahead of print: Nov. 15, 2013. (Year: 2014).*
Kandalaft, Hiba, et al. “Targeting Surface-Layer Proteins with Single-Domain Antibodies: a Potential Therapeutic Approach against Clostridium Difficile—Associated Disease.” Applied Microbiology and Biotechnology, vol. 99, No. 20, 2015, pp. 8549-8562.

(Continued)

*Primary Examiner* — Nita M. Minnifield
(74) *Attorney, Agent, or Firm* — Patent Law Works, LLP

(57) ABSTRACT

The present invention relates to the field of bacterial Surface (S)-layer proteins, in particular to compounds capable of disrupting the bacterial S-Layer, specifically the S-Layer of *Bacillus anthracis*. More particularly, the invention provides for single domain antibodies for diagnosis and treatment of infection caused by pathogens with an S-Layer, in particular of *Bacillus anthracis* infection. The invention relates to S-Layer protein binding agents inhibiting bacterial growth and interrupting S-Layer assembly, useful in the treatment of bacterial infection, more specifically treatment of anthrax disease.

11 Claims, 37 Drawing Sheets

Specification includes a Sequence Listing.

(56) References Cited

OTHER PUBLICATIONS

PCT International Search Report and Written Opinion; Application No. PCT/EP2018/076727, Applicant VIB VZW, International filing date of Oct. 2, 2018, dated Jan. 22, 2019, Authorized Officer Alain Camilleri, 11 pages.

Scheemann, Anette, and Marianne Manchester. "Anti-Toxin Antibodies in Prophylaxis and Treatment of Inhalation Anthrax." Future Microbiology, vol. 4, No. 1, 2009, pp. 35-43.

Walper, Scott A., et al. "Rugged Single Domain Antibody Detection Elements for Bacillus Anthracis Spores and Vegetative Cells (Single Domain Antibodies for Bacillus Anthracis)." PLoS ONE, vol. 7, No. 3, 2012, p. e32801.

* cited by examiner

D1: $II_{221-222}$ --- $Y_{271}SNLAA_{276}$

D2: $A_{316}LQEITVKDENGTEVVSPE_{333}$

*B. Anthracis* 34F2

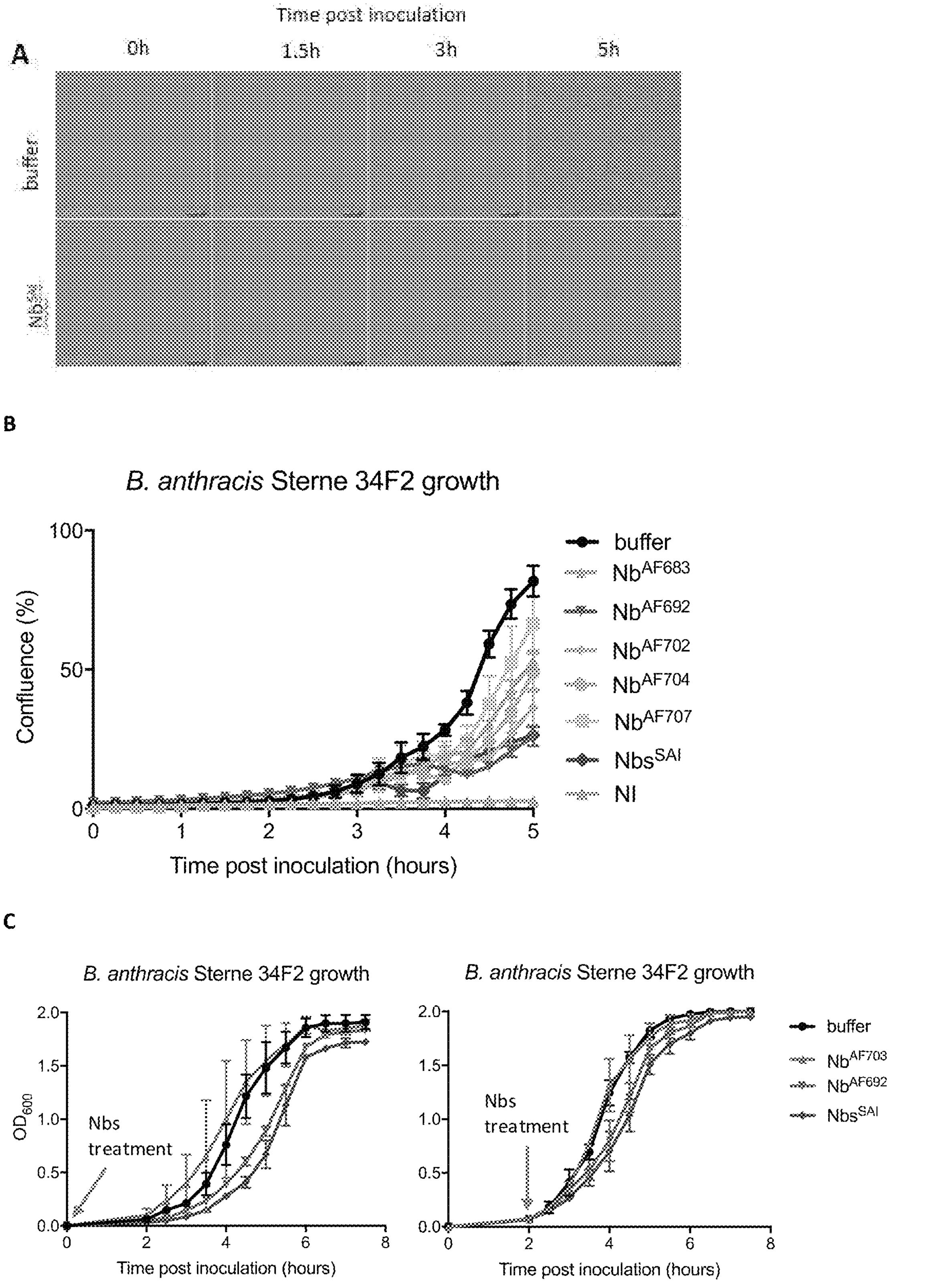

A

Time post inoculation
0h    1.5h    3h    5h buffer

Nb<sup>SAI</sup>

B

B. anthracis Sterne 34F2 growth

- buffer
- Nb$^{AF683}$
- Nb$^{AF692}$
- Nb$^{AF702}$
- Nb$^{AF704}$
- Nb$^{AF707}$
- Nbs$^{SAI}$
- NI X-axis: Time post inoculation (hours)
Y-axis: Confluence (%)

C

B. anthracis Sterne 34F2 growth

Nbs treatment

B. anthracis Sterne 34F2 growth

Nbs treatment

- buffer
- Nb$^{AF703}$
- Nb$^{AF692}$
- Nbs$^{SAI}$

X-axis: Time post inoculation (hours)
Y-axis: OD$_{600}$

D

A

B

D

*B. anthracis* Sterne 34F growth

- Nb$^{AF692}$
- Nbs$^{SAl}$
- buffer

OD$_{600}$ (2h PI) vs [Nbs] (nM)

A

Hours post inoculation: 0 3 4 5 0 3 4 5
MW (kDa): 100, 70, 55, 40, 35, 25, 15, 10
Nb$^{SAl}$ — Nb$^{AF692}$ — C

B

OD$_{600}$ vs Hours post inoculation

C

D

D

E

A

B

C

D

E

SEQUENCE LISTING

```
<160> NUMBER OF SEQ ID NOS: 54

<210> SEQ ID NO 1
<211> LENGTH: 814
<212> TYPE: PRT
<213> ORGANISM: Bacillus anthracis

<400> SEQUENCE: 1

Met Ala Lys Thr Asn Ser Tyr Lys Lys Val Ile Ala Gly Thr Met Thr
1               5                   10                  15

Ala Ala Met Val Ala Gly Val Val Ser Pro Val Ala Ala Ala Gly Lys
            20                  25                  30

Thr Phe Pro Asp Val Pro Ala Asp His Trp Gly Ile Asp Ser Ile Asn
        35                  40                  45

Tyr Leu Val Glu Lys Gly Ala Val Lys Gly Asn Asp Lys Gly Met Phe
    50                  55                  60

Glu Pro Gly Lys Glu Leu Thr Arg Ala Glu Ala Ala Thr Met Met Ala
65                  70                  75                  80

Gln Ile Leu Asn Leu Pro Ile Asp Lys Asp Ala Lys Pro Ser Phe Ala
                85                  90                  95

Asp Ser Gln Gly Gln Trp Tyr Thr Pro Phe Ile Ala Ala Val Glu Lys
```

-continued

```
            100                 105                 110

Ala Gly Val Ile Lys Gly Thr Gly Asn Gly Phe Glu Pro Asn Gly Lys
        115                 120                 125

Ile Asp Arg Val Ser Met Ala Ser Leu Leu Val Glu Ala Tyr Lys Leu
    130                 135                 140

Asp Thr Lys Val Asn Gly Thr Pro Ala Thr Lys Phe Lys Asp Leu Glu
145                 150                 155                 160

Thr Leu Asn Trp Gly Lys Glu Lys Ala Asn Ile Leu Val Glu Leu Gly
                165                 170                 175

Ile Ser Val Gly Thr Gly Asp Gln Trp Glu Pro Lys Lys Thr Val Thr
            180                 185                 190

Lys Ala Glu Ala Ala Gln Phe Ile Ala Lys Thr Asp Lys Gln Phe Gly
        195                 200                 205

Thr Glu Ala Ala Lys Val Glu Ser Ala Lys Ala Val Thr Thr Gln Lys
    210                 215                 220

Val Glu Val Lys Phe Ser Lys Ala Val Glu Lys Leu Thr Lys Glu Asp
225                 230                 235                 240

Ile Lys Val Thr Asn Lys Ala Asn Asn Asp Lys Val Leu Val Lys Glu
                245                 250                 255

Val Thr Leu Ser Glu Asp Lys Lys Ser Ala Thr Val Glu Leu Tyr Ser
            260                 265                 270

Asn Leu Ala Ala Lys Gln Thr Tyr Thr Val Asp Val Asn Lys Val Gly
        275                 280                 285

Lys Thr Glu Val Ala Val Gly Ser Leu Glu Ala Lys Thr Ile Glu Met
    290                 295                 300

Ala Asp Gln Thr Val Val Ala Asp Glu Pro Thr Ala Leu Gln Phe Thr
305                 310                 315                 320

Val Lys Asp Glu Asn Gly Thr Glu Val Val Ser Pro Glu Gly Ile Glu
                325                 330                 335

Phe Val Thr Pro Ala Ala Glu Lys Ile Asn Ala Lys Gly Glu Ile Thr
            340                 345                 350

Leu Ala Lys Gly Thr Ser Thr Thr Val Lys Ala Val Tyr Lys Lys Asp
        355                 360                 365

Gly Lys Val Val Ala Glu Ser Lys Glu Val Lys Val Ser Ala Glu Gly
    370                 375                 380

Ala Ala Val Ala Ser Ile Ser Asn Trp Thr Val Ala Glu Gln Asn Lys
385                 390                 395                 400

Ala Asp Phe Thr Ser Lys Asp Phe Lys Gln Asn Asn Lys Val Tyr Glu
                405                 410                 415

Gly Asp Asn Ala Tyr Val Gln Val Glu Leu Lys Asp Gln Phe Asn Ala
            420                 425                 430

Val Thr Thr Gly Lys Val Glu Tyr Glu Ser Leu Asn Thr Glu Val Ala
        435                 440                 445

Val Val Asp Lys Ala Thr Gly Lys Val Thr Val Leu Ser Ala Gly Lys
    450                 455                 460

Ala Pro Val Lys Val Thr Val Lys Asp Ser Lys Gly Lys Glu Leu Val
465                 470                 475                 480

Ser Lys Thr Val Glu Ile Glu Ala Phe Ala Gln Lys Ala Met Lys Glu
                485                 490                 495

Ile Lys Leu Glu Lys Thr Asn Val Ala Leu Ser Thr Lys Asp Val Thr
            500                 505                 510

Asp Leu Lys Val Lys Ala Pro Val Leu Asp Gln Tyr Gly Lys Glu Phe
        515                 520                 525
```

Thr Ala Pro Val Thr Val Lys Val Leu Asp Lys Asp Gly Lys Glu Leu
    530                 535                 540

Lys Glu Gln Lys Leu Glu Ala Lys Tyr Val Asn Lys Glu Leu Val Leu
545                 550                 555                 560

Asn Ala Ala Gly Gln Glu Ala Gly Asn Tyr Thr Val Val Leu Thr Ala
                565                 570                 575

Lys Ser Gly Glu Lys Glu Ala Lys Ala Thr Leu Ala Leu Glu Leu Lys
            580                 585                 590

Ala Pro Gly Ala Phe Ser Lys Phe Glu Val Arg Gly Leu Glu Lys Glu
        595                 600                 605

Leu Asp Lys Tyr Val Thr Glu Glu Asn Gln Lys Asn Ala Met Thr Val
    610                 615                 620

Ser Val Leu Pro Val Asp Ala Asn Gly Leu Val Leu Lys Gly Ala Glu
625                 630                 635                 640

Ala Ala Glu Leu Lys Val Thr Thr Thr Asn Lys Glu Gly Lys Glu Val
                645                 650                 655

Asp Ala Thr Asp Ala Gln Val Thr Val Gln Asn Asn Ser Val Ile Thr
            660                 665                 670

Val Gly Gln Gly Ala Lys Ala Gly Glu Thr Tyr Lys Val Thr Val Val
        675                 680                 685

Leu Asp Gly Lys Leu Ile Thr Thr His Ser Phe Lys Val Val Asp Thr
    690                 695                 700

Ala Pro Thr Ala Lys Gly Leu Ala Val Glu Phe Thr Ser Thr Ser Leu
705                 710                 715                 720

Lys Glu Val Ala Pro Asn Ala Asp Leu Lys Ala Ala Leu Leu Asn Ile
                725                 730                 735

Leu Ser Val Asp Gly Val Pro Ala Thr Thr Ala Lys Ala Thr Val Ser
            740                 745                 750

Asn Val Glu Phe Val Ser Ala Asp Thr Asn Val Val Ala Glu Asn Gly
        755                 760                 765

Thr Val Gly Ala Lys Gly Ala Thr Ser Ile Tyr Val Lys Asn Leu Thr
    770                 775                 780

Val Val Lys Asp Gly Lys Glu Gln Lys Val Glu Phe Asp Lys Ala Val
785                 790                 795                 800

Gln Val Ala Val Ser Ile Lys Glu Ala Lys Pro Ala Thr Lys
                805                 810

<210> SEQ ID NO 2
<211> LENGTH: 2445
<212> TYPE: DNA
<213> ORGANISM: Bacillus anthracis

<400> SEQUENCE: 2
atggcaaaga ctaactctta caaaaaagta atcgctggta caatgacagc agcaatggta 60
gcaggtgttg tttctccagt agcagcagca ggtaaaacat tcccagacgt tcctgctgat 120
cactggggaa ttgattctat taactactta gtagaaaaag gcgcagttaa aggtaacgac 180
aaaggaatgt tcgagcctgg aaaagaatta actcgtgcag aagcagctac aatgatggct 240
caaatcttaa acttaccaat cgataaagat gctaaaccat ctttcgctga ctctcaaggc 300
caatggtaca ctccattcat cgcagctgta gaaaaagctg gcgttattaa aggtacagga 360
aacggctttg agccaaacgg aaaaatcgac cgcgtttcta tggcatctct tcttgtagaa 420
gcttacaaat tagatactaa agtaaacggt actccagcaa ctaaattcaa agatttagaa 480

-continued

```
acattaaact ggggtaaaga aaaagctaac atcttagttg aattaggaat ctctgttggt    540

actggtgatc aatgggagcc taagaaaact gtaactaaag cagaagctgc tcaattcatt    600

gctaagactg acaagcagtt cggtacagaa gcagcaaaag ttgaatctgc aaaagctgtt    660

acaactcaaa aagtagaagt taaattcagc aaagctgttg aaaaattaac taaagaagat    720

atcaaagtaa ctaacaaagc taacaacgat aaagtactag ttaaagaggt aactttatca    780

gaagataaaa aatctgctac agttgaatta tatagtaact tagcagctaa acaaacttac    840

actgtagatg taaacaaagt tggtaaaaca gaagtagctg taggttcttt agaagcaaaa    900

acaatcgaaa tggctgacca aacagttgta gctgatgagc caacagcatt acaattcaca    960

gttaaagatg aaaacggtac tgaagttgtt tcaccagagg gtattgaatt tgtaacgcca   1020

gctgcagaaa aaattaatgc aaaaggtgaa atcactttag caaaaggtac ttcaactact   1080

gtaaaagctg tttataaaaa agacggtaaa gtagtagctg aaagtaaaga agtaaaagtt   1140

tctgctgaag gtgctgcagt agcttcaatc tctaactgga cagttgcaga acaaaataaa   1200

gctgacttta cttctaaaga tttcaaacaa aacaataaag tttacgaagg cgacaacgct   1260

tacgttcaag tagaattgaa agatcaattt aacgcagtaa caactggaaa agttgaatat   1320

gagtcgttaa acacagaagt tgctgtagta gataaagcta ctggtaaagt aactgtatta   1380

tctgcaggaa aagcaccagt aaaagtaact gtaaaagatt caaaaggtaa agaacttgtt   1440

tcaaaaacag ttgaaattga agctttcgct caaaaagcaa tgaaagaaat taaattagaa   1500

aaaactaacg tagcgctttc tacaaaagat gtaacagatt taaaagtaaa agctccagta   1560

ctagatcaat acggtaaaga gtttacagct cctgtaacag tgaaagtact tgataaagat   1620

ggtaaagaat taaaagaaca aaaattagaa gctaaatatg tgaacaaaga attagttctg   1680

aatgcagcag gtcaagaagc tggtaattat acagttgtat taactgcaaa atctggtgaa   1740

aaagaagcaa aagctacatt agctctagaa ttaaaagctc caggtgcatt ctctaaattt   1800

gaagttcgtg gtttagaaaa agaattagat aaatatgtta ctgaggaaaa ccaaaagaat   1860

gcaatgactg tttcagttct tcctgtagat gcaaatggat tagtattaaa aggtgcagaa   1920

gcagctgaac taaaagtaac aacaacaaac aaagaaggta aagaagtaga cgcaactgat   1980

gcacaagtta ctgtacaaaa taacagtgta attactgttg gtcaaggtgc aaaagctggt   2040

gaaacttata aagtaacagt tgtactagat ggtaaattaa tcacaactca ttcattcaaa   2100

gttgttgata cagcaccaac tgctaaagga ttagcagtag aatttacaag cacatctctt   2160

aaagaagtag ctccaaatgc tgatttaaaa gctgcacttt taaatatctt atctgttgat   2220

ggtgtacctg cgactacagc aaaagcaaca gtttctaatg tagaatttgt ttctgctgac   2280

acaaatgttg tagctgaaaa tggtacagtt ggtgcaaaag gtgcaacatc tatctatgtg   2340

aaaaacctga cagttgtaaa agatggaaaa gagcaaaaag tagaatttga taaagctgta   2400

caagttgcag tttctattaa agaagcaaaa cctgcaacaa aataa                   2445
```

```
<210> SEQ ID NO 3
<211> LENGTH: 2442
<212> TYPE: DNA
<213> ORGANISM: Artificial Sequence
<220> FEATURE:
<223> OTHER INFORMATION: E.coli codon usage optimized B.anthracis sterne
      SAP coding sequence

<400> SEQUENCE: 3

atggctaaga cgaatagcta caaaaaagtg attgcgggca ctatgaccgc ggcaatggtc     60
```

-continued

```
gctggtgtgg tttctccggt agccgcagcc ggtaagacct tcccggacgt tccggcggat    120
cattggggca tcgactctat caattatctc gttgagaagg gcgctgtgaa gggcaatgac    180
aagggcatgt ttgagccagg caaggaactc acgcgcgctg aggcagcaac catgatggcg    240
caaattctga acctgccgat tgataaggac gcaaaacctt ccttcgctga cagccagggc    300
cagtggtaca cccctttat tgcagcggtg gagaaggcgg gtgtaatcaa aggcactggt    360
aatggctttg aaccgaatgg taagatcgac cgtgtttcta tggcgtctct gctggtcgaa    420
gcgtataaac tcgacaccaa agttaacggt actccggcca cgaagtttaa ggacctggaa    480
accctcaact ggggtaagga aaaggctaac atcctggttg aactcggcat ctctgtgggc    540
acgggcgacc agtgggagcc gaagaaaacc gttaccaagg ctgaagctgc tcagttcatt    600
gcgaagaccg acaagcaatt tggtactgag gctgccaaag tagagtccgc gaaggccgtg    660
acgactcaga aagtggaagt gaagttctct aaggctgtcg agaagctcac gaaagaagat    720
atcaaagtaa cgaacaaggc aaacaacgac aaagtcctcg taaaggaagt tacgctgtcc    780
gaagataaaa aatccgccac cgtggaactg tactctaacc tggcggcgaa gcaaacgtac    840
accgtagacg ttaataaggt tggcaagact gaggtagcag tgggttctct cgaagccaag    900
acgatcgaaa tggcagacca gactgtggtt gccgatgagc cgaccgcact gcaatttacg    960
gtgaaagatg aaaacggcac ggaagttgtt tcccctgagg gtattgagtt tgtgaccccg   1020
gcagctgaaa agatcaatgc taagggcgag attaccctcg cgaaaggtac tagcacgact   1080
gttaaagccg tttacaagaa agacggtaag gtcgtagcgg aatctaaaga agtaaaggta   1140
agcgcggaag gtgcggcagt tgcgtctatt tctaactgga cggttgcgga acagaataaa   1200
gctgacttca cgagcaaaga ctttaagcaa aacaacaagg tctacgaggg tgacaacgcg   1260
tacgtgcagg tagaactgaa agaccaattt aacgcagtta cgaccggtaa agttgaatac   1320
gaatctctga acaccgaagt ggcagtggtg gacaaagcaa ctggcaaggt gactgtgctg   1380
tctgcaggca aagcacctgt aaaagtcacg gttaaagatt ccaagggtaa agaactcgtt   1440
tctaaaactg ttgagatcga agcattcgca cagaaagcga tgaaggaaat taagctggag   1500
aaaacgaatg ttgcgctctc tacgaaggac gtaacggacc tgaaggtcaa agctccggtc   1560
ctggaccagt acggcaaaga attcacggcg ccagttactg tcaaagttct ggataaagat   1620
ggtaaagagc tcaaggagca gaaactggag gcgaagtacg tgaacaaaga gctcgtgctc   1680
aacgcggcag gccaggaggc gggcaattac acggttgttc tcactgcgaa atctggcgag   1740
aaagaggcta aggcaacgct cgcgctggag ctgaaggctc caggcgcgtt ttccaaattc   1800
gaagttcgtg gtctcgaaaa ggagctcgat aagtatgtta ctgaagagaa tcagaagaat   1860
gcgatgaccg taagcgtcct cccggtggac gcgaacggtc tggtgctgaa aggcgcagaa   1920
gcggccgaac tcaaggttac caccaccaat aaagagggca aggaggttga cgcgacggac   1980
gcgcaagtca ctgtacaaaa taactctgtt atcaccgttg gtcagggtgc gaaagcgggc   2040
gaaacttaca aggtaaccgt tgtgctcgac ggcaagctca ttacgacgca tagcttcaaa   2100
gtcgtggaca cggccccaac ggccaaaggc ctggcagtag aatttaccag cacctctctc   2160
aaagaggtgg cccctaatgc ggatctgaaa gcagcactgc tgaacattct cagcgttgac   2220
ggcgtacctg cgaccaccgc caaagcgacc gtatctaacg ttgaattcgt gtctgctgac   2280
actaacgtag tcgcggaaaa tggtaccgtg ggcgctaaag gtgctacttc tatttacgtc   2340
aaaaacctga ctgttgttaa ggatggcaaa gaacaaaagg tagagttcga caaggcggta   2400
caggttgcag tttccattaa ggaggccaaa ccagcaacga aa                      2442
```

<210> SEQ ID NO 4
<211> LENGTH: 606
<212> TYPE: PRT
<213> ORGANISM: Artificial Sequence
<220> FEATURE:
<223> OTHER INFORMATION: SAP amino acid sequence w/o SLH domain (aa 216-814 of SEQ ID NO:1) with C-terminal His6 tag

<400> SEQUENCE: 4

```
Met Ser Ala Lys Ala Val Thr Thr Gln Lys Val Glu Val Lys Phe Ser
1               5                   10                  15

Lys Ala Val Glu Lys Leu Thr Lys Glu Asp Ile Lys Val Thr Asn Lys
            20                  25                  30

Ala Asn Asn Asp Lys Val Leu Val Lys Glu Val Thr Leu Ser Glu Asp
        35                  40                  45

Lys Lys Ser Ala Thr Val Glu Leu Tyr Ser Asn Leu Ala Ala Lys Gln
    50                  55                  60

Thr Tyr Thr Val Asp Val Asn Lys Val Gly Lys Thr Glu Val Ala Val
65                  70                  75                  80

Gly Ser Leu Glu Ala Lys Thr Ile Glu Met Ala Asp Gln Thr Val Val
                85                  90                  95

Ala Asp Glu Pro Thr Ala Leu Gln Phe Thr Val Lys Asp Glu Asn Gly
            100                 105                 110

Thr Glu Val Val Ser Pro Glu Gly Ile Glu Phe Val Thr Pro Ala Ala
        115                 120                 125

Glu Lys Ile Asn Ala Lys Gly Glu Ile Thr Leu Ala Lys Gly Thr Ser
    130                 135                 140

Thr Thr Val Lys Ala Val Tyr Lys Lys Asp Gly Lys Val Val Ala Glu
145                 150                 155                 160

Ser Lys Glu Val Lys Val Ser Ala Glu Gly Ala Ala Val Ala Ser Ile
                165                 170                 175

Ser Asn Trp Thr Val Ala Glu Gln Asn Lys Ala Asp Phe Thr Ser Lys
            180                 185                 190

Asp Phe Lys Gln Asn Asn Lys Val Tyr Glu Gly Asp Asn Ala Tyr Val
        195                 200                 205

Gln Val Glu Leu Lys Asp Gln Phe Asn Ala Val Thr Thr Gly Lys Val
    210                 215                 220

Glu Tyr Glu Ser Leu Asn Thr Glu Val Ala Val Val Asp Lys Ala Thr
225                 230                 235                 240

Gly Lys Val Thr Val Leu Ser Ala Gly Lys Ala Pro Val Lys Val Thr
                245                 250                 255

Val Lys Asp Ser Lys Gly Lys Glu Leu Val Ser Lys Thr Val Glu Ile
            260                 265                 270

Glu Ala Phe Ala Gln Lys Ala Met Lys Glu Ile Lys Leu Glu Lys Thr
        275                 280                 285

Asn Val Ala Leu Ser Thr Lys Asp Val Thr Asp Leu Lys Val Lys Ala
    290                 295                 300

Pro Val Leu Asp Gln Tyr Gly Lys Glu Phe Thr Ala Pro Val Thr Val
305                 310                 315                 320

Lys Val Leu Asp Lys Asp Gly Lys Glu Leu Lys Glu Gln Lys Leu Glu
                325                 330                 335

Ala Lys Tyr Val Asn Lys Glu Leu Val Leu Asn Ala Ala Gly Gln Glu
            340                 345                 350

Ala Gly Asn Tyr Thr Val Val Leu Thr Ala Lys Ser Gly Glu Lys Glu
```

```
        355                 360                 365

Ala Lys Ala Thr Leu Ala Leu Glu Leu Lys Ala Pro Gly Ala Phe Ser
    370                 375                 380

Lys Phe Glu Val Arg Gly Leu Glu Lys Glu Leu Asp Lys Tyr Val Thr
385                 390                 395                 400

Glu Glu Asn Gln Lys Asn Ala Met Thr Val Ser Val Leu Pro Val Asp
                405                 410                 415

Ala Asn Gly Leu Val Leu Lys Gly Ala Glu Ala Ala Glu Leu Lys Val
            420                 425                 430

Thr Thr Thr Asn Lys Glu Gly Lys Glu Val Asp Ala Thr Asp Ala Gln
        435                 440                 445

Val Thr Val Gln Asn Asn Ser Val Ile Thr Val Gly Gln Gly Ala Lys
    450                 455                 460

Ala Gly Glu Thr Tyr Lys Val Thr Val Val Leu Asp Gly Lys Leu Ile
465                 470                 475                 480

Thr Thr His Ser Phe Lys Val Val Asp Thr Ala Pro Thr Ala Lys Gly
                485                 490                 495

Leu Ala Val Glu Phe Thr Ser Thr Ser Leu Lys Glu Val Ala Pro Asn
            500                 505                 510

Ala Asp Leu Lys Ala Ala Leu Leu Asn Ile Leu Ser Val Asp Gly Val
        515                 520                 525

Pro Ala Thr Thr Ala Lys Ala Thr Val Ser Asn Val Glu Phe Val Ser
    530                 535                 540

Ala Asp Thr Asn Val Val Ala Glu Asn Gly Thr Val Gly Ala Lys Gly
545                 550                 555                 560

Ala Thr Ser Ile Tyr Val Lys Asn Leu Thr Val Val Lys Asp Gly Lys
                565                 570                 575

Glu Gln Lys Val Glu Phe Asp Lys Ala Val Gln Val Ala Val Ser Ile
            580                 585                 590

Lys Glu Ala Lys Pro Ala Thr Lys His His His His His His
        595                 600                 605


<210> SEQ ID NO 5
<211> LENGTH: 1821
<212> TYPE: DNA
<213> ORGANISM: Artificial Sequence
<220> FEATURE:
<223> OTHER INFORMATION: E.coli codon usage optimized B.anthracis sterne
      SAP coding sequence of SAP encoded by SEQ ID NO:4

<400> SEQUENCE: 5

atgtccgcga aggccgtgac gactcagaaa gtggaagtga agttctctaa ggctgtcgag      60

aagctcacga aagaagatat caaagtaacg aacaaggcaa acaacgacaa agtcctcgta     120

aaggaagtta cgctgtccga agataaaaaa tccgccaccg tggaactgta ctctaacctg     180

gcggcgaagc aaacgtacac cgtagacgtt aataaggttg gcaagactga ggtagcagtg     240

ggttctctcg aagccaagac gatcgaaatg gcagaccaga ctgtggttgc cgatgagccg     300

accgcactgc aatttacggt gaaagatgaa aacggcacgg aagttgtttc ccctgagggt     360

attgagtttg tgaccccggc agctgaaaag atcaatgcta agggcgagat taccctcgcg     420

aaaggtacta gcacgactgt taaagccgtt tacaagaaag acggtaaggt cgtagcggaa     480

tctaaagaag taaaggtaag cgcggaaggt gcggcagttg cgtctatttc taactggacg     540

gttgcggaac agaataaagc tgacttcacg agcaaagact ttaagcaaaa caacaaggtc     600

tacgagggtg acaacgcgta cgtgcaggta gaactgaaag accaatttaa cgcagttacg     660
```

```
accggtaaag ttgaatacga atctctgaac accgaagtgg cagtggtgga caaagcaact    720

ggcaaggtga ctgtgctgtc tgcaggcaaa gcacctgtaa aagtcacggt taaagattcc    780

aagggtaaag aactcgtttc taaaactgtt gagatcgaag cattcgcaca gaaagcgatg    840

aaggaaatta agctggagaa aacgaatgtt gcgctctcta cgaaggacgt aacggacctg    900

aaggtcaaag ctccggtcct ggaccagtac ggcaaagaat tcacggcgcc agttactgtc    960

aaagttctgg ataaagatgg taaagagctc aaggagcaga aactggaggc gaagtacgtg   1020

aacaaagagc tcgtgctcaa cgcggcaggc caggaggcgg gcaattacac ggttgttctc   1080

actgcgaaat ctggcgagaa agaggctaag gcaacgctcg cgctggagct gaaggctcca   1140

ggcgcgtttt ccaaattcga agttcgtggt ctcgaaaagg agctcgataa gtatgttact   1200

gaagagaatc agaagaatgc gatgaccgta agcgtcctcc cggtggacgc gaacggtctg   1260

gtgctgaaag gcgcagaagc ggccgaactc aaggttacca ccaccaataa agagggcaag   1320

gaggttgacg cgacggacgc gcaagtcact gtacaaaata actctgttat caccgttggt   1380

cagggtgcga aagcgggcga aacttacaag gtaaccgttg tgctcgacgg caagctcatt   1440

acgacgcata gcttcaaagt cgtggacacg gccccaacgg ccaaaggcct ggcagtagaa   1500

tttaccagca cctctctcaa agaggtggcc cctaatgcgg atctgaaagc agcactgctg   1560

aacattctca gcgttgacgg cgtacctgcg accaccgcca aagcgaccgt atctaacgtt   1620

gaattcgtgt ctgctgacac taacgtagtc gcggaaaatg gtaccgtggg cgctaaaggt   1680

gctacttcta tttacgtcaa aaacctgact gttgttaagg atggcaaaga acaaaaggta   1740

gagttcgaca aggcggtaca ggttgcagtt tccattaagg aggccaaacc agcaacgaaa   1800

catcaccatc accatcacta a                                             1821
```

```
<210> SEQ ID NO 6
<211> LENGTH: 81
<212> TYPE: PRT
<213> ORGANISM: Bacillus anthracis

<400> SEQUENCE: 6

Met Ser Ala Lys Ala Val Thr Thr Gln Lys Val Glu Val Lys Phe Ser
1               5                   10                  15

Lys Ala Val Glu Lys Leu Thr Lys Glu Asp Ile Lys Val Thr Asn Lys
            20                  25                  30

Ala Asn Asn Asp Lys Val Leu Val Lys Glu Val Thr Leu Ser Glu Asp
        35                  40                  45

Lys Lys Ser Ala Thr Val Glu Leu Tyr Ser Asn Leu Ala Ala Lys Gln
    50                  55                  60

Thr Tyr Thr Val Asp Val Asn Lys Val Gly Lys Thr Glu Val Ala Val
65                  70                  75                  80

Gly


<210> SEQ ID NO 7
<211> LENGTH: 90
<212> TYPE: PRT
<213> ORGANISM: Bacillus anthracis

<400> SEQUENCE: 7

Met Ser Leu Glu Ala Lys Thr Ile Glu Met Ala Asp Gln Thr Val Val
1               5                   10                  15

Ala Asp Glu Pro Thr Ala Leu Gln Phe Thr Val Lys Asp Glu Asn Gly
            20                  25                  30
```

```
Thr Glu Val Val Ser Pro Glu Gly Ile Glu Phe Val Thr Pro Ala Ala
        35                  40                  45

Glu Lys Ile Asn Ala Lys Gly Glu Ile Thr Leu Ala Lys Gly Thr Ser
    50                  55                  60

Thr Thr Val Lys Ala Val Tyr Lys Lys Asp Gly Lys Val Val Ala Glu
65                  70                  75                  80

Ser Lys Glu Val Lys Val Ser Ala Glu Gly
                85                  90


<210> SEQ ID NO 8
<211> LENGTH: 108
<212> TYPE: PRT
<213> ORGANISM: Bacillus anthracis

<400> SEQUENCE: 8

Met Gly Ala Ala Val Ala Ser Ile Ser Asn Trp Thr Val Ala Glu Gln
1               5                   10                  15

Asn Lys Ala Asp Phe Thr Ser Lys Asp Phe Lys Gln Asn Asn Lys Val
            20                  25                  30

Tyr Glu Gly Asp Asn Ala Tyr Val Gln Val Glu Leu Lys Asp Gln Phe
        35                  40                  45

Asn Ala Val Thr Thr Gly Lys Val Glu Tyr Glu Ser Leu Asn Thr Glu
    50                  55                  60

Val Ala Val Val Asp Lys Ala Thr Gly Lys Val Thr Val Leu Ser Ala
65                  70                  75                  80

Gly Lys Ala Pro Val Lys Val Thr Val Lys Asp Ser Lys Gly Lys Glu
                85                  90                  95

Leu Val Ser Lys Thr Val Glu Ile Glu Ala Phe Ala
            100                 105


<210> SEQ ID NO 9
<211> LENGTH: 106
<212> TYPE: PRT
<213> ORGANISM: Bacillus anthracis

<400> SEQUENCE: 9

Met Gln Lys Ala Met Lys Glu Ile Lys Leu Glu Lys Thr Asn Val Ala
1               5                   10                  15

Leu Ser Thr Lys Asp Val Thr Asp Leu Lys Val Lys Ala Pro Val Leu
            20                  25                  30

Asp Gln Tyr Gly Lys Glu Phe Thr Ala Pro Val Thr Val Lys Val Leu
        35                  40                  45

Asp Lys Asp Gly Lys Glu Leu Lys Glu Gln Lys Leu Glu Ala Lys Tyr
    50                  55                  60

Val Asn Lys Glu Leu Val Leu Asn Ala Ala Gly Gln Glu Ala Gly Asn
65                  70                  75                  80

Tyr Thr Val Val Leu Thr Ala Lys Ser Gly Glu Lys Glu Ala Lys Ala
                85                  90                  95

Thr Leu Ala Leu Glu Leu Lys Ala Pro Gly
            100                 105


<210> SEQ ID NO 10
<211> LENGTH: 112
<212> TYPE: PRT
<213> ORGANISM: Bacillus anthracis

<400> SEQUENCE: 10
```

```
Met Ala Phe Ser Lys Phe Glu Val Arg Gly Leu Glu Lys Glu Leu Asp
1               5                   10                  15

Lys Tyr Val Thr Glu Glu Asn Gln Lys Asn Ala Met Thr Val Ser Val
            20                  25                  30

Leu Pro Val Asp Ala Asn Gly Leu Val Leu Lys Gly Ala Glu Ala Ala
        35                  40                  45

Glu Leu Lys Val Thr Thr Thr Asn Lys Glu Gly Lys Glu Val Asp Ala
    50                  55                  60

Thr Asp Ala Gln Val Thr Val Gln Asn Asn Ser Val Ile Thr Val Gly
65                  70                  75                  80

Gln Gly Ala Lys Ala Gly Glu Thr Tyr Lys Val Thr Val Val Leu Asp
                85                  90                  95

Gly Lys Leu Ile Thr Thr His Ser Phe Lys Val Val Asp Thr Ala Pro
            100                 105                 110


<210> SEQ ID NO 11
<211> LENGTH: 109
<212> TYPE: PRT
<213> ORGANISM: Bacillus anthracis

<400> SEQUENCE: 11

Met Thr Ala Lys Gly Leu Ala Val Glu Phe Thr Ser Thr Ser Leu Lys
1               5                   10                  15

Glu Val Ala Pro Asn Ala Asp Leu Lys Ala Ala Leu Leu Asn Ile Leu
            20                  25                  30

Ser Val Asp Gly Val Pro Ala Thr Thr Ala Lys Ala Thr Val Ser Asn
        35                  40                  45

Val Glu Phe Val Ser Ala Asp Thr Asn Val Val Ala Glu Asn Gly Thr
    50                  55                  60

Val Gly Ala Lys Gly Ala Thr Ser Ile Tyr Val Lys Asn Leu Thr Val
65                  70                  75                  80

Val Lys Asp Gly Lys Glu Gln Lys Val Glu Phe Asp Lys Ala Val Gln
                85                  90                  95

Val Ala Val Ser Ile Lys Glu Ala Lys Pro Ala Thr Lys
            100                 105


<210> SEQ ID NO 12
<211> LENGTH: 129
<212> TYPE: PRT
<213> ORGANISM: Artificial Sequence
<220> FEATURE:
<223> OTHER INFORMATION: anti-SAP Nanobody 683

<400> SEQUENCE: 12

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Asp Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Lys Met Val Tyr Leu
65                  70                  75                  80

Gln Met Asn Ser Leu Lys Pro Glu Asp Thr Ala Val Tyr Tyr Cys His
                85                  90                  95

Ala Asp Phe Ser Thr Gly Trp Ala Pro Tyr Asp Tyr Trp Gly Gln Gly
```

-continued

```
            100                 105                 110

Thr Gln Val Thr Val Ser Ser His His His His His His Glu Pro Glu
        115                 120                 125

Ala


<210> SEQ ID NO 13
<211> LENGTH: 130
<212> TYPE: PRT
<213> ORGANISM: Artificial Sequence
<220> FEATURE:
<223> OTHER INFORMATION: anti-SAP Nanobody 688

<400> SEQUENCE: 13

Gln Val Gln Leu Val Glu Ser Gly Gly Gly Leu Val Arg Ala Gly Gly
1               5                   10                  15

Ser Leu Arg Leu Ser Cys Ala Ala Ser Gly Ser Ile Phe Arg Ile Asn
            20                  25                  30

Asp Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Phe Ser Thr Val Arg Glu Arg Arg Tyr Asp Tyr Trp Gly Gln
            100                 105                 110

Gly Thr Gln Val Thr Val Ser Ser His His His His His His Glu Pro
        115                 120                 125

Glu Ala
    130


<210> SEQ ID NO 14
<211> LENGTH: 128
<212> TYPE: PRT
<213> ORGANISM: Artificial Sequence
<220> FEATURE:
<223> OTHER INFORMATION: anti-SAP Nanobody 692

<400> SEQUENCE: 14

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Asp Met Gly Trp Tyr Arg Gln Ala Pro Gly Lys Gln Arg Glu Leu Val
        35                  40                  45

Ala Val Ile Thr Ser Gly Gly Ser Ala Asn Tyr Ala Asp Ser Val Lys
    50                  55                  60

Gly Arg Phe Ser Ile Ser Arg Asp Asn Ala Lys Lys Ala Val Tyr Leu
65                  70                  75                  80

Arg Met Asn Ser Leu Lys Pro Glu Asp Thr Ala Val Tyr Tyr Cys Asn
                85                  90                  95

Ala Asp Phe Gly Thr Leu Gly Arg Tyr Asp Tyr Trp Gly Gln Gly Thr
            100                 105                 110

Gln Val Thr Val Ser Ser His His His His His His Glu Pro Glu Ala
        115                 120                 125
```

<210> SEQ ID NO 15
<211> LENGTH: 129
<212> TYPE: PRT
<213> ORGANISM: Artificial Sequence
<220> FEATURE:
<223> OTHER INFORMATION: anti-SAP Nanobody 702

<400> SEQUENCE: 15

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Val Asn
            20                  25                  30

Asp Met Gly Trp Tyr Arg Gln Ala Pro Gly Lys Gln Arg Glu Leu Val
        35                  40                  45

Ala Ile Ile Ile Thr Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Asp Phe Gly Thr Gly Pro Gly Arg Tyr Asp Tyr Trp Gly Gln Gly
            100                 105                 110

Thr Gln Val Thr Val Ser Ser His His His His His His Glu Pro Glu
        115                 120                 125

Ala
```

<210> SEQ ID NO 16
<211> LENGTH: 131
<212> TYPE: PRT
<213> ORGANISM: Artificial Sequence
<220> FEATURE:
<223> OTHER INFORMATION: anti-SAP Nanobody 704

<400> SEQUENCE: 16

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Ile Ala Trp Val Arg Gln Ala Pro Gly Lys Gly Leu Glu Trp Val
        35                  40                  45

Ser Asp Ile Asn Ser Gly Gly Thr Asp Thr Ser Tyr Ala Ala Ala Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Ala Lys Ser Ala Gln Ser Tyr Phe His Ser Thr Phe Asp His Arg Gly
            100                 105                 110

Gln Gly Thr Gln Val Thr Val Ser Ser His His His His His His Glu
        115                 120                 125

Pro Glu Ala
    130
```

<210> SEQ ID NO 17
<211> LENGTH: 129
<212> TYPE: PRT
<213> ORGANISM: Artificial Sequence
<220> FEATURE:
<223> OTHER INFORMATION: anti-SAP Nanobody 707

<400> SEQUENCE: 17

Gln Val Gln Leu Val Glu Ser Gly Gly Gly Leu Val Gln Ala Gly Gly
1 5 10 15

Ser Leu Arg Leu Ser Cys Ala Ala Ser Gly Ser Ile Phe Arg Ile Asn
20 25 30

Ala Met Gly Trp Tyr Arg Gln Ala Ser Gly Lys Gln Arg Glu Leu Val
35 40 45

Ala Ala Ile Thr Ser Gly Gly Asn Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Ala Asp Phe Gly Thr Gly Gly Arg Pro Tyr Asp Tyr Trp Gly Gln Gly
100 105 110

Thr Gln Val Thr Val Ser Ser His His His His His His Glu Pro Glu
115 120 125

Ala

<210> SEQ ID NO 18
<211> LENGTH: 129
<212> TYPE: PRT
<213> ORGANISM: Artificial Sequence
<220> FEATURE:
<223> OTHER INFORMATION: anti-SAP Nanobody 684

<400> SEQUENCE: 18

Gln Val Gln Leu Val Glu Ser Gly Gly Gly Leu Val Gln Ala Gly Gly
1 5 10 15

Ser Leu Arg Leu Phe Cys Ala Ala Ser Gly Ser Ile Phe Arg Val Asn
20 25 30

Ala Met Gly Trp Tyr Arg Gln Val Thr Gly Lys Gln Arg Glu Leu Val
35 40 45

Ala Ala Ile Thr Ser Gly Gly Arg Thr Asn Tyr Ala Asp Ser Val Lys
50 55 60

Gly Arg Phe Thr Ile Ser Arg Asp Asn Ile Lys Asn Thr Val Tyr Leu
65 70 75 80

Gln Met Asn Ser Leu Lys Pro Glu Asp Thr Ala Val Tyr Tyr Cys Asn
85 90 95

Ala Asp Leu Gly Thr Gly Gly Arg Ser Tyr Asp Tyr Trp Gly Gln Gly
100 105 110

Thr Gln Val Thr Val Ser Ser His His His His His His Glu Pro Glu
115 120 125

Ala

<210> SEQ ID NO 19
<211> LENGTH: 134
<212> TYPE: PRT
<213> ORGANISM: Artificial Sequence
<220> FEATURE:
<223> OTHER INFORMATION: anti-SAP Nanobody 694

<400> SEQUENCE: 19

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

```
            20                  25                  30

Pro Met Ser Trp Val Arg Gln Ala Pro Gly Lys Gly Leu Glu Trp Val
        35                  40                  45

Ser Asp Ile Asn Ser Ser Gly Thr Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Ala
                85                  90                  95

Thr Glu Gly Lys Tyr Gly Arg Thr Trp Tyr Gly Gln Leu Glu Tyr His
            100                 105                 110

Tyr Trp Gly Gln Gly Thr Gln Val Thr Val Ser Ser His His His His
        115                 120                 125

His His Glu Pro Glu Ala
    130


<210> SEQ ID NO 20
<211> LENGTH: 119
<212> TYPE: PRT
<213> ORGANISM: Artificial Sequence
<220> FEATURE:
<223> OTHER INFORMATION: anti-SAP Nanobody  683

<400> SEQUENCE: 20

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Asp Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Lys Met Val Tyr Leu
65                  70                  75                  80

Gln Met Asn Ser Leu Lys Pro Glu Asp Thr Ala Val Tyr Tyr Cys His
                85                  90                  95

Ala Asp Phe Ser Thr Gly Trp Ala Pro Tyr Asp Tyr Trp Gly Gln Gly
            100                 105                 110

Thr Gln Val Thr Val Ser Ser
        115


<210> SEQ ID NO 21
<211> LENGTH: 120
<212> TYPE: PRT
<213> ORGANISM: Artificial Sequence
<220> FEATURE:
<223> OTHER INFORMATION: anti-SAP Nanobody  688

<400> SEQUENCE: 21

Gln Val Gln Leu Val Glu Ser Gly Gly Gly Leu Val Arg Ala Gly Gly
1               5                   10                  15

Ser Leu Arg Leu Ser Cys Ala Ala Ser Gly Ser Ile Phe Arg Ile Asn
            20                  25                  30

Asp Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60
```

```
Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Phe Ser Thr Val Arg Glu Arg Arg Tyr Asp Tyr Trp Gly Gln
            100                 105                 110

Gly Thr Gln Val Thr Val Ser Ser
        115                 120


<210> SEQ ID NO 22
<211> LENGTH: 118
<212> TYPE: PRT
<213> ORGANISM: Artificial Sequence
<220> FEATURE:
<223> OTHER INFORMATION: anti-SAP Nanobody  692

<400> SEQUENCE: 22

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Asp Met Gly Trp Tyr Arg Gln Ala Pro Gly Lys Gln Arg Glu Leu Val
        35                  40                  45

Ala Val Ile Thr Ser Gly Gly Ser Ala Asn Tyr Ala Asp Ser Val Lys
    50                  55                  60

Gly Arg Phe Ser Ile Ser Arg Asp Asn Ala Lys Lys Ala Val Tyr Leu
65                  70                  75                  80

Arg Met Asn Ser Leu Lys Pro Glu Asp Thr Ala Val Tyr Tyr Cys Asn
                85                  90                  95

Ala Asp Phe Gly Thr Leu Gly Arg Tyr Asp Tyr Trp Gly Gln Gly Thr
            100                 105                 110

Gln Val Thr Val Ser Ser
        115


<210> SEQ ID NO 23
<211> LENGTH: 119
<212> TYPE: PRT
<213> ORGANISM: Artificial Sequence
<220> FEATURE:
<223> OTHER INFORMATION: anti-SAP Nanobody  702

<400> SEQUENCE: 23

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Val Asn
            20                  25                  30

Asp Met Gly Trp Tyr Arg Gln Ala Pro Gly Lys Gln Arg Glu Leu Val
        35                  40                  45

Ala Ile Ile Ile Thr Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Asp Phe Gly Thr Gly Pro Gly Arg Tyr Asp Tyr Trp Gly Gln Gly
            100                 105                 110

Thr Gln Val Thr Val Ser Ser
        115
```

<210> SEQ ID NO 24
<211> LENGTH: 121
<212> TYPE: PRT
<213> ORGANISM: Artificial Sequence
<220> FEATURE:
<223> OTHER INFORMATION: anti-SAP Nanobody 704

<400> SEQUENCE: 24

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Ile Ala Trp Val Arg Gln Ala Pro Gly Lys Gly Leu Glu Trp Val
        35                  40                  45

Ser Asp Ile Asn Ser Gly Gly Thr Asp Thr Ser Tyr Ala Ala Ala Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Ala Lys Ser Ala Gln Ser Tyr Phe His Ser Thr Phe Asp His Arg Gly
            100                 105                 110

Gln Gly Thr Gln Val Thr Val Ser Ser
        115                 120
```

<210> SEQ ID NO 25
<211> LENGTH: 119
<212> TYPE: PRT
<213> ORGANISM: Artificial Sequence
<220> FEATURE:
<223> OTHER INFORMATION: anti-SAP Nanobody 707

<400> SEQUENCE: 25

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Ala Met Gly Trp Tyr Arg Gln Ala Ser Gly Lys Gln Arg Glu Leu Val
        35                  40                  45

Ala Ala Ile Thr Ser Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Phe Gly Thr Gly Gly Arg Pro Tyr Asp Tyr Trp Gly Gln Gly
            100                 105                 110

Thr Gln Val Thr Val Ser Ser
        115
```

<210> SEQ ID NO 26
<211> LENGTH: 136
<212> TYPE: PRT
<213> ORGANISM: Bacillus anthracis

<400> SEQUENCE: 26

```
Met Gln Lys Ala Met Lys Glu Ile Lys Leu Glu Lys Thr Asn Val Ala
1               5                   10                  15
```

```
Leu Ser Thr Lys Asp Val Thr Asp Leu Lys Val Lys Ala Pro Val Leu
            20                  25                  30

Asp Gln Tyr Gly Lys Glu Phe Thr Ala Pro Val Thr Val Lys Val Leu
        35                  40                  45

Asp Lys Asp Gly Lys Glu Leu Lys Glu Gln Lys Leu Glu Ala Lys Tyr
    50                  55                  60

Val Asn Lys Glu Leu Val Leu Asn Ala Ala Gly Gln Glu Ala Gly Asn
65                  70                  75                  80

Tyr Thr Val Val Leu Thr Ala Lys Ser Gly Glu Lys Glu Ala Lys Ala
                85                  90                  95

Thr Leu Ala Leu Glu Leu Lys Ala Pro Gly Ala Phe Ser Lys Phe Glu
            100                 105                 110

Val Arg Gly Leu Glu Lys Glu Leu Asp Lys Tyr Val Thr Glu Glu Asn
        115                 120                 125

Gln Lys Asn Ala Met Thr Val Ser
    130                 135


<210> SEQ ID NO 27
<211> LENGTH: 862
<212> TYPE: PRT
<213> ORGANISM: Bacillus anthracis

<400> SEQUENCE: 27

Met Ala Lys Thr Asn Ser Tyr Lys Lys Val Ile Ala Gly Thr Met Thr
1               5                   10                  15

Ala Ala Met Val Ala Gly Ile Val Ser Pro Val Ala Ala Ala Gly Lys
            20                  25                  30

Ser Phe Pro Asp Val Pro Ala Gly His Trp Ala Glu Gly Ser Ile Asn
        35                  40                  45

Tyr Leu Val Asp Lys Gly Ala Ile Thr Gly Lys Pro Asp Gly Thr Tyr
    50                  55                  60

Gly Pro Thr Glu Ser Ile Asp Arg Ala Ser Ala Ala Val Ile Phe Thr
65                  70                  75                  80

Lys Ile Leu Asn Leu Pro Val Asp Glu Asn Ala Gln Pro Ser Phe Lys
                85                  90                  95

Asp Ala Lys Asn Ile Trp Ser Ser Lys Tyr Ile Ala Ala Val Glu Lys
            100                 105                 110

Ala Gly Val Val Lys Gly Asp Gly Lys Glu Asn Phe Tyr Pro Glu Gly
        115                 120                 125

Lys Ile Asp Arg Ala Ser Phe Ala Ser Met Leu Val Ser Ala Tyr Asn
    130                 135                 140

Leu Lys Asp Lys Val Asn Gly Glu Leu Val Thr Thr Phe Glu Asp Leu
145                 150                 155                 160

Leu Asp His Trp Gly Glu Glu Lys Ala Asn Ile Leu Ile Asn Leu Gly
                165                 170                 175

Ile Ser Val Gly Thr Gly Gly Lys Trp Glu Pro Asn Lys Ser Val Ser
            180                 185                 190

Arg Ala Glu Ala Ala Gln Phe Ile Ala Leu Thr Asp Lys Lys Tyr Gly
        195                 200                 205

Lys Lys Asp Asn Ala Gln Ala Tyr Val Thr Asp Val Lys Val Ser Glu
    210                 215                 220

Pro Thr Lys Leu Thr Leu Thr Gly Thr Gly Leu Asp Lys Leu Ser Ala
225                 230                 235                 240

Asp Asp Val Thr Leu Glu Gly Asp Lys Ala Val Ala Ile Glu Ala Ser
```

-continued

```
                245                 250                 255

Thr Asp Gly Thr Ser Ala Val Val Thr Leu Gly Gly Lys Val Ala Pro
            260                 265                 270

Asn Lys Asp Leu Thr Val Lys Val Lys Asn Gln Ser Phe Val Thr Lys
        275                 280                 285

Phe Val Tyr Glu Val Lys Lys Leu Ala Val Glu Lys Leu Thr Phe Asp
    290                 295                 300

Asp Asp Arg Ala Gly Gln Ala Ile Ala Phe Lys Leu Asn Asp Glu Lys
305                 310                 315                 320

Gly Asn Ala Asp Val Glu Tyr Leu Asn Leu Ala Asn His Asp Val Lys
                325                 330                 335

Phe Val Ala Asn Asn Leu Asp Gly Ser Pro Ala Asn Ile Phe Glu Gly
            340                 345                 350

Gly Glu Ala Thr Ser Thr Thr Gly Lys Leu Ala Val Gly Ile Lys Gln
        355                 360                 365

Gly Asp Tyr Lys Val Glu Val Gln Val Thr Lys Arg Gly Gly Leu Thr
    370                 375                 380

Val Ser Asn Thr Gly Ile Ile Thr Val Lys Asn Leu Asp Thr Pro Ala
385                 390                 395                 400

Ser Ala Ile Lys Asn Val Val Phe Ala Leu Asp Ala Asp Asn Asp Gly
                405                 410                 415

Val Val Asn Tyr Gly Ser Lys Leu Ser Gly Lys Asp Phe Ala Leu Asn
            420                 425                 430

Ser Gln Asn Leu Val Val Gly Glu Lys Ala Ser Leu Asn Lys Leu Val
        435                 440                 445

Ala Thr Ile Ala Gly Glu Asp Lys Val Val Asp Pro Gly Ser Ile Ser
    450                 455                 460

Ile Lys Ser Ser Asn His Gly Ile Ile Ser Val Val Asn Asn Tyr Ile
465                 470                 475                 480

Thr Ala Glu Ala Ala Gly Glu Ala Thr Leu Thr Ile Lys Val Gly Asp
                485                 490                 495

Val Thr Lys Asp Val Lys Phe Lys Val Thr Thr Asp Ser Arg Lys Leu
            500                 505                 510

Val Ser Val Lys Ala Asn Pro Asp Lys Leu Gln Val Val Gln Asn Lys
        515                 520                 525

Thr Leu Pro Val Thr Phe Val Thr Thr Asp Gln Tyr Gly Asp Pro Phe
    530                 535                 540

Gly Ala Asn Thr Ala Ala Ile Lys Glu Val Leu Pro Lys Thr Gly Val
545                 550                 555                 560

Val Ala Glu Gly Gly Leu Asp Val Val Thr Thr Asp Ser Gly Ser Ile
                565                 570                 575

Gly Thr Lys Thr Ile Gly Val Thr Gly Asn Asp Val Gly Glu Gly Thr
            580                 585                 590

Val His Phe Gln Asn Gly Asn Gly Ala Thr Leu Gly Ser Leu Tyr Val
        595                 600                 605

Asn Val Thr Glu Gly Asn Val Ala Phe Lys Asn Phe Glu Leu Val Ser
    610                 615                 620

Lys Val Gly Gln Tyr Gly Gln Ser Pro Asp Thr Lys Leu Asp Leu Asn
625                 630                 635                 640

Val Ser Thr Thr Val Glu Tyr Gln Leu Ser Lys Tyr Thr Ser Asp Arg
                645                 650                 655

Val Tyr Ser Asp Pro Glu Asn Leu Glu Gly Tyr Glu Val Glu Ser Lys
            660                 665                 670
```

```
Asn Leu Ala Val Ala Asp Ala Lys Ile Val Gly Asn Lys Val Val Val
        675                 680                 685

Thr Gly Lys Thr Pro Gly Lys Val Asp Ile His Leu Thr Lys Asn Gly
    690                 695                 700

Ala Thr Ala Gly Lys Ala Thr Val Glu Ile Val Gln Glu Thr Ile Ala
705                 710                 715                 720

Ile Lys Ser Val Asn Phe Lys Pro Val Gln Thr Glu Asn Phe Val Glu
                725                 730                 735

Lys Lys Ile Asn Ile Gly Thr Val Leu Glu Leu Glu Lys Ser Asn Leu
            740                 745                 750

Asp Asp Ile Val Lys Gly Ile Asn Leu Thr Lys Glu Thr Gln His Lys
        755                 760                 765

Val Arg Val Val Lys Ser Gly Ala Glu Gln Gly Lys Leu Tyr Leu Asp
    770                 775                 780

Arg Asn Gly Asp Ala Val Phe Asn Ala Gly Asp Val Lys Leu Gly Asp
785                 790                 795                 800

Val Thr Val Ser Gln Thr Ser Asp Ser Ala Leu Pro Asn Phe Lys Ala
                805                 810                 815

Asp Leu Tyr Asp Thr Leu Thr Thr Lys Tyr Thr Asp Lys Gly Thr Leu
            820                 825                 830

Val Phe Lys Val Leu Lys Asp Lys Asp Val Ile Thr Ser Glu Ile Gly
        835                 840                 845

Ser Gln Ala Val His Val Asn Val Leu Asn Asn Pro Asn Leu
    850                 855                 860


<210> SEQ ID NO 28
<211> LENGTH: 665
<212> TYPE: PRT
<213> ORGANISM: Artificial Sequence
<220> FEATURE:
<223> OTHER INFORMATION: EA1 amino acid sequence w/o SLH domain with
      N-terminal His6 tag and 10 aa-linker

<400> SEQUENCE: 28

Met His His His His His His Ile Thr Ser Leu Tyr Lys Lys Ala Gly
1               5                   10                  15

Met Ala Tyr Val Thr Asp Val Lys Val Ser Glu Pro Thr Lys Leu Thr
            20                  25                  30

Leu Thr Gly Thr Gly Leu Asp Lys Leu Ser Ala Asp Asp Val Thr Leu
        35                  40                  45

Glu Gly Asp Lys Ala Val Ala Ile Glu Ala Ser Thr Asp Gly Thr Ser
    50                  55                  60

Ala Val Val Thr Leu Gly Gly Lys Val Ala Pro Asn Lys Asp Leu Thr
65                  70                  75                  80

Val Lys Val Lys Asn Gln Ser Phe Val Thr Lys Phe Val Tyr Glu Val
                85                  90                  95

Lys Lys Leu Ala Val Glu Lys Leu Thr Phe Asp Asp Asp Arg Ala Gly
            100                 105                 110

Gln Ala Ile Ala Phe Lys Leu Asn Asp Glu Lys Gly Asn Ala Asp Val
        115                 120                 125

Glu Tyr Leu Asn Leu Ala Asn His Asp Val Lys Phe Val Ala Asn Asn
    130                 135                 140

Leu Asp Gly Ser Pro Ala Asn Ile Phe Glu Gly Gly Glu Ala Thr Ser
145                 150                 155                 160

Thr Thr Gly Lys Leu Ala Val Gly Ile Lys Gln Gly Asp Tyr Lys Val
```

-continued

```
                165                 170                 175

Glu Val Gln Val Thr Lys Arg Gly Gly Leu Thr Val Ser Asn Thr Gly
            180                 185                 190

Ile Ile Thr Val Lys Asn Leu Asp Thr Pro Ala Ser Ala Ile Lys Asn
        195                 200                 205

Val Val Phe Ala Leu Asp Ala Asp Asn Asp Gly Val Val Asn Tyr Gly
    210                 215                 220

Ser Lys Leu Ser Gly Lys Asp Phe Ala Leu Asn Ser Gln Asn Leu Val
225                 230                 235                 240

Val Gly Glu Lys Ala Ser Leu Asn Lys Leu Val Ala Thr Ile Ala Gly
                245                 250                 255

Glu Asp Lys Val Val Asp Pro Gly Ser Ile Ser Ile Lys Ser Ser Asn
            260                 265                 270

His Gly Ile Ile Ser Val Val Asn Asn Tyr Ile Thr Ala Glu Ala Ala
        275                 280                 285

Gly Glu Ala Thr Leu Thr Ile Lys Val Gly Asp Val Thr Lys Asp Val
    290                 295                 300

Lys Phe Lys Val Thr Thr Asp Ser Arg Lys Leu Val Ser Val Lys Ala
305                 310                 315                 320

Asn Pro Asp Lys Leu Gln Val Val Gln Asn Lys Thr Leu Pro Val Thr
                325                 330                 335

Phe Val Thr Thr Asp Gln Tyr Gly Asp Pro Phe Gly Ala Asn Thr Ala
            340                 345                 350

Ala Ile Lys Glu Val Leu Pro Lys Thr Gly Val Val Ala Glu Gly Gly
        355                 360                 365

Leu Asp Val Val Thr Thr Asp Ser Gly Ser Ile Gly Thr Lys Thr Ile
    370                 375                 380

Gly Val Thr Gly Asn Asp Val Gly Glu Gly Thr Val His Phe Gln Asn
385                 390                 395                 400

Gly Asn Gly Ala Thr Leu Gly Ser Leu Tyr Val Asn Val Thr Glu Gly
                405                 410                 415

Asn Val Ala Phe Lys Asn Phe Glu Leu Val Ser Lys Val Gly Gln Tyr
            420                 425                 430

Gly Gln Ser Pro Asp Thr Lys Leu Asp Leu Asn Val Ser Thr Thr Val
        435                 440                 445

Glu Tyr Gln Leu Ser Lys Tyr Thr Ser Asp Arg Val Tyr Ser Asp Pro
    450                 455                 460

Glu Asn Leu Glu Gly Tyr Glu Val Glu Ser Lys Asn Leu Ala Val Ala
465                 470                 475                 480

Asp Ala Lys Ile Val Gly Asn Lys Val Val Val Thr Gly Lys Thr Pro
                485                 490                 495

Gly Lys Val Asp Ile His Leu Thr Lys Asn Gly Ala Thr Ala Gly Lys
            500                 505                 510

Ala Thr Val Glu Ile Val Gln Glu Thr Ile Ala Ile Lys Ser Val Asn
        515                 520                 525

Phe Lys Pro Val Gln Thr Glu Asn Phe Val Glu Lys Lys Ile Asn Ile
    530                 535                 540

Gly Thr Val Leu Glu Leu Glu Lys Ser Asn Leu Asp Asp Ile Val Lys
545                 550                 555                 560

Gly Ile Asn Leu Thr Lys Glu Thr Gln His Lys Val Arg Val Val Lys
                565                 570                 575

Ser Gly Ala Glu Gln Gly Lys Leu Tyr Leu Asp Arg Asn Gly Asp Ala
            580                 585                 590
```

```
Val Phe Asn Ala Gly Asp Val Lys Leu Gly Asp Val Thr Val Ser Gln
        595                 600                 605

Thr Ser Asp Ser Ala Leu Pro Asn Phe Lys Ala Asp Leu Tyr Asp Thr
    610                 615                 620

Leu Thr Thr Lys Tyr Thr Asp Lys Gly Thr Leu Val Phe Lys Val Leu
625                 630                 635                 640

Lys Asp Lys Asp Val Ile Thr Ser Glu Ile Gly Ser Gln Ala Val His
                645                 650                 655

Val Asn Val Leu Asn Asn Pro Asn Leu
            660                 665


<210> SEQ ID NO 29
<211> LENGTH: 1985
<212> TYPE: DNA
<213> ORGANISM: Artificial Sequence
<220> FEATURE:
<223> OTHER INFORMATION: E.coli codon usage optimized B.anthracis sterne
      EA1 coding sequence of EA1

<400> SEQUENCE: 29

atgcatcatc atcatcatca tattaccagc ctgtataaaa aagcgggcat ggcctacgta     60

accgatgtaa aagtgtccga gcctaccaag ctcacgctca cgggtacggg tctggataaa    120

ctctctgcgg acgacgttac gctcgaaggt gataaggcgg tggccattga ggcaagcacc    180

gacggtacgt ctgcagtcgt gaccctcggc ggtaaggttg ccccaaataa ggatctcacc    240

gtgaaagtta agaatcagtc cttcgttact aagtttgttt acgaggtaaa gaagctggcg    300

gtagaaaagc tgacctttga tgatgaccgc gcaggccaag ccatcgcatt caaactcaat    360

gatgaaaaag gcaacgcgga tgtagagtac ctgaacctcg cgaatcatga cgtaaaattc    420

gttgcaaaca acctcgatgg cagccctgca aatatctttg aaggtggcga ggcgacctcc    480

acgaccggta aactcgcggt cggcatcaaa caaggtgact ataaagtcga agtacaagta    540

actaagcgtg gtggcctgac tgtctctaac acgggcatta ttactgtgaa gaatctcgac    600

acgcctgcaa gcgcaatcaa gaacgtagtt tttgctctcg atgcggacaa tgacggcgtg    660

gttaactacg gctctaaact gtctggtaag gatttcgcac tgaacagcca aaacctcgtg    720

gttggcgaga aagcctctct caataagctc gtagcgacta tcgcaggcga agacaaagta    780

gtggatcctg gttccatcag cattaaaagc tctaatcatg gtattatctc cgtagtgaat    840

aactacatca cggcggaggc agccggcgaa gctacgctga cgattaaagt aggcgacgtg    900

accaaagacg ttaaattcaa agttacgacg gattcccgta aactggtgtc tgtgaaagca    960

aacccggaca aactgcaagt tgtacagaat aaaaccctgc cagttacgtt tgtgactacc   1020

gatcagtacg gcgacccatt cggcgcgaac actgctgcga tcaaggaggt actgccgaaa   1080

accggtgtgg tagcagaggg tggtctcgac gtggtcacca cggactctgg ttctattggt   1140

acgaagacga ttggcgtgac gggtaatgac gtgggcgaag gtaccgttca cttccagaat   1200

ggtaatggtg ccacgctggg tagcctgtat gtaaacgtta ccgagggcaa tgtggccttc   1260

aagaatttcg aactcgtttc taaggtaggc cagtatggtc agtctccgga taccaaactc   1320

gacctcaacg tcagcaccac cgtcgaatac caactcagca aatacacgtc tgatcgtgta   1380

tactctgatc cagaaaacct ggagggctat gaagtggagt ctaagaacct ggcagtagcg   1440

gacgcgaaaa tcgtgggtaa taaggtggtg gttacgggca aaaccccagg caaggtcgac   1500

atccacctca ctaagaatgg cgctaccgct ggtaaagcga ctgttgagat tgtgcaggaa   1560
```

-continued

```
acgattgcca tcaagtctgt taatttcaaa ccagtacaga cggagaactt tgtagagaaa   1620

aagatcaaca tcggcactgt gctggagctg gaaaagagca atctggatga catcgttaaa   1680

ggtattaatc tcacgaaaga aacccagcat aaagtgcgtg ttgttaaatc tggtgcggaa   1740

cagggtaagc tgtacctgga ccgtaacggc gatgctgttt tcaatgcggg cgatgttaag   1800

ctgggtgatg tgactgtttc tcagacctct gactctgcgc tgcctaactt caaggcggac   1860

ctctatgata ccctgaccac taagtatacc gataagggca ctctcgtgtt taaggttctg   1920

aaggacaagg acgtcatcac gagcgaaatt ggctctcagg cagtgcacgt taatgtactg   1980

aataa                                                               1985
```

<210> SEQ ID NO 30
<211> LENGTH: 64
<212> TYPE: DNA
<213> ORGANISM: Artificial Sequence
<220> FEATURE:
<223> OTHER INFORMATION: Primer

<400> SEQUENCE: 30

```
ggggacaagt ttgtacaaaa aagcaggctt cgaaggagat agaaccatgt ccgcgaaggc     60

cgtg                                                                  64
```

<210> SEQ ID NO 31
<211> LENGTH: 69
<212> TYPE: DNA
<213> ORGANISM: Artificial Sequence
<220> FEATURE:
<223> OTHER INFORMATION: Primer

<400> SEQUENCE: 31

```
ggggaccact ttgtacaaga aagctgggtc ctagtgatgg tgatggtgat gacccactgc     60

tacctcagt                                                             69
```

<210> SEQ ID NO 32
<211> LENGTH: 67
<212> TYPE: DNA
<213> ORGANISM: Artificial Sequence
<220> FEATURE:
<223> OTHER INFORMATION: Primer

<400> SEQUENCE: 32

```
ggggacaagt ttgtacaaaa aagcaggctt cgaaggagat agaaccatgc agaaagcgat     60

gaaggaa                                                               67
```

<210> SEQ ID NO 33
<211> LENGTH: 69
<212> TYPE: DNA
<213> ORGANISM: Artificial Sequence
<220> FEATURE:
<223> OTHER INFORMATION: Primer

<400> SEQUENCE: 33

```
ggggaccact ttgtacaaga aagctgggtc ctagtgatgg tgatggtgat ggcctggagc     60

cttcagctc                                                             69
```

<210> SEQ ID NO 34
<211> LENGTH: 67
<212> TYPE: DNA
<213> ORGANISM: Artificial Sequence
<220> FEATURE:
<223> OTHER INFORMATION: Primer

<400> SEQUENCE: 34
ggggacaagt ttgtacaaaa aagcaggctt cgaaggagat agaaccatgg ccaaaggcct 60
ggcagta 67

<210> SEQ ID NO 35
<211> LENGTH: 51
<212> TYPE: DNA
<213> ORGANISM: Artificial Sequence
<220> FEATURE:
<223> OTHER INFORMATION: Primer

<400> SEQUENCE: 35
ggggaccact ttgtacaaga aagctgggtc ctagtgatgg tgatggtgat g 51

<210> SEQ ID NO 36
<211> LENGTH: 129
<212> TYPE: PRT
<213> ORGANISM: Artificial Sequence
<220> FEATURE:
<223> OTHER INFORMATION: anti-Sap Nanobody 679

<400> SEQUENCE: 36

Gln Val Gln Leu Val Glu Ser Gly Gly Gly Leu Val Gln Ala Gly Gly
1 5 10 15

Ser Leu Arg Leu Ser Cys Ala Ala Ser Gly Ser Ile Phe Arg Val Asn
20 25 30

Ala Met Gly Trp Tyr Arg Gln Val Pro Gly Lys Gln Arg Glu Leu Val
35 40 45

Ala His Ile Thr Ser Gly Gly Ser Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys His
85 90 95

Ala Asp Leu Gly Thr Gly Pro Leu Pro Tyr Asp Tyr Trp Gly Gln Gly
100 105 110

Thr Gln Val Thr Val Ser Ser His His His His His His Glu Pro Glu
115 120 125

Ala

<210> SEQ ID NO 37
<211> LENGTH: 129
<212> TYPE: PRT
<213> ORGANISM: Artificial Sequence
<220> FEATURE:
<223> OTHER INFORMATION: anti-Sap Nanobody 687

<400> SEQUENCE: 37

Gln Val Gln Leu Val Glu Ser Gly Gly Gly Leu Val Arg Ala Gly Gly
1 5 10 15

Ser Leu Arg Leu Ser Cys Ala Ala Ser Gly Ser Ile Phe Arg Ile Asn
20 25 30

Ala Met Gly Trp Tyr Arg Gln Ala Pro Gly Lys Gln Arg Glu Leu Val
35 40 45

Ala Ala Ile Thr Ser Gly Gly Ser Thr Asn Tyr Ala Asp Ser Val Lys
50 55 60

Gly Arg Phe Thr Ile Ser Arg Asp Asn Ala Lys Arg Thr Val Tyr Leu
65 70 75 80

```
Gln Met Asn Ser Leu Lys Pro Glu Asp Thr Ala Val Tyr Tyr Cys Asn
                85                  90                  95

Ala Asp Phe Ser Thr Gly Trp Ala Pro Tyr Asp Tyr Trp Gly Gln Gly
            100                 105                 110

Thr Gln Val Thr Val Ser Ser His His His His His His Glu Pro Glu
        115                 120                 125

Ala


<210> SEQ ID NO 38
<211> LENGTH: 133
<212> TYPE: PRT
<213> ORGANISM: Artificial Sequence
<220> FEATURE:
<223> OTHER INFORMATION: anti-Sap Nanobody  695

<400> SEQUENCE: 38

Gln Val His Leu Val Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Phe Met Gly Trp Tyr Arg Gln Ala Pro Gly Lys Gln Arg Glu Leu Val
        35                  40                  45

Ala Gly Ile Thr Ser Gly Ser Asn Thr Asn Tyr Ala Thr Asn Tyr Ala
    50                  55                  60

Asp Ser Val Lys Gly Arg Phe Thr Ile Ala Arg Asp Lys Ser Lys Asn
65                  70                  75                  80

Thr Val Tyr Leu Gln Met Asn Ser Leu Lys Pro Glu Asp Thr Ala Val
                85                  90                  95

Tyr Tyr Cys Asn Ala Asp Phe Gly Thr Ser Gly Arg Pro Tyr Phe Tyr
            100                 105                 110

Trp Gly Gln Gly Thr Gln Val Thr Val Ser Ser His His His His His
        115                 120                 125

His Glu Pro Glu Ala
    130


<210> SEQ ID NO 39
<211> LENGTH: 135
<212> TYPE: PRT
<213> ORGANISM: Artificial Sequence
<220> FEATURE:
<223> OTHER INFORMATION: anti-Sap Nanobody  703

<400> SEQUENCE: 39

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Gly Gly Lys Tyr Gly Ser Thr Trp Tyr Gly Gln Ile Glu Tyr
            100                 105                 110
```

Asp Tyr Trp Gly Gln Gly Thr Gln Val Thr Val Ser Ser His His His
115 120 125

His His His Glu Pro Glu Ala
130 135

<210> SEQ ID NO 40
<211> LENGTH: 137
<212> TYPE: PRT
<213> ORGANISM: Artificial Sequence
<220> FEATURE:
<223> OTHER INFORMATION: Non-Sap binding control Nb 11

<400> SEQUENCE: 40

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Phe
20 25 30

Ala Met Gly Trp Phe Arg Leu Ala Pro Gly Ala Glu Arg Glu Phe Val
35 40 45

Gly Ala Ile Ser Arg Ser Gly Asp Ser Thr Tyr Tyr Ala Glu Ser Val
50 55 60

Lys Gly Arg Phe Thr Ile Ser Arg Asp Asn Ala Met Asn Thr Val Tyr
65 70 75 80

Leu Gln Met Asn Asn Leu Lys Pro Glu Asp Thr Ala Val Tyr Tyr Cys
85 90 95

Ala Ala Glu Glu Ala Tyr Gly Ser Met Leu Arg Leu Arg Gln Ala Arg
100 105 110

Phe Tyr Asp Tyr Trp Gly Gln Gly Thr Gln Val Thr Val Ser Ser His
115 120 125

His His His His His Glu Pro Glu Ala
130 135

<210> SEQ ID NO 41
<211> LENGTH: 12
<212> TYPE: PRT
<213> ORGANISM: Artificial Sequence
<220> FEATURE:
<223> OTHER INFORMATION: Nb 694 CDR3

<400> SEQUENCE: 41

Gly Lys Tyr Gly Arg Thr Trp Tyr Gly Gln Leu Glu
1 5 10

<210> SEQ ID NO 42
<211> LENGTH: 6
<212> TYPE: PRT
<213> ORGANISM: Artificial Sequence
<220> FEATURE:
<223> OTHER INFORMATION: Nb684,683,688,692,702,707 CDR1

<400> SEQUENCE: 42

Ser Gly Ser Ile Phe Arg
1 5

<210> SEQ ID NO 43
<211> LENGTH: 11
<212> TYPE: PRT
<213> ORGANISM: Artificial Sequence
<220> FEATURE:
<223> OTHER INFORMATION: Nb684 CDR3

<400> SEQUENCE: 43

Leu Gly Thr Gly Gly Arg Ser Tyr Asp Tyr Trp
1 5 10

<210> SEQ ID NO 44
<211> LENGTH: 11
<212> TYPE: PRT
<213> ORGANISM: Artificial Sequence
<220> FEATURE:
<223> OTHER INFORMATION: Nb683 CDR3

<400> SEQUENCE: 44

Phe Ser Thr Gly Trp Ala Pro Tyr Asp Tyr Trp
1 5 10

<210> SEQ ID NO 45
<211> LENGTH: 12
<212> TYPE: PRT
<213> ORGANISM: Artificial Sequence
<220> FEATURE:
<223> OTHER INFORMATION: Nb688 CDR3

<400> SEQUENCE: 45

Phe Ser Thr Val Arg Glu Arg Arg Tyr Asp Tyr Trp
1 5 10

<210> SEQ ID NO 46
<211> LENGTH: 10
<212> TYPE: PRT
<213> ORGANISM: Artificial Sequence
<220> FEATURE:
<223> OTHER INFORMATION: Nb692 CDR3

<400> SEQUENCE: 46

Phe Gly Thr Leu Gly Arg Tyr Asp Tyr Trp
1 5 10

<210> SEQ ID NO 47
<211> LENGTH: 11
<212> TYPE: PRT
<213> ORGANISM: Artificial Sequence
<220> FEATURE:
<223> OTHER INFORMATION: Nb702 CDR3

<400> SEQUENCE: 47

Phe Gly Thr Gly Pro Gly Arg Tyr Asp Tyr Trp
1 5 10

<210> SEQ ID NO 48
<211> LENGTH: 11
<212> TYPE: PRT
<213> ORGANISM: Artificial Sequence
<220> FEATURE:
<223> OTHER INFORMATION: Nb707 CDR3

<400> SEQUENCE: 48

Phe Gly Thr Gly Gly Arg Pro Tyr Asp Tyr Trp
1 5 10

<210> SEQ ID NO 49
<211> LENGTH: 13
<212> TYPE: PRT
<213> ORGANISM: Artificial Sequence
<220> FEATURE:
<223> OTHER INFORMATION: Nb704 CDR3

<400> SEQUENCE: 49

Ser Ala Gln Ser Tyr Phe His Ser Thr Phe Asp His Arg
1 5 10

<210> SEQ ID NO 50
<211> LENGTH: 6
<212> TYPE: PRT
<213> ORGANISM: Artificial Sequence
<220> FEATURE:
<223> OTHER INFORMATION: Sap epitope in D1

<400> SEQUENCE: 50

Tyr Ser Asn Leu Ala Ala
1 5

<210> SEQ ID NO 51
<211> LENGTH: 18
<212> TYPE: PRT
<213> ORGANISM: Artificial Sequence
<220> FEATURE:
<223> OTHER INFORMATION: Sap epitope in D2

<400> SEQUENCE: 51

Ala Leu Gln Phe Thr Val Lys Asp Glu Asn Gly Thr Glu Val Val Ser
1 5 10 15

Pro Glu

<210> SEQ ID NO 52
<211> LENGTH: 6
<212> TYPE: PRT
<213> ORGANISM: Artificial Sequence
<220> FEATURE:
<223> OTHER INFORMATION: paratope in CDR1

<400> SEQUENCE: 52

Ser Gly Ser Ile Phe Arg
1 5

<210> SEQ ID NO 53
<211> LENGTH: 4
<212> TYPE: PRT
<213> ORGANISM: Artificial Sequence
<220> FEATURE:
<223> OTHER INFORMATION: paratope in CDR3

<400> SEQUENCE: 53

Tyr Asp Tyr Trp
1

<210> SEQ ID NO 54
<211> LENGTH: 10
<212> TYPE: PRT
<213> ORGANISM: Artificial Sequence
<220> FEATURE:
<223> OTHER INFORMATION: His6-EPEA tag

<400> SEQUENCE: 54

His His His His His His Glu Pro Glu Ala
1 5 10

COMPOUNDS TO INHIBIT BACTERIAL S-LAYER PROTEIN ASSEMBLY

FIELD OF THE INVENTION

The present invention relates to the field of bacterial Surface (S)-layer proteins, in particular to compounds capable of disrupting the bacterial S-Layer, specifically the S-Layer of *Bacillus anthracis*. More particularly, the invention provides for single domain antibodies for diagnosis and treatment of infection caused by pathogens with an S-Layer, in particular of *Bacillus anthracis* infection. The invention relates to S-Layer protein binding agents inhibiting bacterial growth and interrupting S-Layer assembly, useful in the treatment of bacterial infection, more specifically treatment of anthrax disease.

BACKGROUND

Anthrax is primarily a disease of sheep, cattle, horses, goats and swine caused by *Bacillus anthracis*, a gram-positive spore-forming aerobic rod that produces exotoxins. The organism is transmitted to humans by inoculation of broken skin or mucous membranes causing cutaneous or gastrointestinal infections, or by inhalation, causing pulmonary infection. Anthrax is also a rare occupational disease of farmers, veterinarians and wool workers. *B. anthracis* is designated as category A bio-threat agent because of the ease of formulating the spores for use as a weapon of war and the persistence of the spores in the environment. Therefore, the bioterrorism threat from inhaled *B. anthracis* spores has increased the need for effective treatments and preventions of this deadly disease. Inhalational anthrax is the most deadly form of the disease. The incubation period ranges from 1-43 days, with a mean incubation period of 16 days. The standard course of antibiotic treatment post-exposure is 60 days, but the length of treatment for full protection is currently unknown. The mean duration of non-specific prodromal symptoms is 4.1 days, and the mean duration of the fulminant phase is 1.1 days, after which the death rate approaches 100% in the absence of treatment. *B. anthracis* multiplies rapidly and secretes the anthrax toxins, consisting of three components: protective antigen (PA), lethal factor (LF) and oedema factor (EF). PA is a receptor-binding moiety that generates a protein-conducting channel for delivering EF and LF into the cytosol to exert their cytotoxic effects. LF, which combines with PA to form lethal toxin (LT), is a $Zn^{2+}$-dependent metalloproteinase that cleaves and inactivates mitogen-activated protein kinase kinases (MAPKKs or MEKs). The events leading to death from anthrax in humans are twofold. First there is a disabling of the innate immune system by LT by infecting macrophages in which the bacteria are able to survive and divide. In a second, systemic stage, the bacteria disseminate in the body with higher levels of toxin produced in circulation wherein LT targets cardiomyocytes and smooth muscle cells eventually producing lethality of the patient.

Victims of inhalational anthrax do not experience significant symptoms until a late stage in the disease when they are close to sepsis and toxaemia. Antibiotic treatment is largely ineffective at the symptomatic stage in preventing death, in part because antibiotics do not target the anthrax toxins. To be maximally effective, antibiotic therapy must be initiated within hours of exposure to aerosolized *B. anthracis* spores, prior to the onset of symptoms. However, in the event of mass exposure to anthrax spores, as could occur in a bioterrorist attack, treatment would most likely not begin until 3 to 6 days post-exposure, on average, owing to the length of time required to identify potential victims and distribute stockpiled medication. At that point, upwards of 25% of anthrax cases following exposure to a lethal dose of anthrax spores would fail to be prevented by antibiotics alone. Anthrax vaccines, which over the course of several weeks stimulate the immune system to mount a protective response against PA, are effective in pre-exposure prophylaxis, and can afford some protection from breakthrough infection arising from germination of residual spores after withdrawal of antibiotic therapy, Anthrax vaccines are ineffective when used alone in the post-exposure setting. Another method for preventing anthrax is vaccination but several doses of the vaccine are needed to confer protection and furthermore also annual boosts are required.

*B. anthracis*, has a dynamic cell surface with a complex composition. On top of a thick peptidoglycan cell wall, the vegetative surface of this bacillus is covered by one of two distinct proteinaceous paracrystalline arrays, known as Surface layer (S-Layer). During infection, prior to its escape from the macrophage or at the site of spore contact and germination, *B. anthracis* cells become fully virulent by the expression of toxins and the very weakly immunogenic poly-γ-D-glutamic acid (PDGA) capsule that is covalently attached to the peptidoglycan layer. Once the capsule is assembled the PDGA chains will pass through the S-Layer arrays masking the S-Layer proteins (SLPs). The capsulated *B. anthracis* prevents itself from further phagocytosis (Preisz 1909; Zwartouw and Smith 1956; Makino et al. 1989), resulting in a systemic spread (sepsis) that ultimately leads to the death of the host. Although *B. anthracis*' SLPs are the primary contact area between the bacterium and its environment, very little is known about their structure and function. S-Layers compose the cell surface of myriad of bacteria and near all Archea and where present, they may comprise 5-10% of the total cell protein production (Sàra and Sleytr, 2000). Today, only very limited S-Layer protein's structure has been resolved (Baranova et al., 2014; Bharat et al., 2017). S-Layers have been proposed to serve as exoskeleton, protection against harmful environments, molecular sieve for nutrient uptake and a contact zone with the extracellular environment, including host cells in case of pathogenic bacteria (Gerbino et al. 2015).

Earlier studies have shown that *B. anthracis*' S-Layer has a peculiar dynamic composition in response to developmental signals. In rich media, two mutually exclusive S-Layers sequentially appear at the cell surface in a growth phase-dependent manner: the Sap exponential layer and EA1 stationary layer (Mignot et al. 2002). In lab anaerobic conditions, in a growth medium that induce toxins production, the biphasic expression pattern has been seen altered and the EA1 seems to be the major component of the S-Layer (Mignot et al. 2003). Deletion strains of either S-Layer proteins are viable in lab condition, but have never been tested in the context of infection. Although viable in vitro, a sap deletion mutant shows cell division defects, increasing cell size to 20 times that of wild type (Etienne-Toumelin et al 1995), making this protein a promising target to fight anthrax disease. Many questions remain with respect to the how and when of S-Layer remodelling during infection. What is the implication of either S-Layer in *B. anthracis* virulence and susceptibility to host responses? Is the S-Layer and its dynamic composition essential for acute anthrax disease? Is there a role for S-Layer fragments found in *B. anthracs* spore coats? How conserved is the S-Layer protein function among pathogenic bacteria in relation to infections?

To date, the self-assembling characteristic of Sap and EA1 SLP proteins has hampered their ease of handling under non-denaturing conditions and has hitherto proven prohibitive for structural and biophysical characterization. Sap-specific conventional mouse antibodies (150 kDa) have been used in the past, mostly as diagnostic markers (e.g. U.S. Pat. No. 7,393,647B2 by Valkirs et al.; Zhang et al., 2008; Sharma et al., 2016), as well as EA1-specific ScFvs (WO2007/007086A2), though not with the potential to affect S-Layer assembly. To date, the use of such antibodies for in vivo treatment to protect against *B. anthracis* infection has not been reported or shown.

In this context, there is a clear need and opportunity in obtaining detailed insight into the S-Layer protein function in bacterial pathogen infection, more particularly the Sap protein function of *Bacillus anthracis*. Revealing an essential role for SLPs in bacterial pathogen infection would allow to identify novel agents specifically affecting S-Layer protein polymerization and assembly to disturb and disrupt S-Layer formation during bacterial growth and infection.

SUMMARY OF THE INVENTION

*B. anthracis* is a potent biological warfare agent that causes anthrax upon ingestion, inhalation or cutaneous exposure. By further studying the Surface (S)-layer proteins (SLPs), novel routes for infection treatments were encountered in the studies leading to this invention. The self-assembling characteristic of *B. anthracis* Sap SLP proteins have complicated over the years the structural analysis of this S-Layer protein that was therefore so far impossible (Etienne-Toumelin et al., 1995). To overcome the SLP protein self-assembling or polymerization issue, Nanobodies® (Nbs) were successfully identified, produced and applied as a bio-tool to control Sap polymerization. Using these Nbs as crystallization aid, crystallization and structure determination of Sap was accomplished, which is remarkable as it is only the third S-Layer protein structure ever solved. Thanks to this result a novel class of SLPs that adopts a new calcium-independent mechanism of assembly was unveiled. Excitingly, the Nbs that were selected to inhibit the in vitro polymerization of Sap (defined herein as "$Nbs^{SAI}$" representing the collection, mixture ('cocktail') of Nbs that is capable of inhibiting Sap polymerization, more specifically, the group of Nbs (Nb683, Nb688, Nb692, Nb702, Nb704, and Nb707; also named herein $Nb^{AF683}$, $Nb^{AF688}$, $Nb^{AF692}$, $Nb^{AF702}$, $Nb^{AF704}$, and $Nb^{AF707}$, resp.) could, when applied in vivo, strip away or disrupt the Sap protein S-Layer and perturb *B. anthracis* cell morphology. This surprising finding was further confirmed by time-lapse experiments showing a severe reduction in growth rate of cells treated with Sap Nbs. Encouraged by these novel findings, further investigation even revealed that anti-Sap single domain antibodies, antibody fragments or Sap binding agents with S-Layer assembly inhibitory activity are capable of disintegrating such bacterial S-Layers thereby forming a new promising therapeutic route to cure pathogen infections of S-Layer containing bacteria, such as *B. anthracis*, allowing to fight anthrax disease. The invention hence provides for a bio-tool to perturb the in vivo *B. anthracis* S-Layer assembly, even to disrupt said S-Layer, which can be considered as a novel methodology delivering novel compounds to induce a non-genetically S-Layer depletion with huge therapeutic potential to treat anthrax, or to improve or combine this novel methodology with existing therapeutic strategies. The invention further reveals that SLPs of other S-Layer-containing bacterial pathogens may be targeted in a similar way, thereby covering a broader mechanism to in fact inhibit S-Layer assembly or disrupt S-Layers as a novel way to prevent, treat, or cure pathogenic infections such as anthrax. The present invention is based on the determination of the crystal structure of monomeric Sap, in interaction with Nbs, leading to the novel feature that a number of Nbs were found to inhibit the in vitro and in vivo Sap polymerization or assembly, and that such S-Layer inhibitory Nbs by disintegrating the S-Layer also affect *B. anthracis* growth and provide a successful therapeutic treatment in a mouse model of anthrax disease. Mice with an ongoing anthrax infection treated with Nbs inhibiting Sap S-Layer assembly resulted in the clearance of an ongoing *B. anthracis* infection and the cure of lethal anthrax disease.

The first aspect of the invention relates to a compound specifically binding to a bacterial S-Layer protein (SLP) which prevents its polymerization or assembly, and moreover, which disrupts or disintegrates the bacterial S-Layer. In a specific embodiment, said bacterial S-Layer protein is the *B. anthracis* Surface array protein (Sap). In one embodiment said compound binds the monomeric Sap proteins for prevention of polymerization. In another embodiment said compound binds multimeric Sap protein, preventing further oligomerization or polymerization, even disrupting or breaking down said S-Layer. In another embodiment said compound alternatively binds the Sap proteins of pre-existing S-Layers leading to disintegration of said S-Layer.

In one embodiment, said compound specifically binding to bacterial SLP, for preventing its assembly or polymerization and for disintegrating the S-Layer, is a small compound, or is a peptide, or is a peptidomimetic. In another embodiment, said compound of the present invention is an active antibody fragment and/or antibody mimetic. Specific embodiments relate to compounds binding and inhibiting Sap polymerization as a single-domain antibody, most specifically, as an immunoglobulin single variable domain, and/or a Nanobody.

Other embodiments disclose compounds of the present invention wherein the bacterial S-Layer protein is derived from an S-Layer-containing bacterium, or more specifically from a pathogen selected from the list of *Bacillus* species (*B. anthracis, B. cereus, B. thuringiensis*), *Clostridium difficile, Paenibacillus* larvae, *Caphylobacteri fetus, Campylobacter rectus, Tannerella forsythia, Aeromonas hydrophila, Rickettsia prowazekii, Rickettsia rickettsia, Rickettsia typhi, Serratia marcescens, Aeromonas salmonicida* and *Lactobacillus acidophilus*. In another particular embodiment, said compound of the present invention specifically binds to a protein comprising SEQ ID NO:6, SEQ ID NO:7, SEQ ID NO:9, and/or SEQ ID NO:11, presenting the Sap structural protein domain 1, domain 2, domain 4 and/or domain 6 as provided by the 3D-structure, respectively. More preferably, the compound of the present invention binds to a protein comprising SEQ ID NO:6 and/or SEQ ID NO:7, representing domains 1 and 2 or the Sap protein respectively. An alternative embodiment relates to a compound of the present invention which binds to the Sap protein epitopes comprising amino acid residues 221-222,271 to 276, and residues 316-320, and 328-333 of SEQ ID NO:1.

In another specific embodiment, said compound of the present invention is an active antibody fragment or single domain antibody, with an immunoglobulin fold, wherein the immunoglobulin domain comprises an amino acid sequence that comprises 4 framework regions (FR) and 3 complementarity determining regions (CDR) according to the formula FR1-CDR1-FR2-CDR2-FR3-CDR3-FR4 (1); and wherein CDR1 comprises the sequence SGSIFR, and CDR3 comprises the sequence YDYW, which are both contributing to the Sap binding site. In a particular embodiment, the Nanobody blocking Sap polymerization and disrupting the *Bacillus* S-Layer comprises SEQ ID NO: 20, SEQ ID NO: 21, SEQ ID NO: 22, SEQ ID NO: 23, SEQ ID NO: 24, or SEQ ID NO: 25, which represent Nanobody amino acid sequences identified to act as Sap assembly inhibitors, able to disintegrate the S-Layer and to affect cell growth and morphology of *B. anthracis*. In an alternative embodiment, the Nanobody of the invention is a humanized variant of any of the Nanobodies comprising SEQ ID NO: 20, SEQ ID NO: 21, SEQ ID NO: 22, SEQ ID NO: 23, SEQ ID NO: 24, or SEQ ID NO: 25, which encode $Nb^{AF683}$, $Nb^{AF688}$, $Nb^{AF692}$, $Nb^{AF702}$, $Nb^{AF704}$, and $Nb^{AF707}$, respectively. A further embodiment relates to the nanobody of the invention, wherein said nanobody is coupled to a half-life extension, in particular a serum albumin binding nanobody.

A further aspect of the invention relates to a composition or pharmaceutical composition, comprising or consisting of a mixture of compounds, wherein said mixture contains or comprises at least one or more compounds of the invention. In particular said composition may comprise a mixture of single domain antibodies specifically binding to the bacterial S-Layer protein to disintegrate said S-Layer. Said mixture of compounds may in addition to the at least one compound of the invention binding the SLP of a pathogen, also comprise a compound specifically binding to or targeting a toxin of the same pathogen.

Another aspect of the invention relates to a compound or a pharmaceutical composition of the present invention for use as a medicine or medicament. More particularly, one embodiment relates to said compound or a pharmaceutical composition of the invention for use to treat *B. anthracis* infection. In another aspect, said compound of the invention is for use in diagnosis of bacterial infection, specifically for bacterial pathogens containing an S-Layer, and even more particularly for *B. anthracis* infection.

In a final aspect of the invention, a compound of the invention may be used as a tool in structural analysis, comprising crystallography, cryo-EM, or as purification aid in stabilizing SLPs.

DESCRIPTION OF THE FIGURES

The drawings described are only schematic and are non-limiting. In the drawings, the size of some of the elements may be exaggerated and not drawn on scale for illustrative purposes.

For detailed information, see also Example 1.

Figure 2:
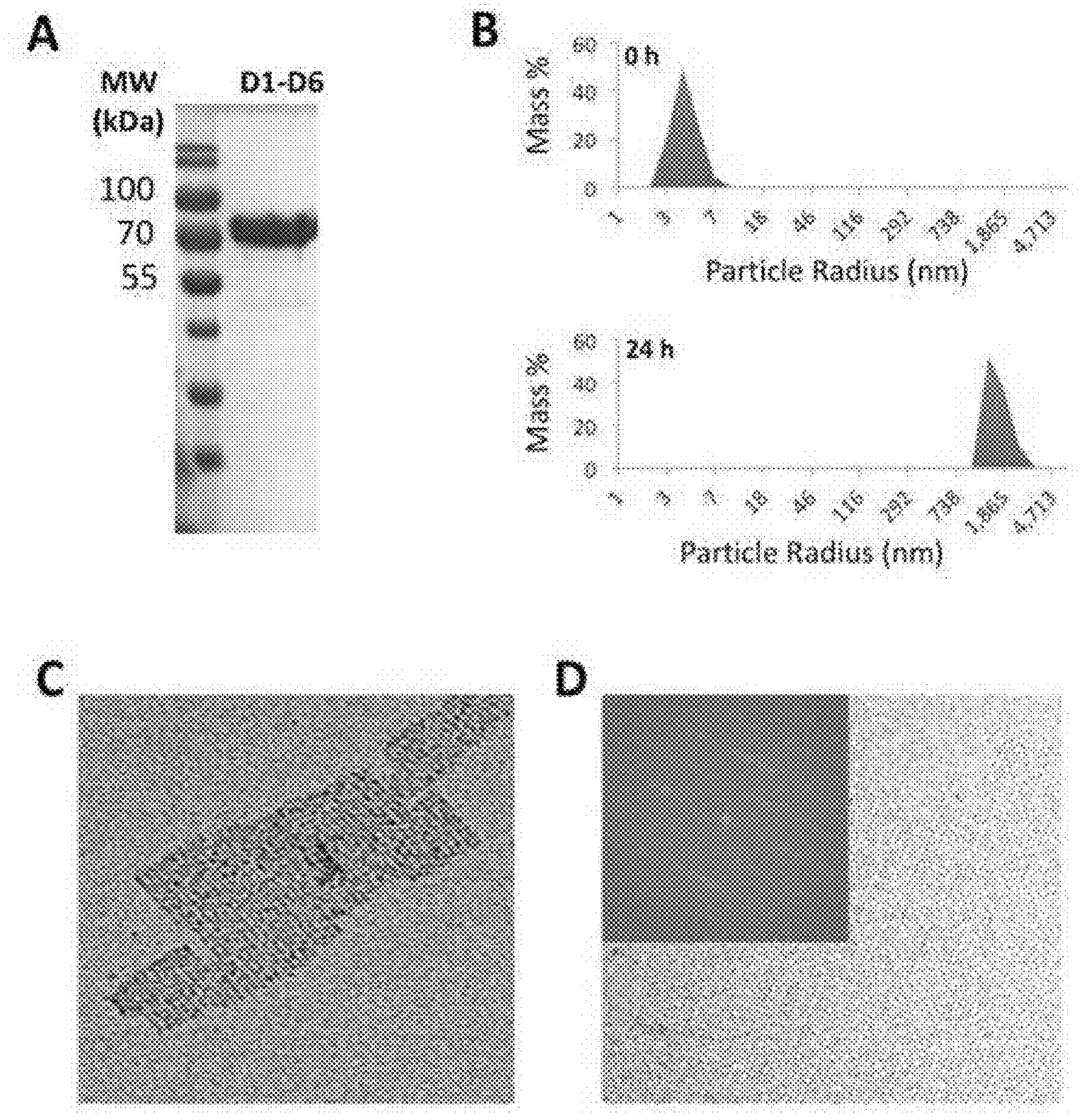

FIG. 2. Recombinant production and self-assembly of *B. anthracis* Sap.

For detailed information, see also Example 1.

Figure 3:
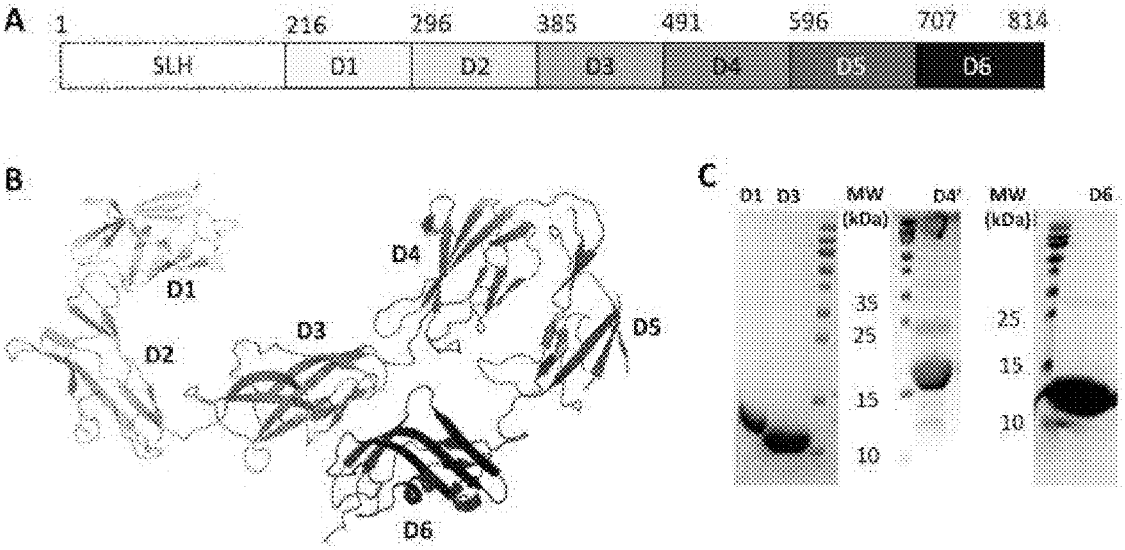

FIG. 3. Domain organization and X-ray structure of *B. anthracis* Sap.

For detailed information, see also Example 2.

Figure 4:
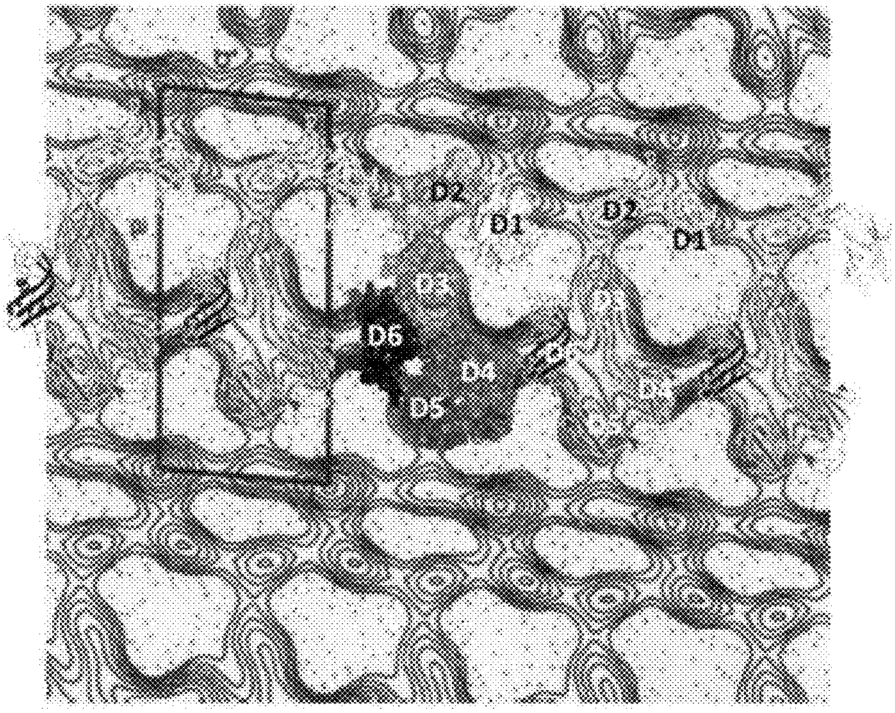

FIG. 4. Structural model of *B. anthracis* Sap S-Layer lattice.

For detailed information, see also Example 2.

Figure 5:
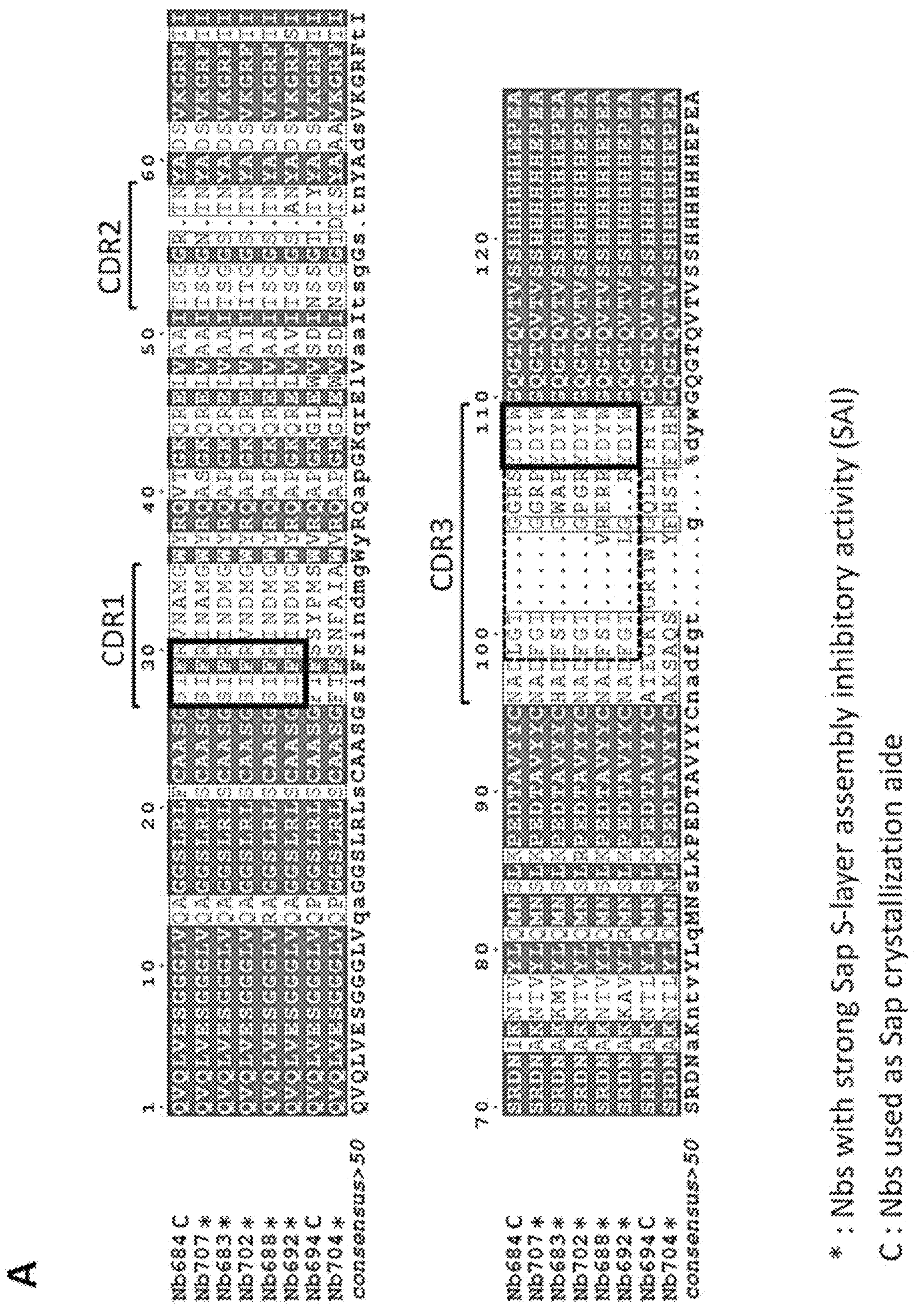

FIG. 5. Nanobodies used as crystallization aid or S-Layer assembly inhibitor of *B. anthracis* Sap.

For detailed information, see also Example 3.

Figure 6:
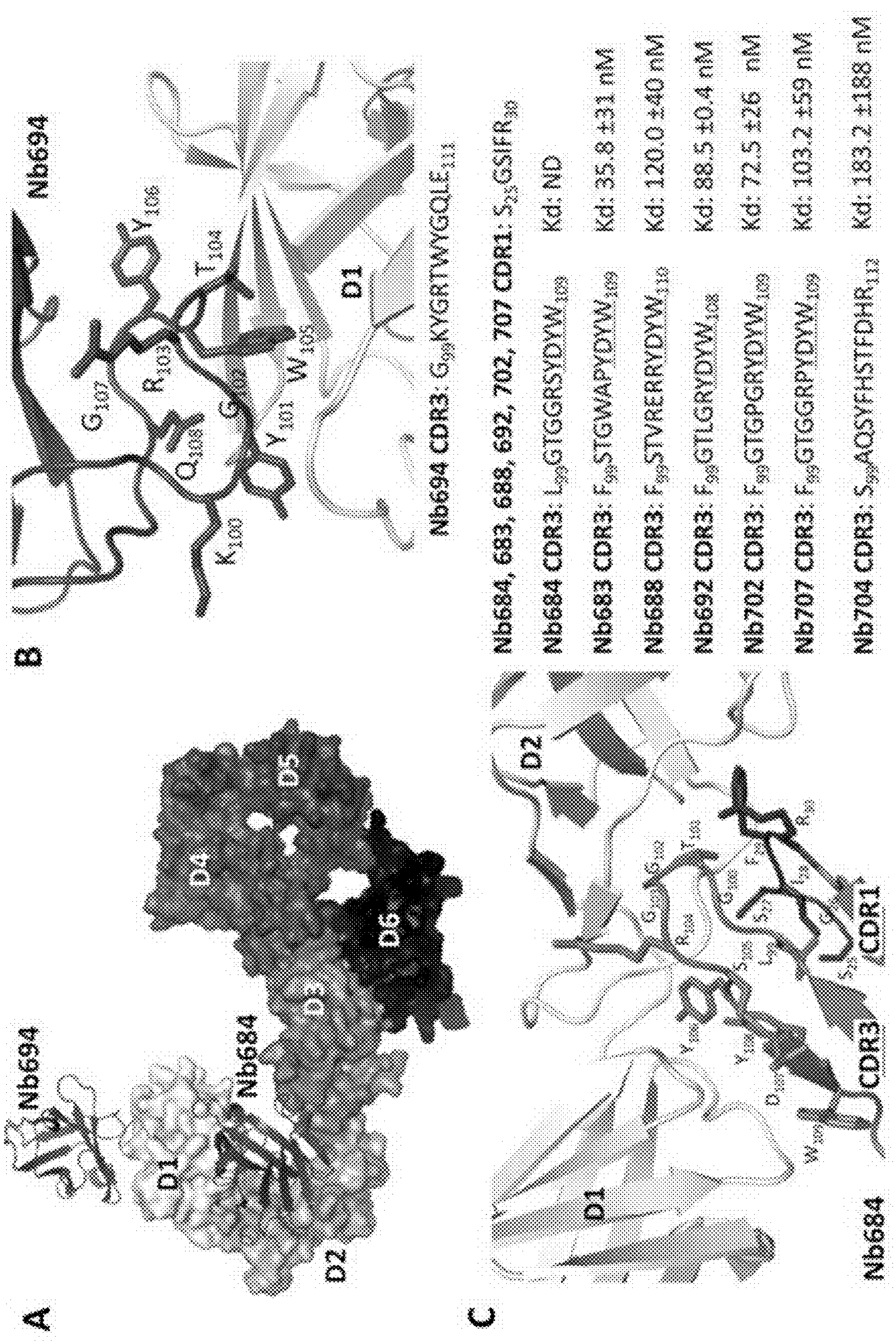

FIG. 6. Nanobodies binding to *B. anthracis* Sap.

For detailed information, see also Example 3.

Figure 7:
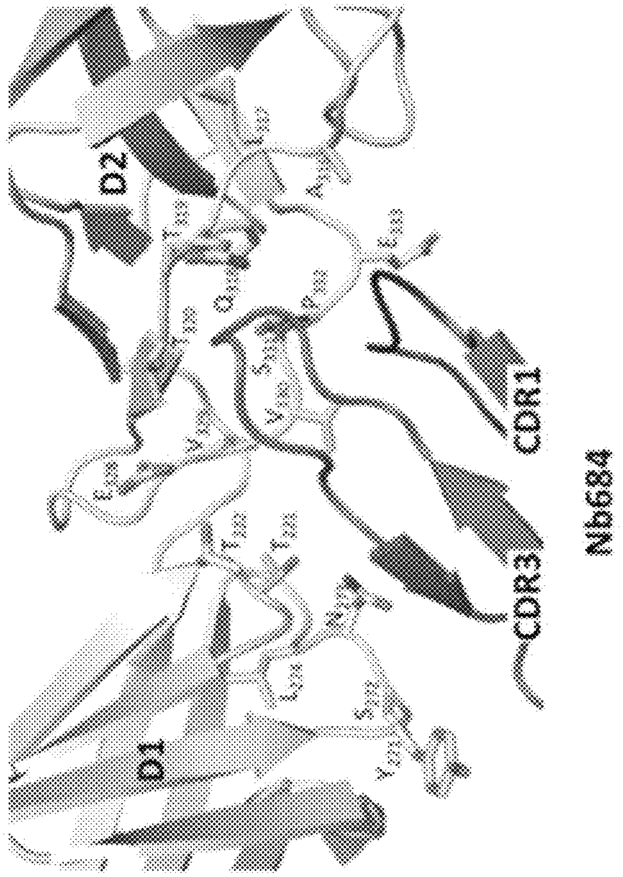

FIG. 7. Nanobody binding interactions in *B. anthracis* $Sap^{216-814}$.

For detailed information, see also Example 3.

Figure 8:
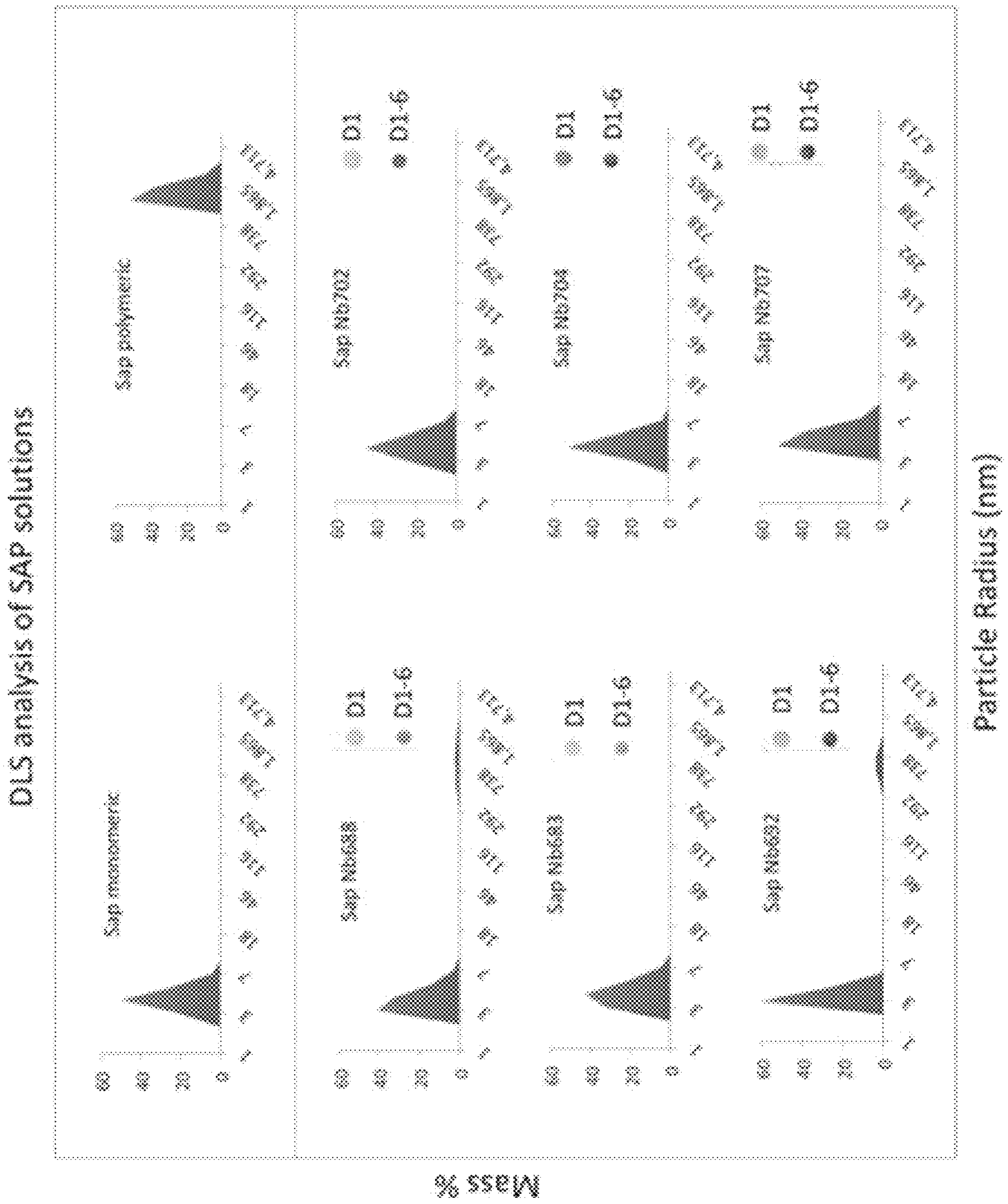

FIG. 8. Anti-Sap Nanobodies act as Sap polymerization inhibitors.

For detailed information, see also Example 3.

Figure 9:
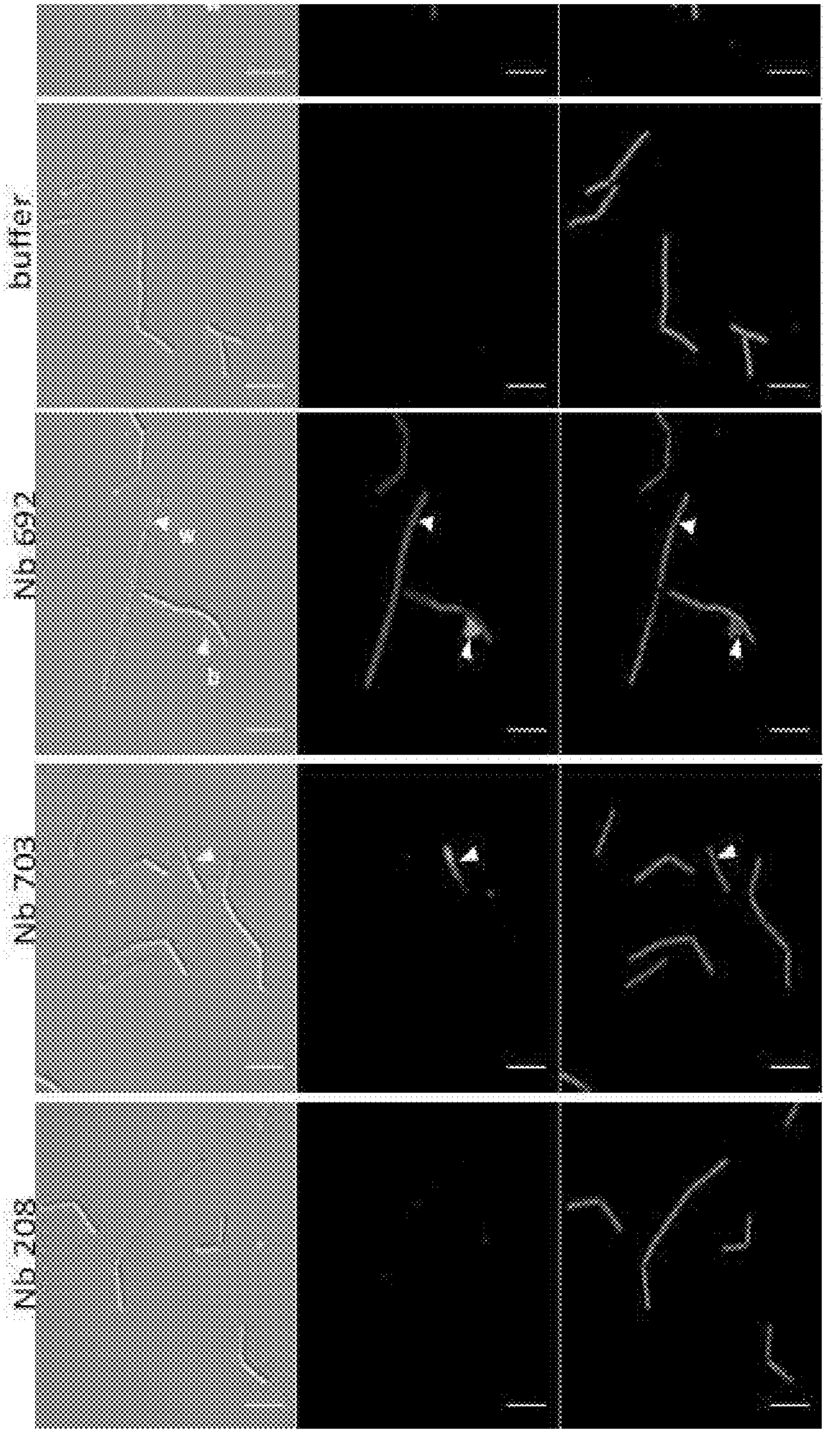

FIG. 9. Nanobodies with S-Layer assembly inhibitor activity affect *B. anthracis* cell morphology.

For detailed information, see also Example 4.

Figure 10:
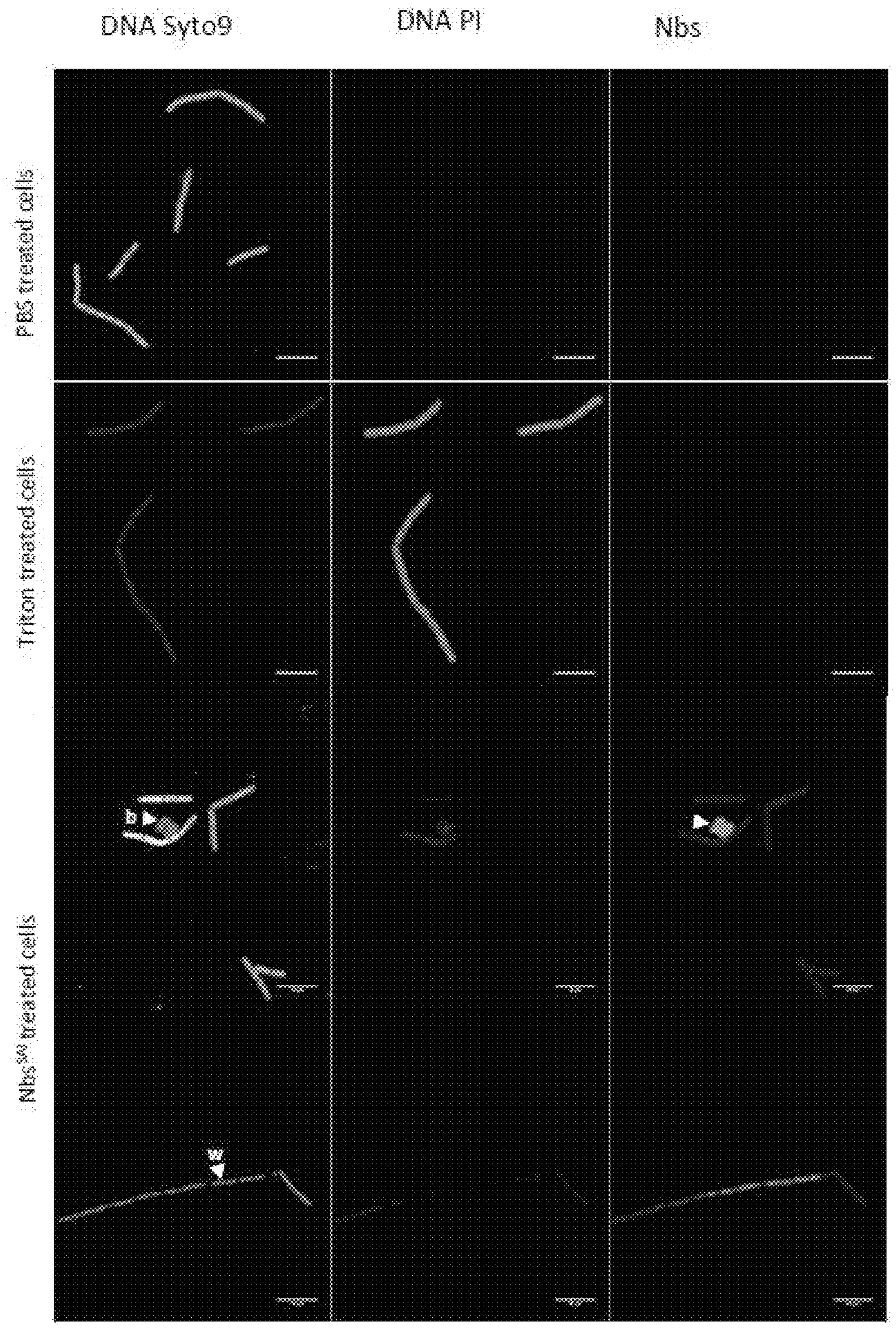

FIG. 10. $Nbs^{SAI}$ *B. anthracis* affected cells are negative for propidium iodide staining.

For detailed information, see also Example 4.

Figure 11:
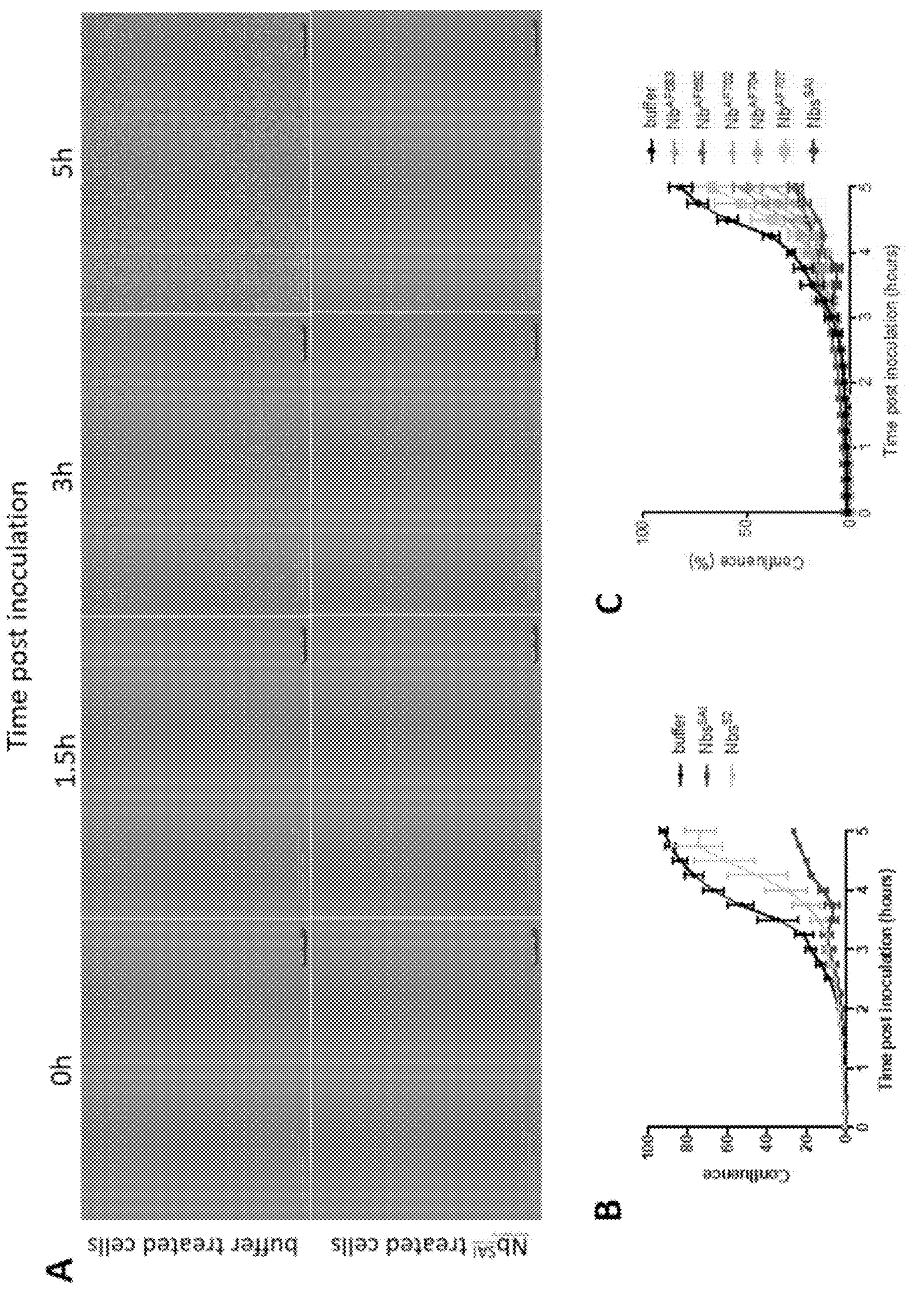

FIG. 11. Nanobodies with Sap S-Layer assembly inhibitory activity attenuate *B. anthracis* growth.

For detailed information, see also Example 4.

Figure 12:
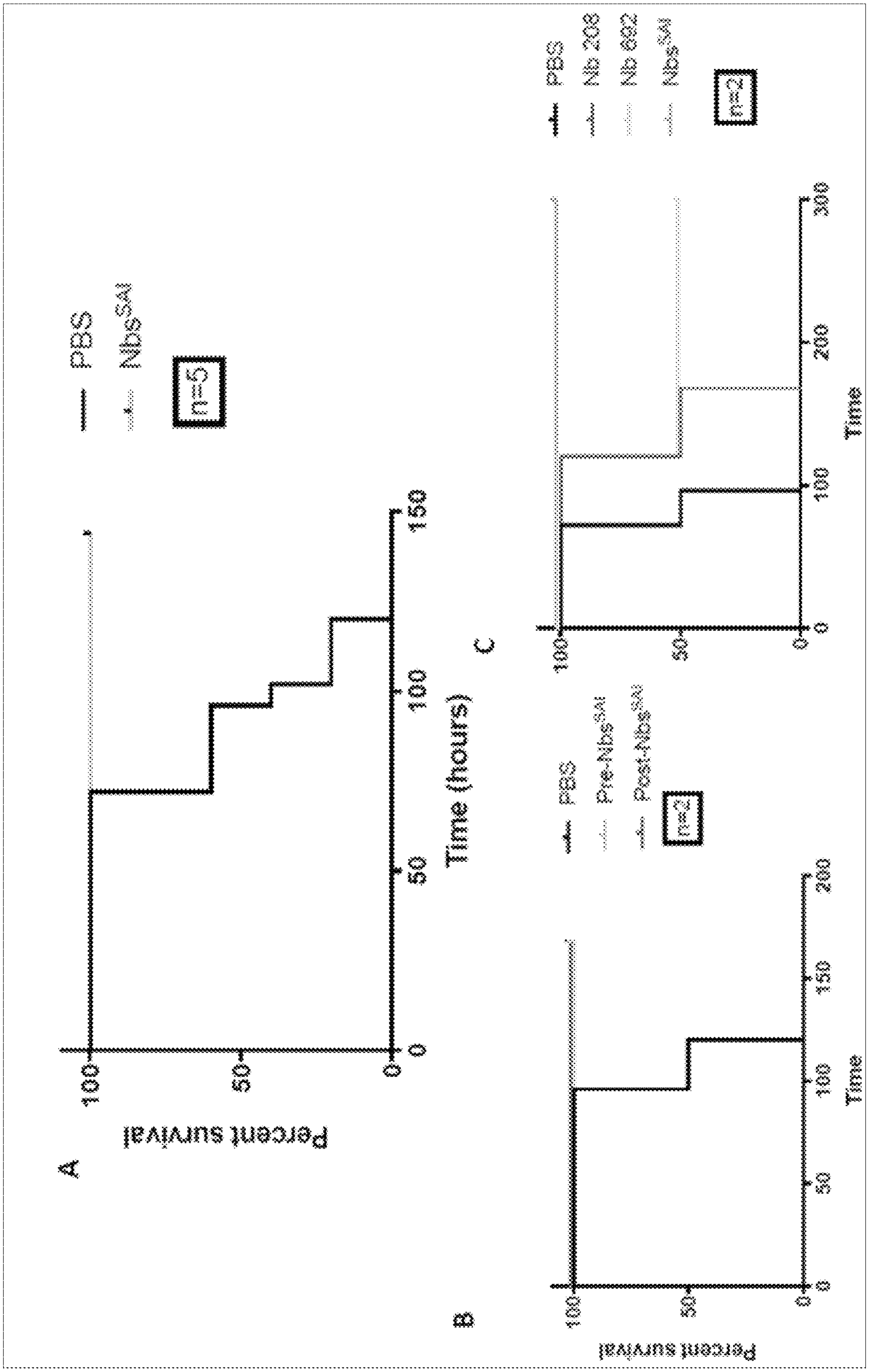

FIG. 12. Nanobodies with Sap S-Layer assembly inhibitory activity clear *B. anthracis* infection in a mouse model curing mice from lethal anthrax.

For detailed information, see also Example 5.

Figure 13:
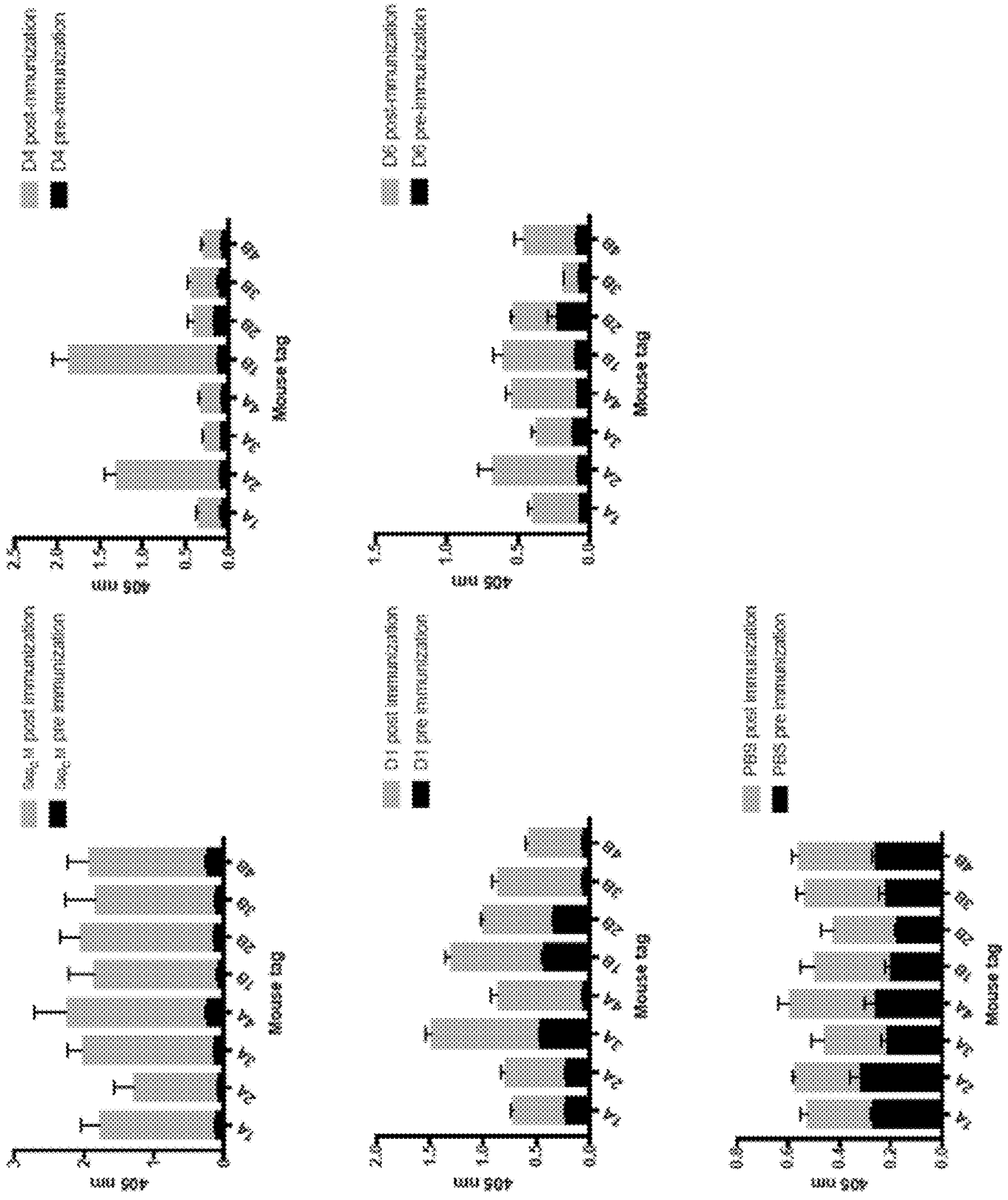
Figure 13:
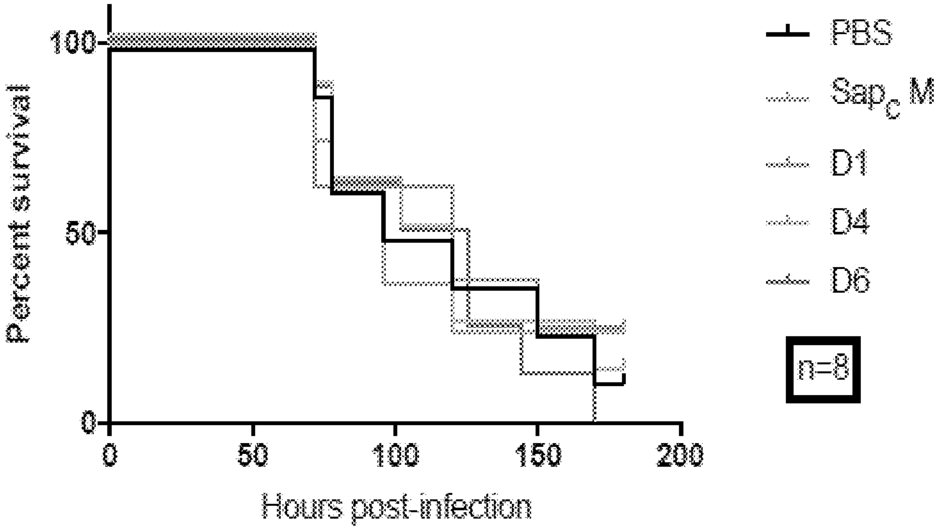

FIG. 13. Evaluation of Monomeric Sap216-814, D1, D4 and D6 protective effect against anthrax in mice.

For detailed information, see also Example 6.

Figure 14:
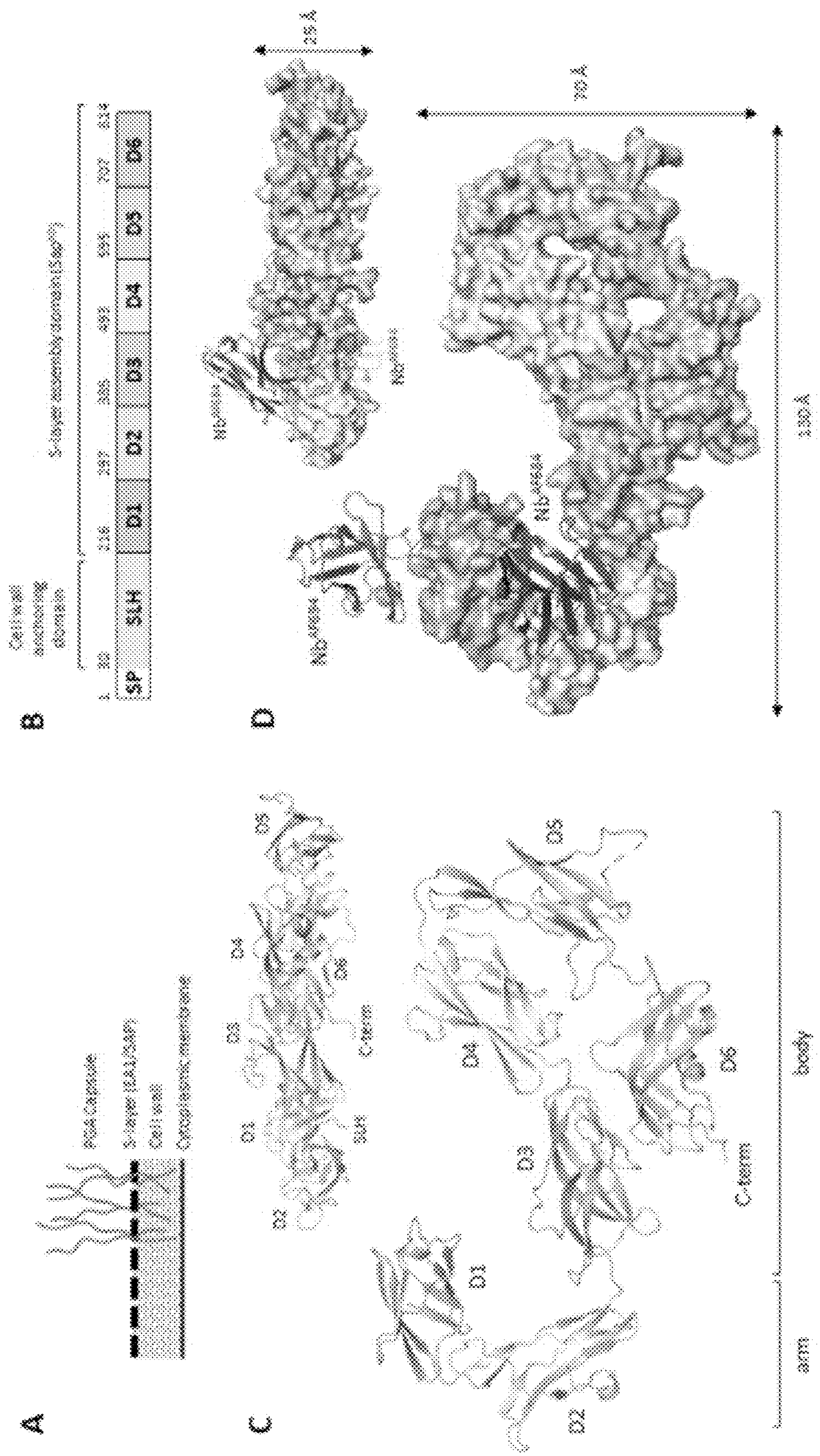

FIG. 14. X-ray structure of *B. anthracis* $Sap^{AD}$ (=$Sap^{216-814}$).

(a) Schematic representation of the cell envelope organization of *B. anthracis* in the absence or presence of the polyglutamate (PGA) capsule (left- and right, respectively). (b) Schematic domain organization of *B. anthracis* Sap. The N-terminal ~215 residues consist of a signal peptide (SP) and a pseudorepeat of three SLH domains that form a cell wall anchoring domain. The Sap S-Layer assembly region ($Sap^{AD}$) comprises six independent domains (labelled D1-D6) as revealed in this study. (c) Ribbon representation of the X-ray structure of $Sap^{AD}$ (residues 216-814) comprises six independent β-domains (D1-D6) that assembly into a flat, tile-like unit. (d) Surface representation of the $Sap^{AD}$ X-ray structure with $Nb^{AF694}$ and $Nb^{AF684}$ shown as ribbon representation; these Nbs, used as crystallization aides, bind two independent epitopes in D1 ($Nb^{AF694}$) and the D1-D2 interface ($Nb^{AF684}$).

Figure 15:
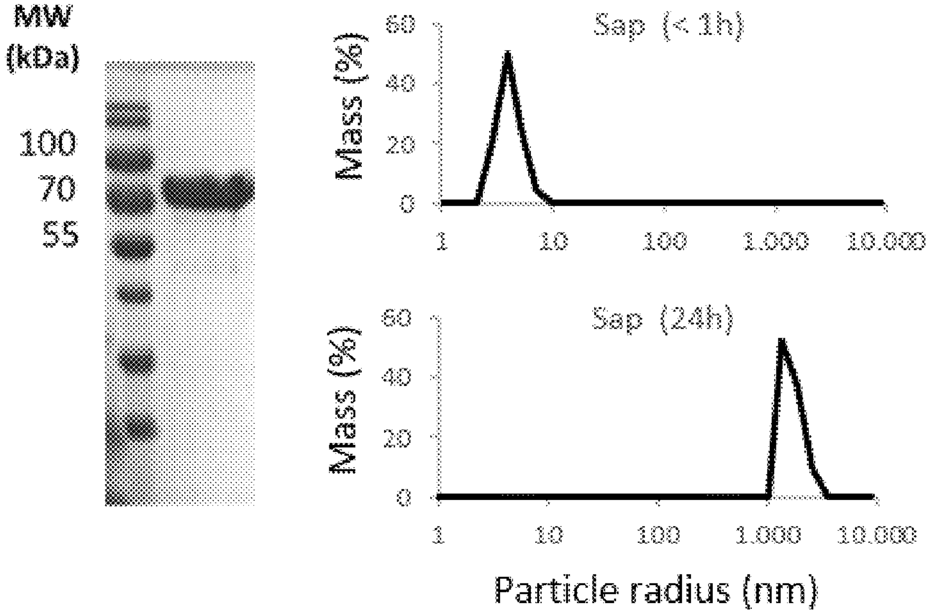
Figure 15:
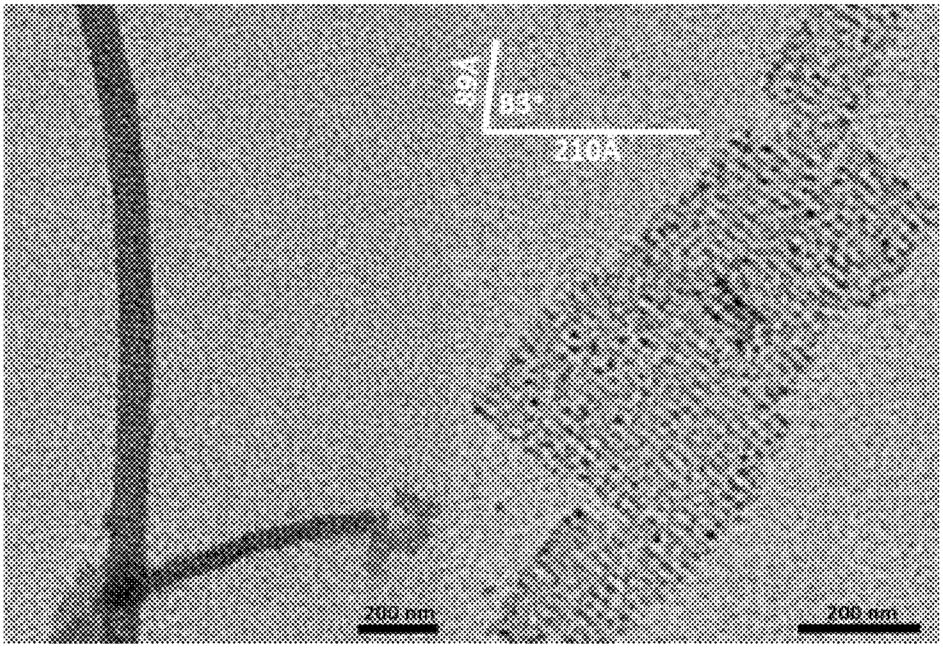
Figure 15:
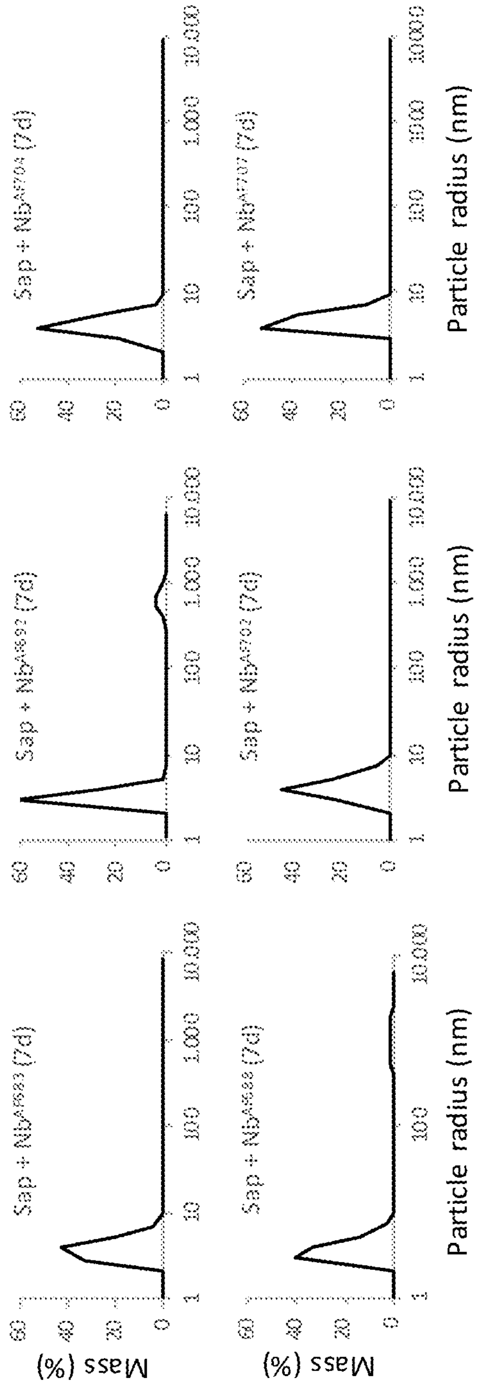
Figure 15:
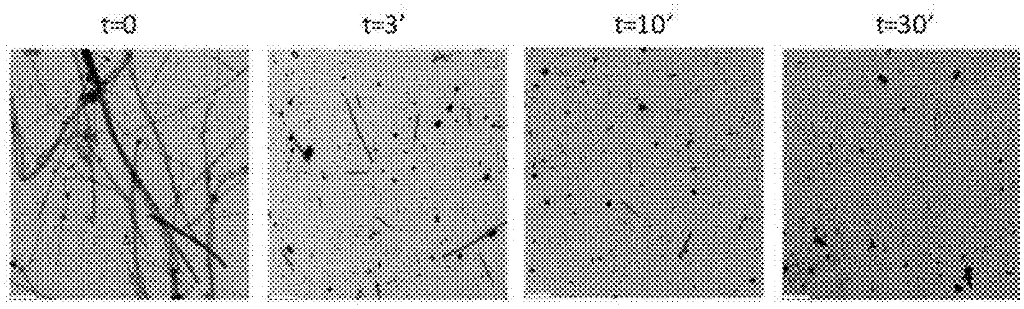
Figure 15:
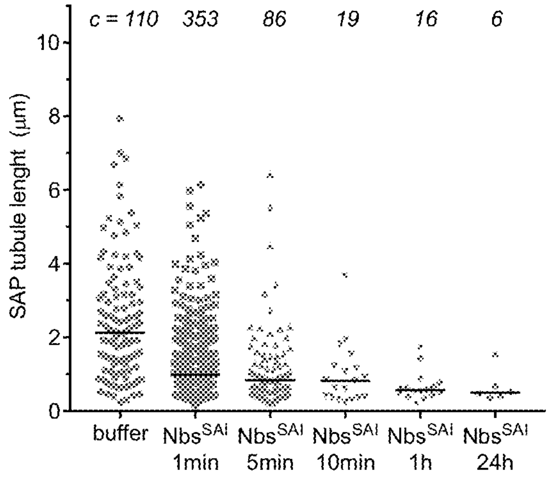
Figure 15:
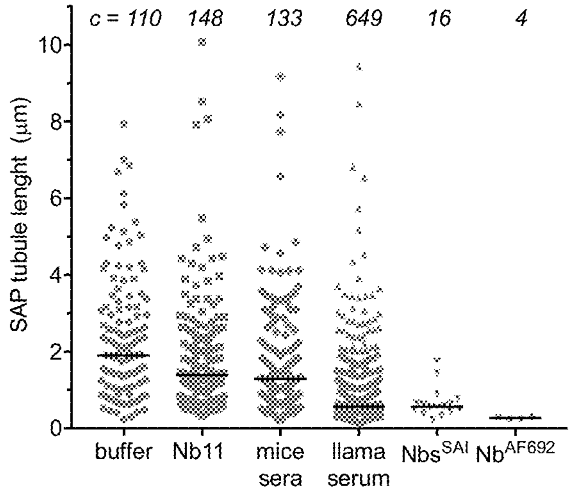
Figure 15:
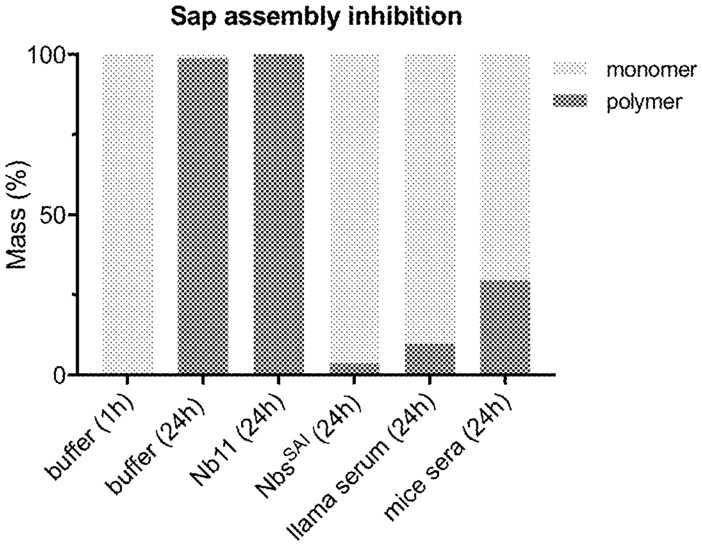
Figure 15:
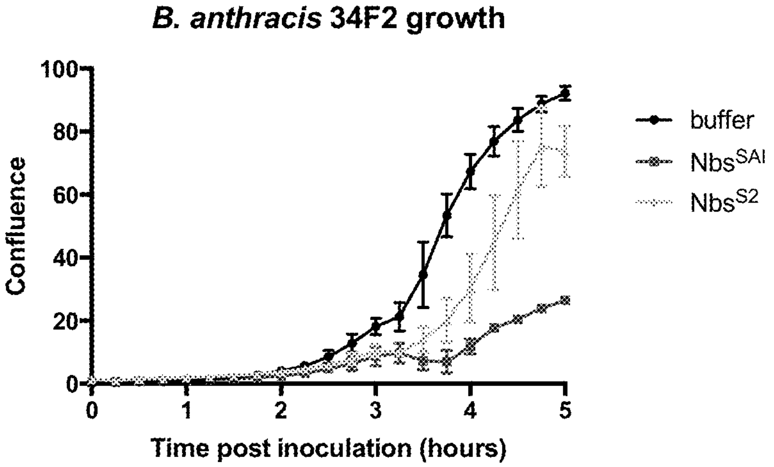
Figure 15:
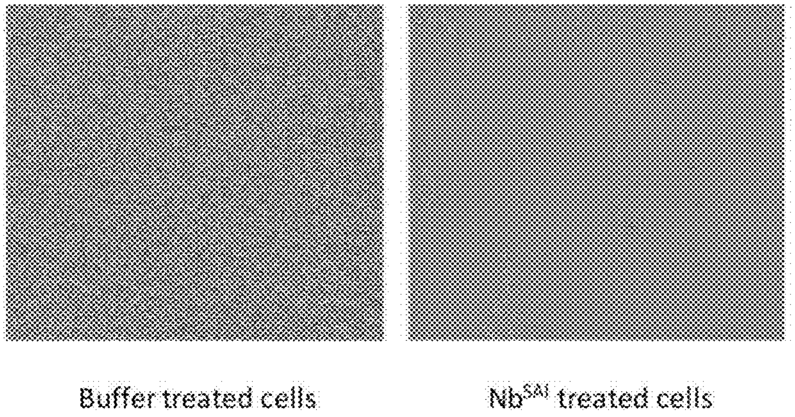

FIG. 15. Inhibition of in vitro and in vivo Sap S-Layer formation using single domain antibodies.

(a) SDS-PAGE of purified *B. anthracis* $Sap^{AD}$ and particle size distribution of fresh (<1 h) and aged (24 h) $Sap^{AD}$ solutions measured by DLS. (b) Negative stain TEM shows that $Sap^{AD}$ self-assembles into tubules and 2D crystals with shown unit cell dimensions. (c) $Sap^{AD}$ particle size distribution after a 7 days incubation in presence of 40 μM of selected anti-Sap Nbs that prevented $Sap^{AD}$ self-assembly. (d, e) $Sap^{AD}$ tubule length distribution and representative negative stain TEM micrographs show in vitro depolymerization activity of 15 μM $Nbs^{SAI}$ on $Sap^{AD}$ tubules. (t: time post treatment, c: tubule count per 5 TEM squares, –: median) (f) $Sap^{AD}$ tubule length distribution using 15 μM Nb11, $Nbs^{SAI}$, $Nb^{AF692}$, 1:1000 mice or llama sera at 1 hour post treatment. (g) S-Layer assembly ratio assessed by DLS at 24 h after addition of buffer, 15 μM Nb11 or $Nbs^{SAI}$, 1:1000 mice or llama sera to $Sap^{AD}$ monomer (h) Growth curves of *B. anthracis* cultured on BHI medium supplemented with buffer, 20 μM $Nbs^{SAI}$ or $Nbs^{S2}$ (pool of Nbs that lack Sap S-Layer inhibitory activity: $Nb^{AF679}$, $Nb^{AF687}$, $Nb^{AF694}$, $Nb^{AF695}$ and $Nb^{AF703}$). Mean±sd, n=3 (i) Phase contrast frames showing *B. anthracis* culture density 5 h post inoculum in absence or presence of 20 μM $Nbs^{SAI}$.

Figure 16:
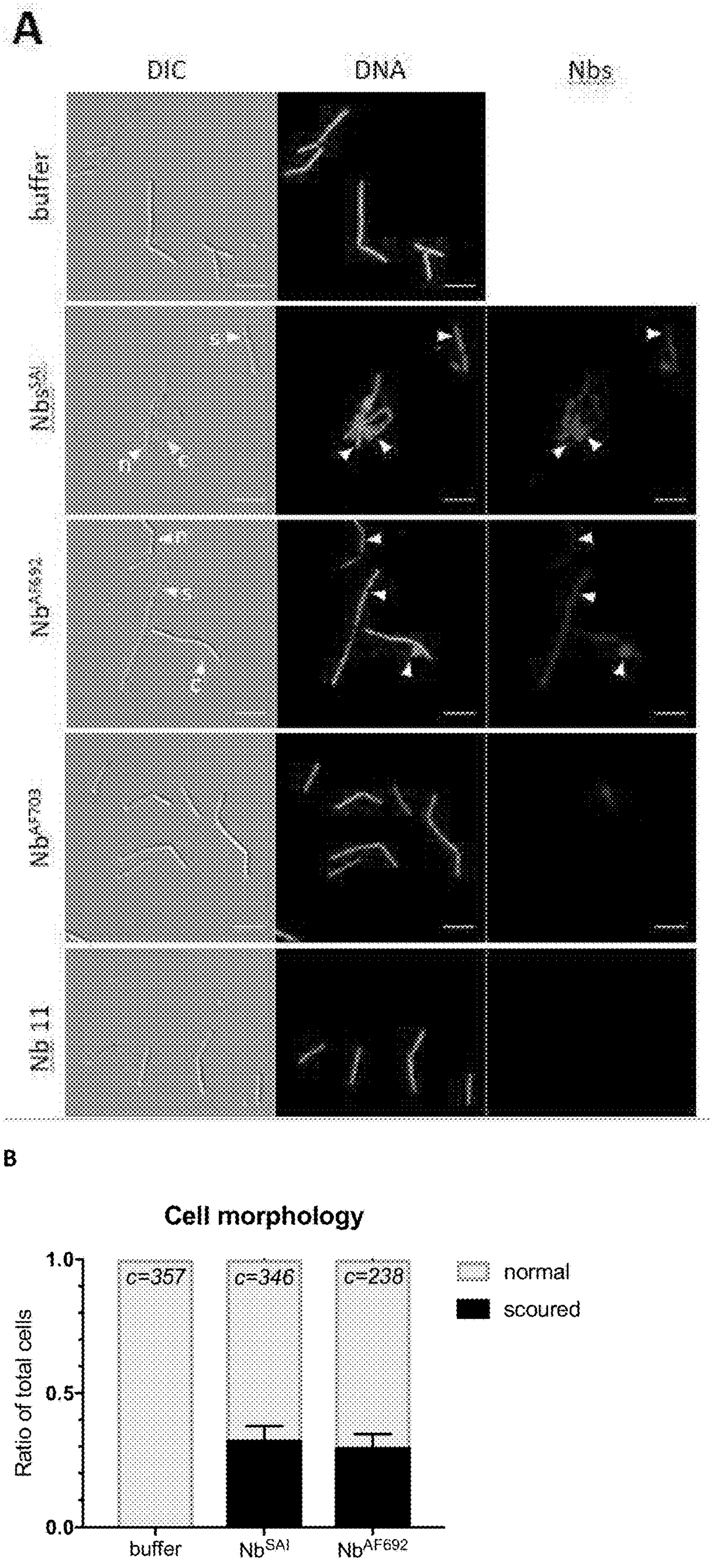
Figure 16:
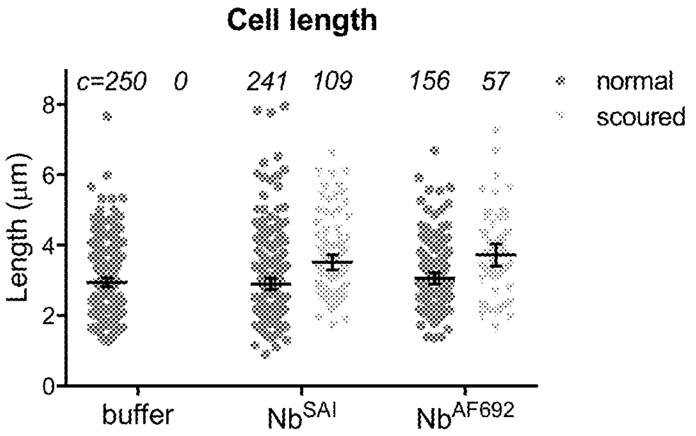
Figure 16:
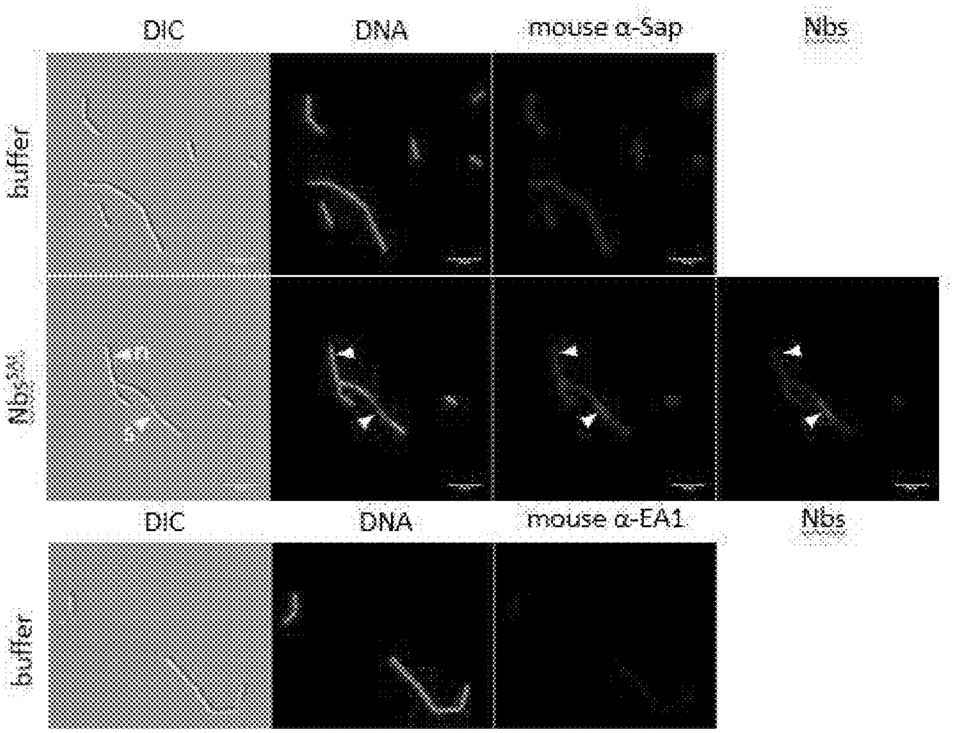

FIG. 16. $Nbs^{SAI}$ affect *B. anthracis* cell morphology.

(a) Fluorescent and differential interference contrast (DIC) micrographs of exponential phase *B. anthracis* cells stained with Syto9 nucleic acid dye and treated with buffer or DyLight 650 labeled $Nbs^{SAI}$, $Nb^{AF692}$, $Nb^{AF703}$ or Nb11. Nb11 or $Nb^{AF703}$ treated cells show a normal (labeled n) cell morphology as seen for buffer treated cells. $Nbs^{SAI}$ or $Nb^{AF692}$ contain normal as well as affected cells. The latter appear as intact cells with a scoured cell surface (labeled s) or as collapsed cell mass (labeled c). (b, c) Bar graph and scatter plot of cell morphology ratio and cell length in normal and scoured cells observed in buffer, $Nbs^{SAI}$ or $Nb^{AF692}$ treated samples. (c: total cell count, –: mean±sd, n=4 independent experiments (b); mean±95% Cl (c)). (d) Staining with DyLight 633 conjugated mouse α-Sap or α-EA1 polyclonal to reveal localization of the respective S-Layer proteins in *B. anthracis* cells treated with buffer or Dylight 594 labeled $Nbs^{SAI}$. Whilst EA1 shows a sparse and punctuate distribution, Sap is more evenly spread at the *B. anthracis* cell surface. Sap and EA1 staining intensify in $Nbs^{SAI}$ affected cells, suggesting an increased accessibility of the antigens in the cells with damaged cell envelope structures. Scale bars: 10 μm.

Figure 17:
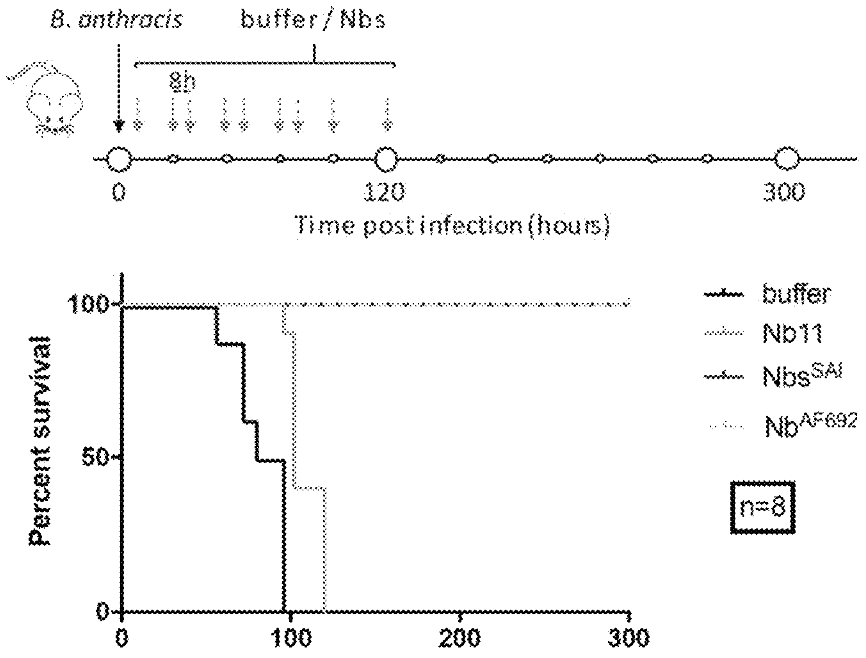
Figure 17:
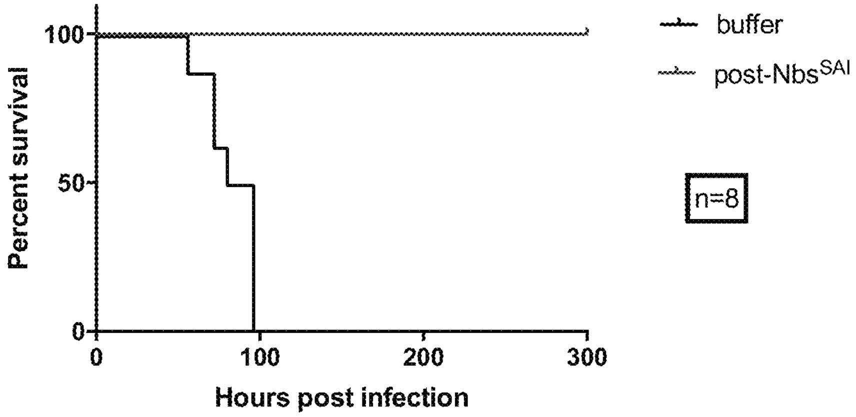
Figure 17:
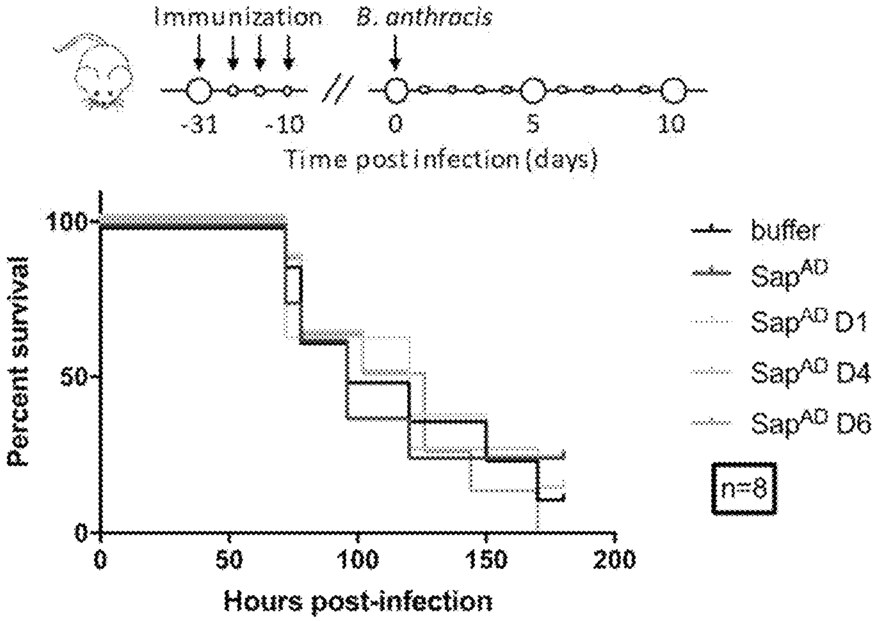
Figure 17:
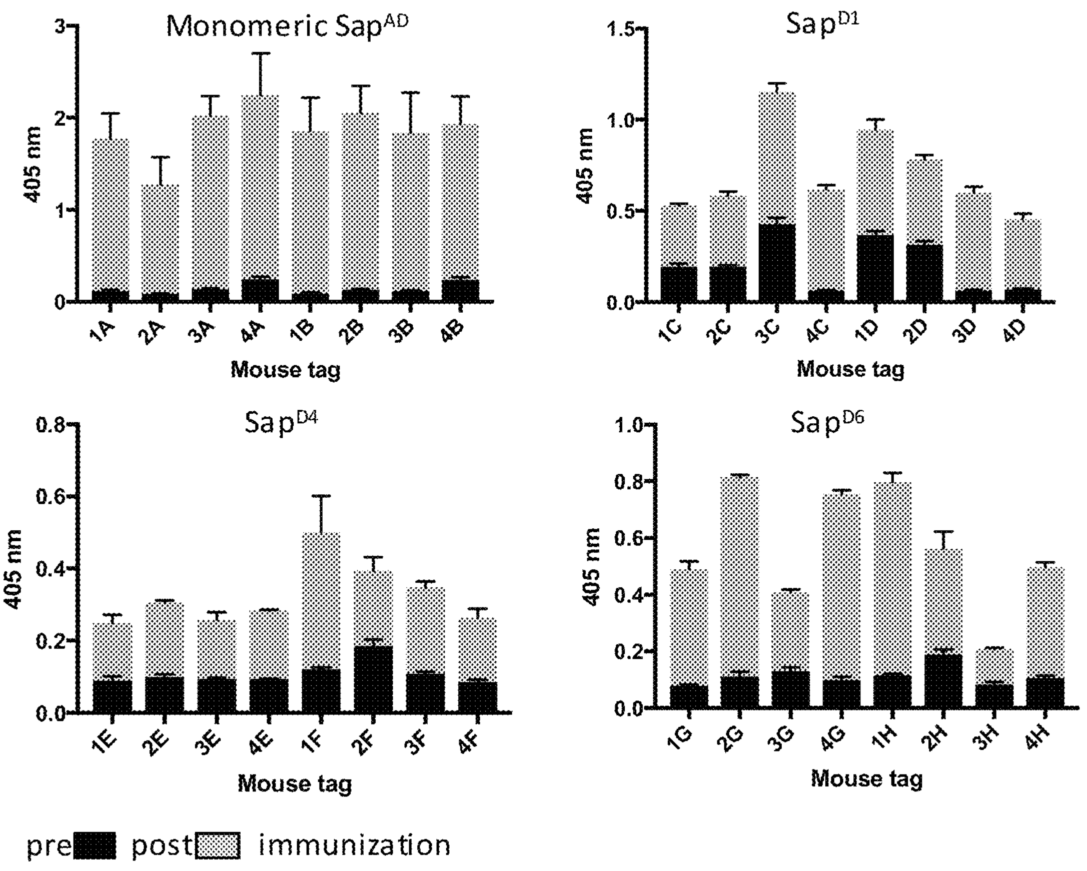

FIG. 17. Clearance of *B. anthracis* infection via $Nbs^{SAI}$ treatment.

(a-b) Schematic diagram and survival curves for *B. anthracis* infection and Nbs treatment studies in mice. Treatment consists of 10 subcutaneous 100 μL doses of 200 μM Nbs or buffer over a 6 day course post infection. Except for buffer controls and panel B, the *B. anthracis* inoculum ($10^5$ CFU) contains a first treatment dose of $Nbs^{SAI}$. (a) Survival curves of mice treated with 200 μM $Nbs^{SAI}$, and individual nanobodies with ($Nb^{AF692}$) or without (Nb11) Sap S-Layer assembly inhibitory activity. (b) Treatment with buffer or $Nbs^{SAI}$ post-infection only. (c) Survival curves and *B. anthracis* infection scheme for mice immunized with monomeric $Sap^{AD}$, D1, D4 or D6. In all panels, n=number of mice per group. (d) Antigen-specific IgG responses as determined by ELISA for mice pre (black) and 10 days post (grey) immunization with monomeric $Sap^{AD}$ or individual Sap domains (D1, D4 or D6). Bars represent individual animals (error bars=sd, n=3 technical replicates).

Figure 18:
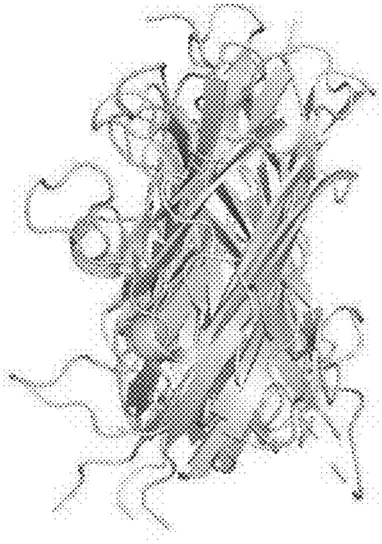
Figure 18:
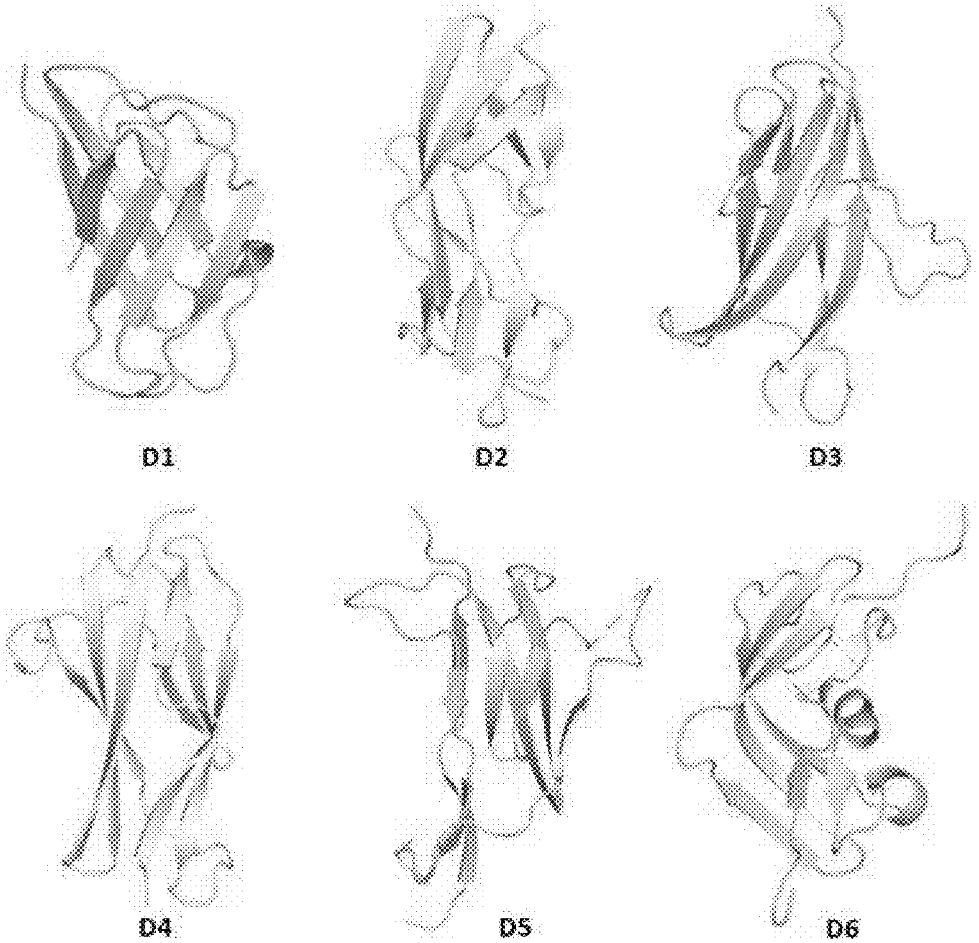
Figure 18:
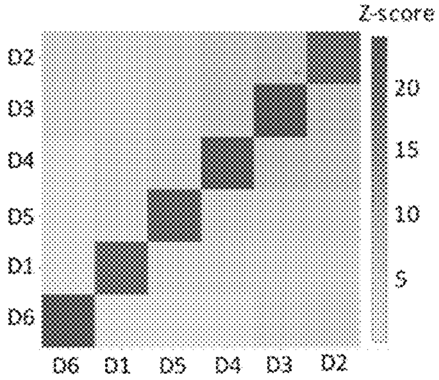

FIG. 18. Domain structure in the Sap assembly domain.

Ribbon diagram of a superimposition of the $Sap^{AD}$ subdomains (a) as well as of individual $Sap^{AD}$ domains (D1-D6 in slate blue, light blue, light green, yellow, light orange and pink, respectively) (b). (c) Z-score matrix for pairwise structural alignment of $Sap^{AD}$ subdomains performed by the program DALI[20]. Domains D1, D2, D3, D4 and D5 are all-beta seven-stranded β-sandwich domains of similar size and topology, whilst D6 is the most distinct subdomain in $Sap^{AD}$ with an alpha beta roll topology.

Figure 19:
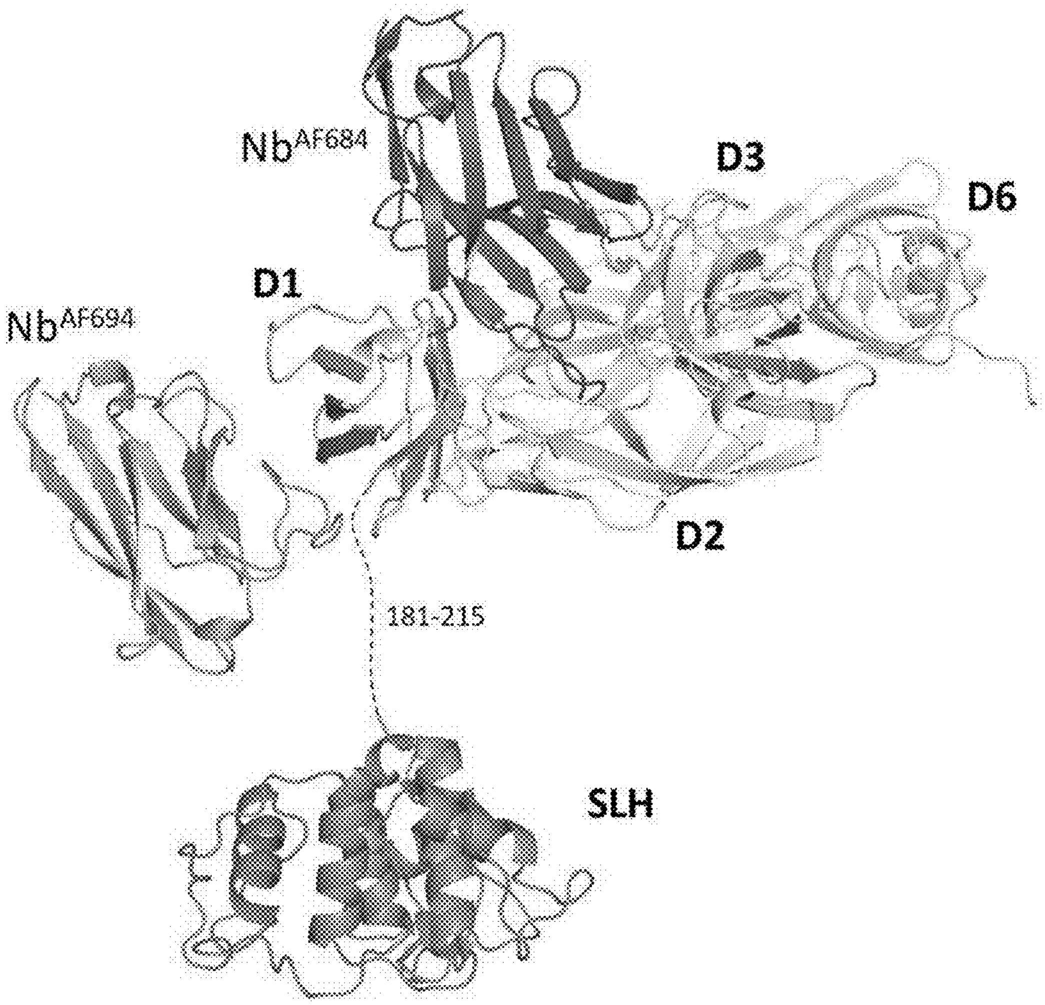
Figure 19:
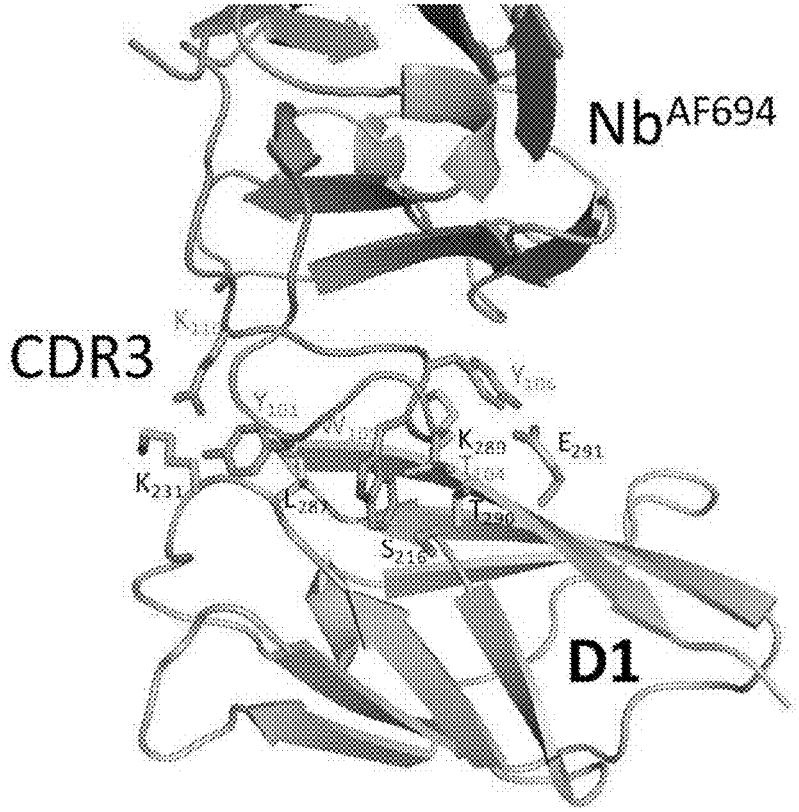
Figure 19:
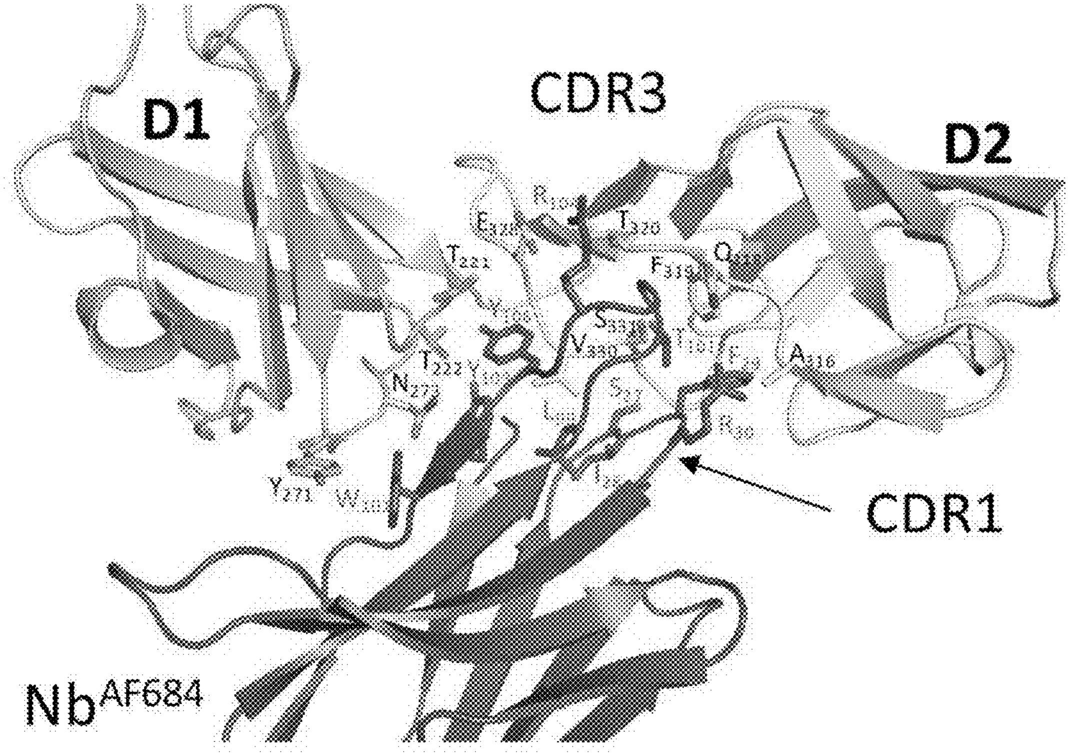

FIG. 19. Nb epitopes in $Sap^{AD}$.

(a) Ribbon diagram of the $Sap^{AD}$ X-ray structure (D1-D6 in slate blue, light blue, light green, yellow, light orange and pink, respectively) bound to crystallization aids $Nb^{AF694}$ (orange) and $Nb^{AF684}$ (blue). The complex is shown in side view, with D1-D2 facing the viewer. For reference, the ribbon diagram of the X-ray structure of SLH domain (magenta; PDB entry: 3PYW; Kern et al., 2011) is drawn to scale and localized in a plausible position relative to the $Sap^{AD}$. The SLH is separated from the $Sap^{AD}$ by a 35 residue linker. $Nb^{AF694}$ and $Nb^{AF684}$ bind domain D1 and the hinge region of domains D1-D2, respectively. (b) Close-up view of the $Nb^{AF694}$-D1 binding interface. Side chains of contacting residues are shown in stick representation. The extended $Nb^{AF694}$ complement determining region 3 (CDR3) binds a surface-localized epitope across the edge of the two β-plates of the D1 β-sandwich. (c) Close-up view of the $Nb^{AF684}$ binding interface with domains D1 and D2. Side chains of contacting residues are shown in stick representation ($Sap^{AD}$ residues are labeled black, $Nb^{AF684}$ residues blue). The Nb CDR3 forms an extensive interaction surface with H-bond, electrostatic and hydrophobic interactions across the D1-D2 hinge region, indicating that $Nb^{AF684}$ will be sensitive to and/or imposing the relative angle of D1-D2 hinge region. The Nb CDR1 makes additional contacts with the domain D2. $Nb^{AF684}$ shares a high sequence similarity in the CDR1 and CDR3 paratope with Nbs in the $Nbs^{SAI}$ group, suggesting that the latter bind the same epitope in the $Sap^{AD}$ D1-D2 hinge region. Although $Nb^{AF684}$ has some Sap assembly inhibitory activity (data not shown), this was less efficient than the 6 nanobodies shown in FIG. 15C, so that $Nb^{AF684}$ was not included in $Nbs^{SAI}$ or further inhibitory studies.

Figure 20:
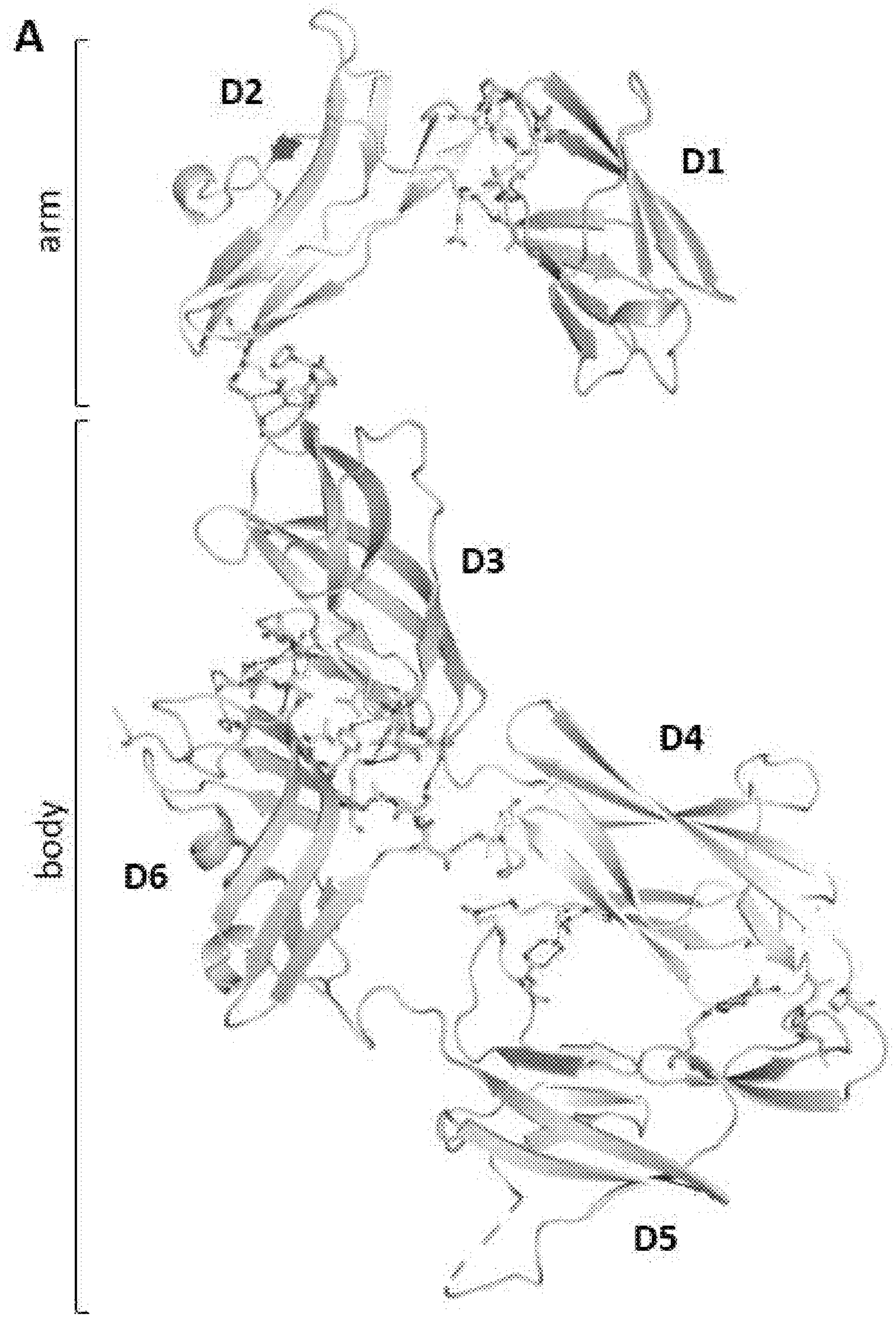
Figure 20:
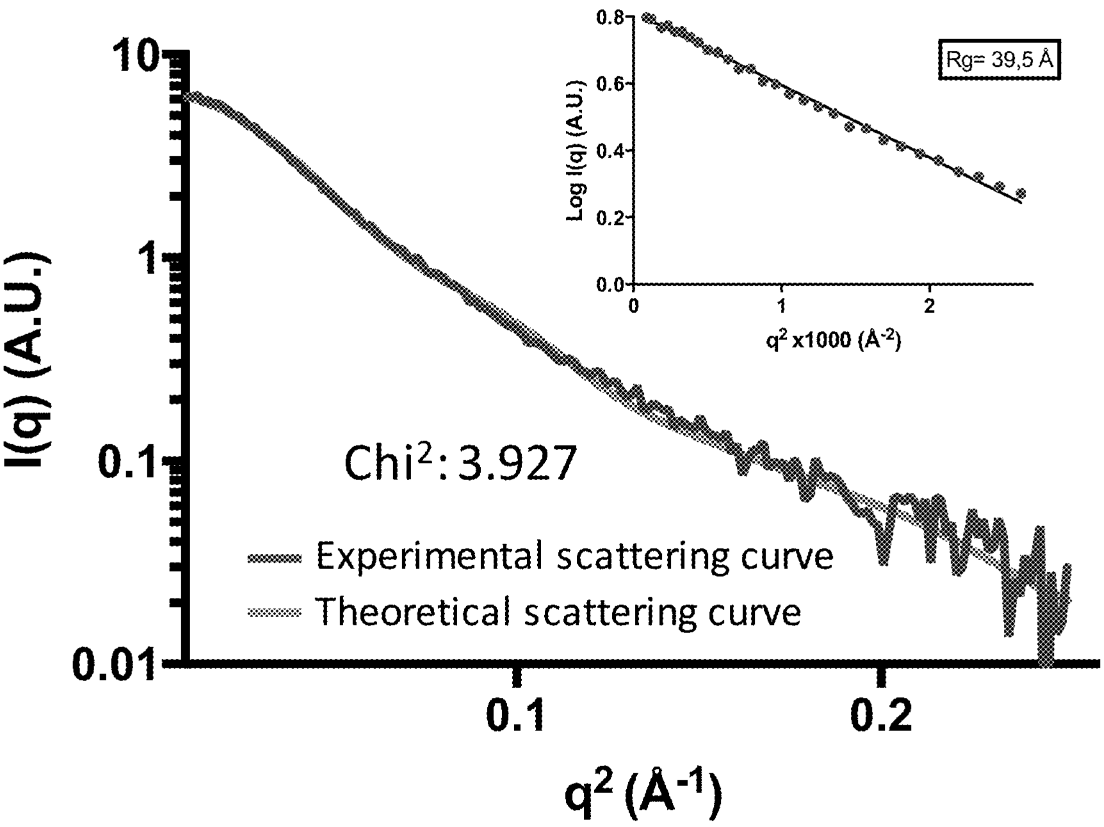
Figure 20:
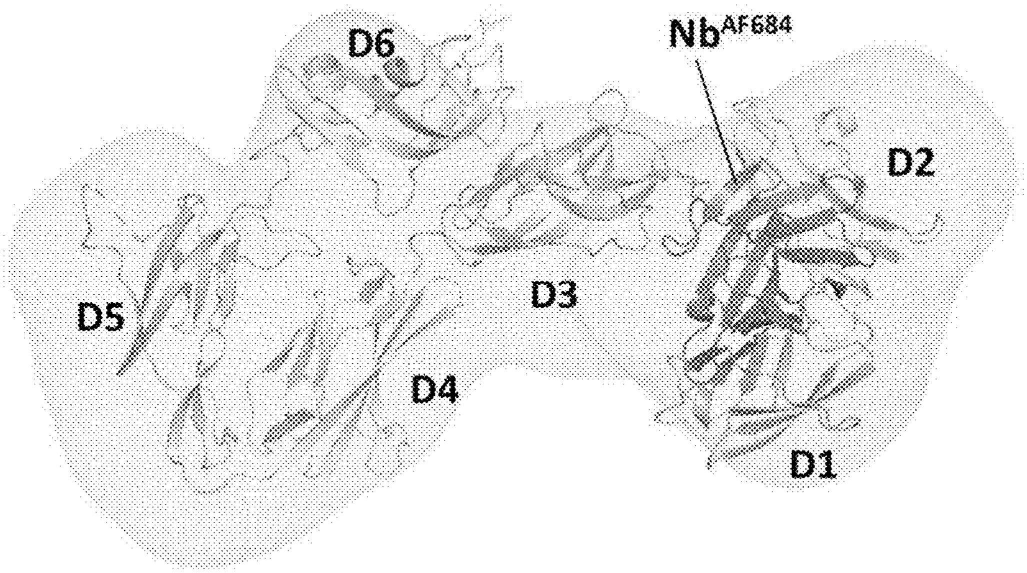

FIG. 20. Supertertiary structure in the Sap S-Layer assembly domain.

(a) Close-up views of the interdomain contacts in the $Sap^{AD}$ structure. Contacting residues are shown in stick representation, with H-bonds and electrostatic interactions shown as dashed lines (red) (b) Analysis of the solution structure of the $Sap^{AD}$ by SAXS. Superposition of the experimental scattering pattern for the $Sap^{AD}$-$Nb^{AF683}$ complex in solution (blue trace) and the theoretical scattering profile (grey trace) calculated from the $Sap^{AD}$-$Nb^{AF684}$ complex as found in the crystal structure (CRYSOL, Svergun et al., 1995). For the solution scattering studies, $Nb^{AF683}$ was used instead of the $Nb^{AF684}$ crystallization aid because the former's superior SAI activity, thus providing monodisperse solutions. Linearity in the Guinier plot (inset) for the experimental SAXS profile and the deduced $R_g$ confirm the sample is monomeric and monodisperse. The close fit of the experimental and theoretical scattering curves ($Chi^2$=3.9) indicate that the $Sap^{AD}$ domain organization and supertertiary structure closely match that seen in the X-ray structure. (c) The $Sap^{AD}$-$Nb^{AF684}$ complex as found in the crystal structure (cartoon representation) docked as rigid body into the ab initio calculated scattering volume generated (volumetric mesh; DAMMIN, Kozin et al., 2001) from the $Sap^{AD}$-$Nb^{AF683}$ SAXS analysis.

Figure 21:
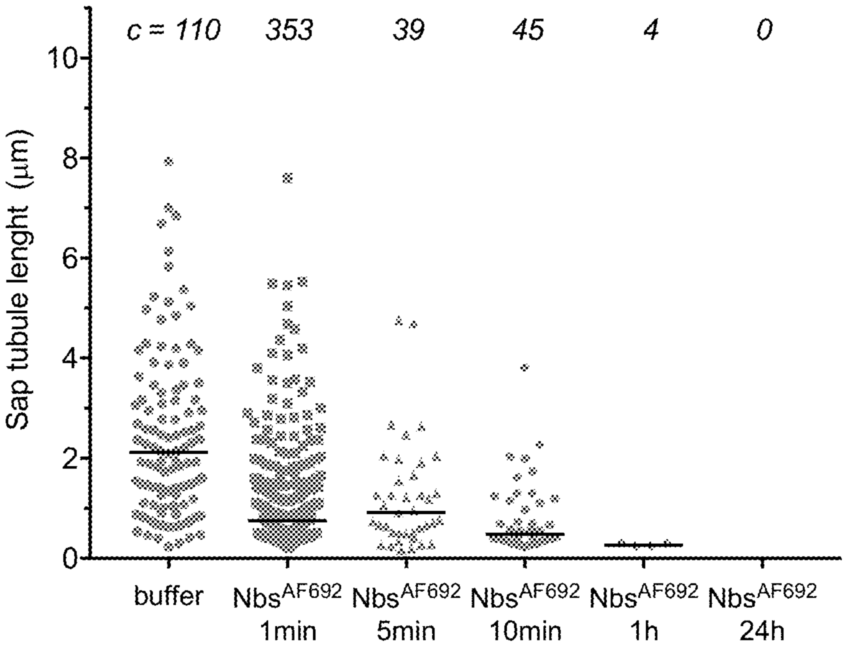
Figure 21:
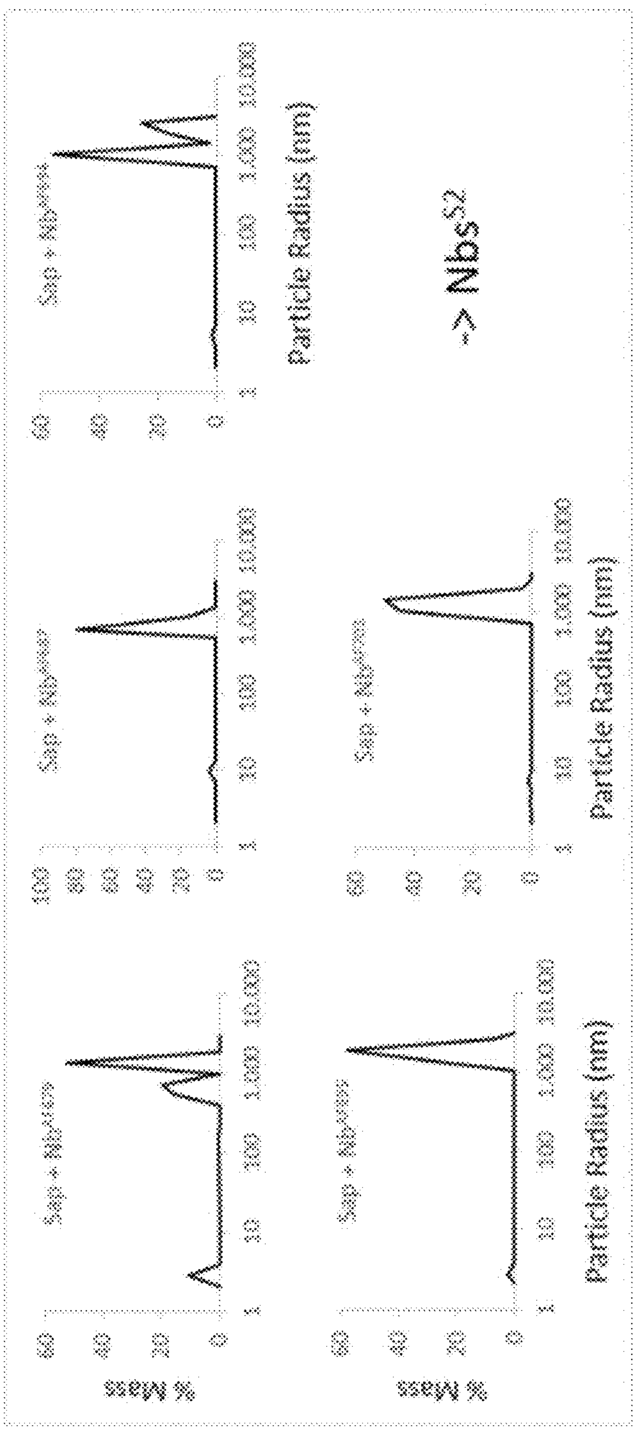

FIG. 21. Analysis of Sap assembly inhibitory activity of Sap-binding Nbs.

(a) Scatter plots of $Sap^{AD}$ tubule length distribution as analyzed by TEM, showing in vitro depolymerization activity of $Nb^{AF692}$ on $Sap^{AD}$ tubules over time (c: tubule count per 5 TEM squares, –: median). Data show that 15 μM $Nb^{AF692}$ is able to depolymerize pre-formed $Sap^{AD}$ tubules with an equivalent efficiency as the $Nbs^{SAI}$ mix (as shown in FIG. 15*e*). (b) $Sap^{AD}$ particle size distribution measured by DLS of α-Sap Nbs with good binding affinity (data not shown) but that lack Sap S-Layer inhibitory activity $Nbs^{S2}$ ($Nb^{AF679}$, $Nb^{AF687}$, $Nb^{AF694}$, $Nb^{AF695}$ and $Nb^{AF703}$). DLS profiles were measured 7 days after addition of 40 μM Nb to freshly purified monomeric $Sap^{AD}$ (0.2 mg/mL). These five nanobodies were pooled into the non-SAI $Nbs^{S2}$ group used as a control in growth inhibition studies (FIG. 15*h*).

Figure 22:
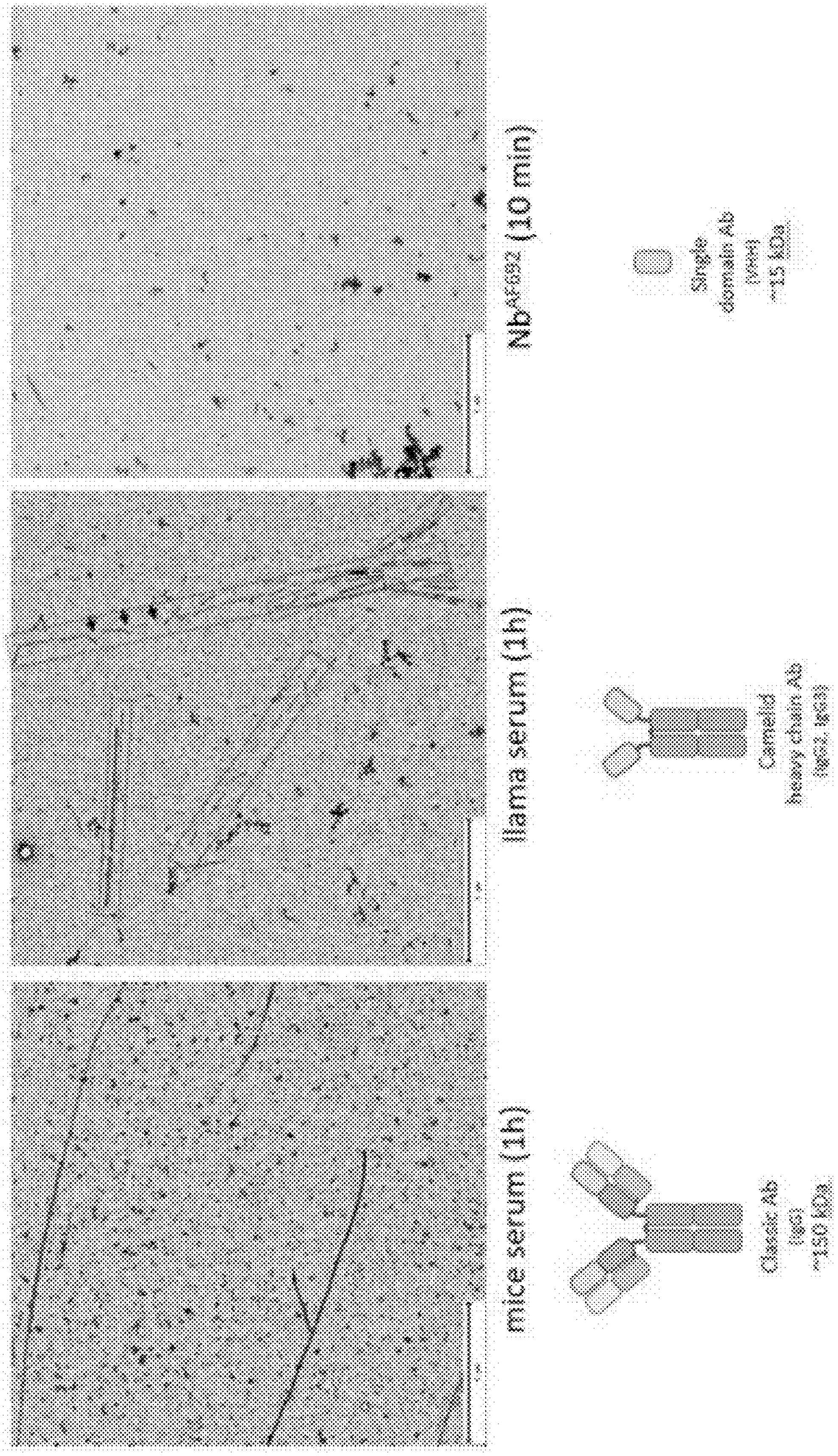

FIG. 22. S-Layer disassembly activity of α-Sap sera and single domain antibodies.

Representative negative stain TEM micrographs monitoring in vitro $Sap^{AD}$ tubule disassembly activity of (1:1000) mice and llama α-Sap sera at 1 h post incubation or 15 μM $Nb^{AF692}$ at 10 min post incubation. Both sera and $Nb^{AF692}$ have Sap S-Layer assembly inhibitory activity, but differ markedly in their ability to disassembly preformed Sap S-Layer lattices. Whilst $Nb^{AF692}$ leads to a near loss of $Sap^{AD}$ tubules within 10 minutes, 1 hour or longer (not shown) treatment with mice sera shows long, intact $Sap^{AD}$ tubules with a number density equivalent to that of buffer-treated sample (FIG. **15*f*). Llama serum showed a partial destabilizing effect on $Sap^{AD}$ tubules. The mean tubule length decreases while tubule number density increased 6-fold compared to buffer treated sample (FIG. 15*f***), indicating fragmentation of the $Sap^{AD}$ tubules. The micrograph shows aligned and kinked $Sap^{AD}$ tubule fragments, suggesting that tubule breakage occurred after deposition on the EM grids and possible as a result of negative staining or grid desiccation. In contrast, aligned or kinked $Sap^{AD}$ tubules were never seen on $Nbs^{SAI}$ or $Nb^{AF692}$ treated samples, suggesting that in case of Nbs, tubule disintegration readily occurs in solution. Thus, llama serum appears able to bind $Sap^{AD}$ tubules, which renders the lattice brittle but does not itself induce lattice dissolution. Differences in activity towards Sap S-Layer lattices may stem from the size of the antigen-binding regions in the different formats. Schematic representation of conventional mouse IgG, camelid single chain (IgG2, IgG3) antibody formats, as well as the VHH single chain nanobody format, with their respective indicative molecular mass.

Figure 23:
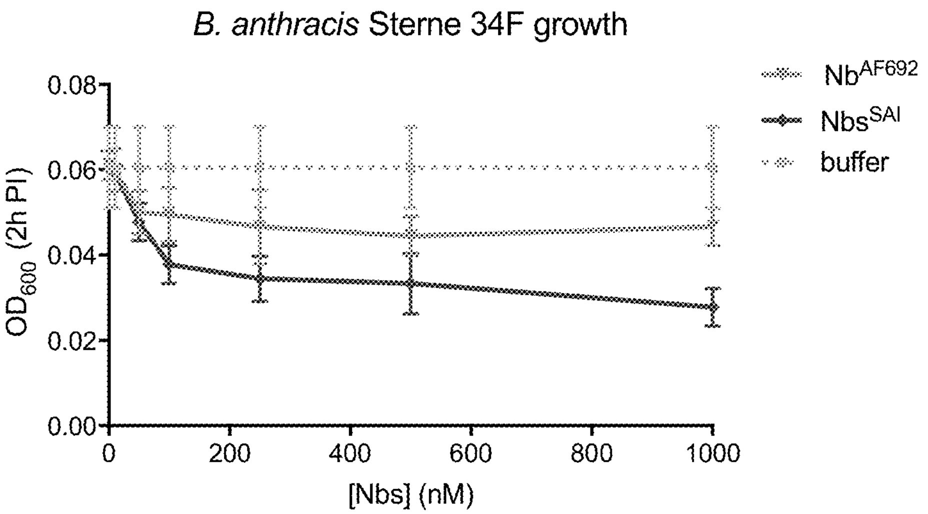

FIG. 23. $Nbs^{SAI}$ attenuate *B. anthracis* growth.

(a) Phase contrast frames from a time-lapse experiment imaging the growth of *B. anthracis* in BHI medium, starting from an inoculum pretreated with buffer or 200 μM $Nbs^{SAI}$. The buffer treated culture goes into a rapidly dividing—exponential growth phase that leads to full cell confluence within 5 h post inoculation while the culture treated with the $Nbs^{SAI}$ shows a strongly reduced growth rate and is unable to reach confluency in 5 h post inoculation. (b) *B. anthracis* growth curves (mean±sd, n=3) plotted as % cell confluency measured by IncuCyte live cell imaging system. Cells were treated with buffer (PBS1×) or 200 μM of the individual Nbs with SAI activity (FIG. **15*c***) as well as a equimolar cocktail of 200 μM $NbS^{SAI}$. $Nb^{AF692}$ at 200 μM induces a strongly reduced growth rate of the treated bacteria comparable to the $Nbs^{SAI}$ treated ones. (NI: not inoculated) (c) Growth curves comparison of *B. anthracis* in BHI medium measured by $OD_{600}$. Cells were treated with buffer or 200 μM $Nbs^{SAI}$, $Nb^{AF692}$ or $Nb^{AF703}$ prior to inoculation (left) or 2 h post-inoculum (right) (mean±sd, n=3). Cell growth is not affected by $Nb^{AF703}$, an α-Sap Nb that lacks Sap assembly inhibitory activity, while it is delayed by ~2 hours in case of $Nbs^{SAI}$ and $Nb^{AF692}$ treatment. (d) Dose response effect of *B. anthracis* cells treated with buffer or increasing concentration of $Nbs^{SAI}$, $Nb^{AF692}$ or $Nb^{AF703}$ prior to inoculation. Plot shows $OD_{600}$ at 2 h post inoculation (mean±sd, n=3).

Figure 24:
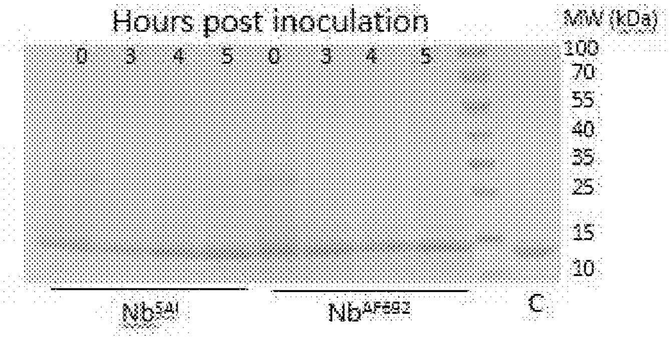
Figure 24:
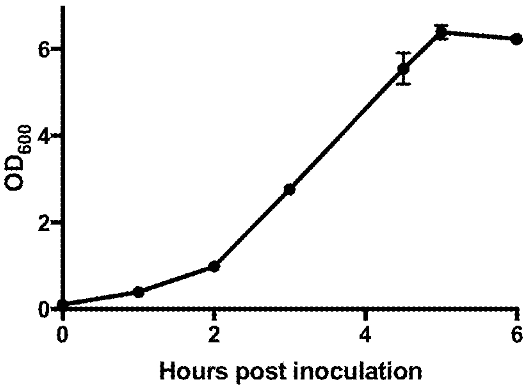
Figure 24:
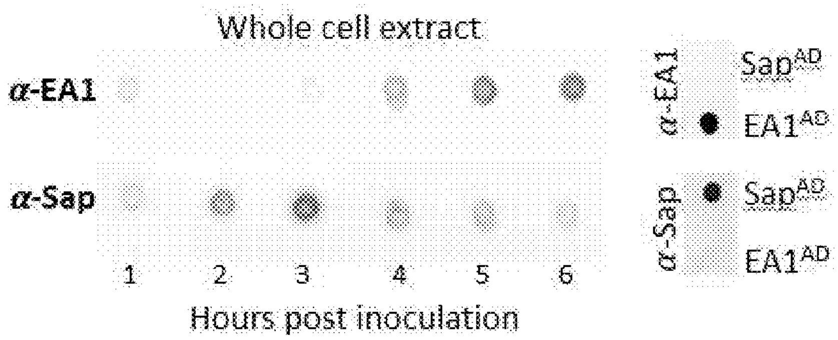
Figure 24:
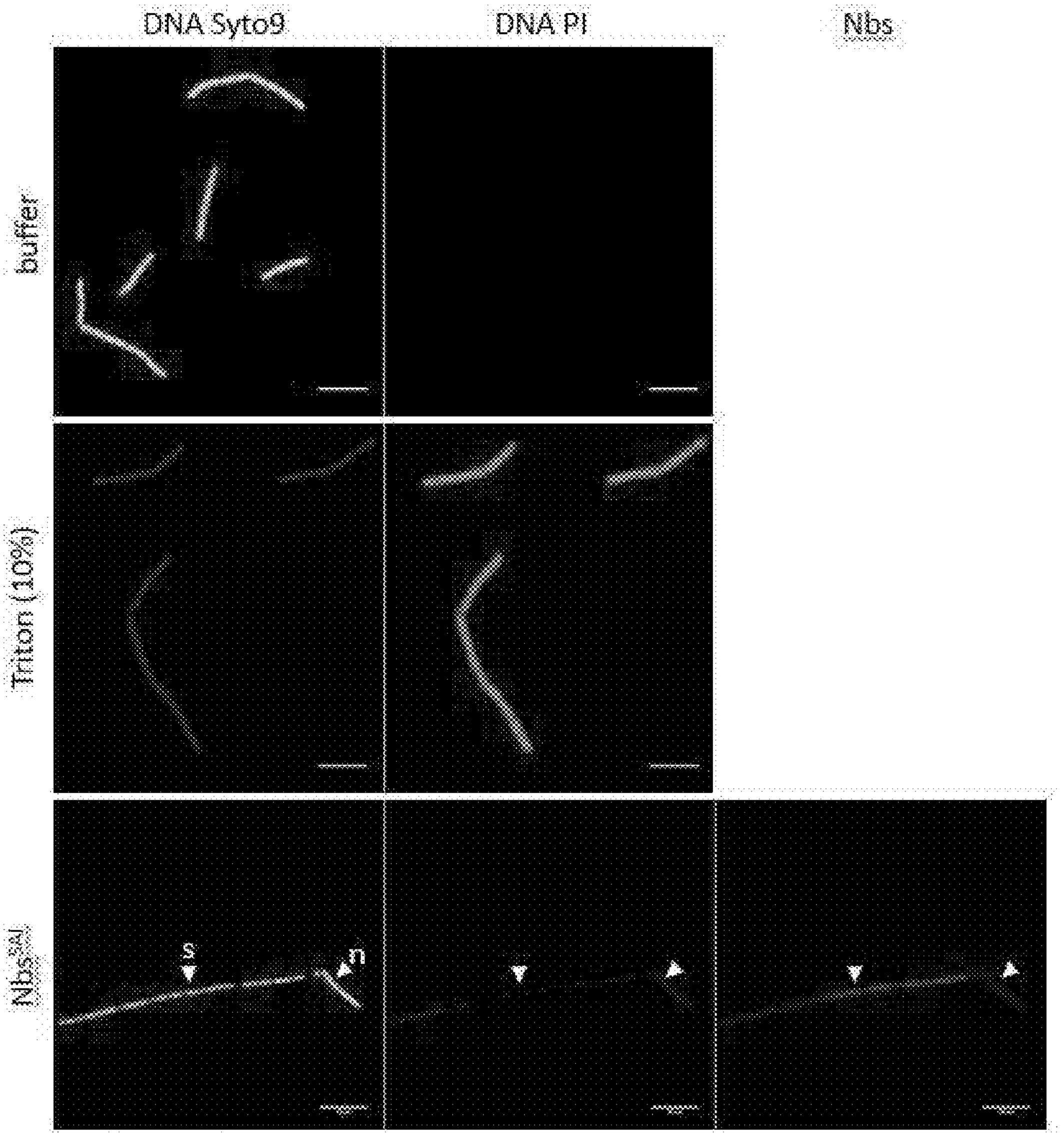

FIG. 24. S-Layers composition during *B. anthracis* growth in BHI and live/death stain on $Nbs^{SAI}$ treated cells.

(a) Coommassie-stained SDS PAGE of $Nbs^{SAI}$ standard (0.2 μM; labeled C) and cleared supernatant (5 min 12000 g) of a *B. anthracis* culture in BHI medium treated prior inoculum with 200 μM $Nbs^{SAI}$ or $Nb^{AF692}$ and sampled at 0, 3, 4 or 5 hours post inoculation (all samples represent 10 μL). The PAGE shows that $Nbs^{SAI}$ are the dominant free proteins in the culture supernatant and remain above the 100 nM minimal inhibitory concentration throughout the culture (b) Growth curve of *B. anthracis* in BHI medium at 37° C. (mean±sd, n=3). Inocula were started from an overnight culture diluted to $OD_{600}$ 0.1. (c) Whole cell dot blot analysis of *B. anthracis* cells showing the developmental switch of Sap and EA1 S-Layer during growth in BHI as reported before[11] (right) recombinant purified $Sap^{AD}$ or $EA1^{AD}$ were used as positive controls for antibody specificity. (d) LIVE/DEAD™ BacLight™ assay to establish bacterial viability of $Nbs^{SAI}$ treated *B. anthracis* cells. Cells harvested at exponential growth phase were treated with buffer, Triton 10% as a cell lysis control or 200 μM $Nbs^{SAI}$. Buffer treated cells are Syto9 positive and propidium iodide (PI) negative, indicative of intact cell membrane integrity and considered viable; Triton treated cells stained Syto9 negative, PI positive in agreement with a compromised cell membrane. In the $Nbs^{SAI}$ treated sample, both normal (n) non-affected cells and scoured (s) cells stained with Syto9 dye and were PI negative, indicating cell membrane integrity for both phenotypes and suggesting the scoured phenotype encompasses a defect of the outer cell surface only. Scale bars correspond to 10 μm.

Figure 25:
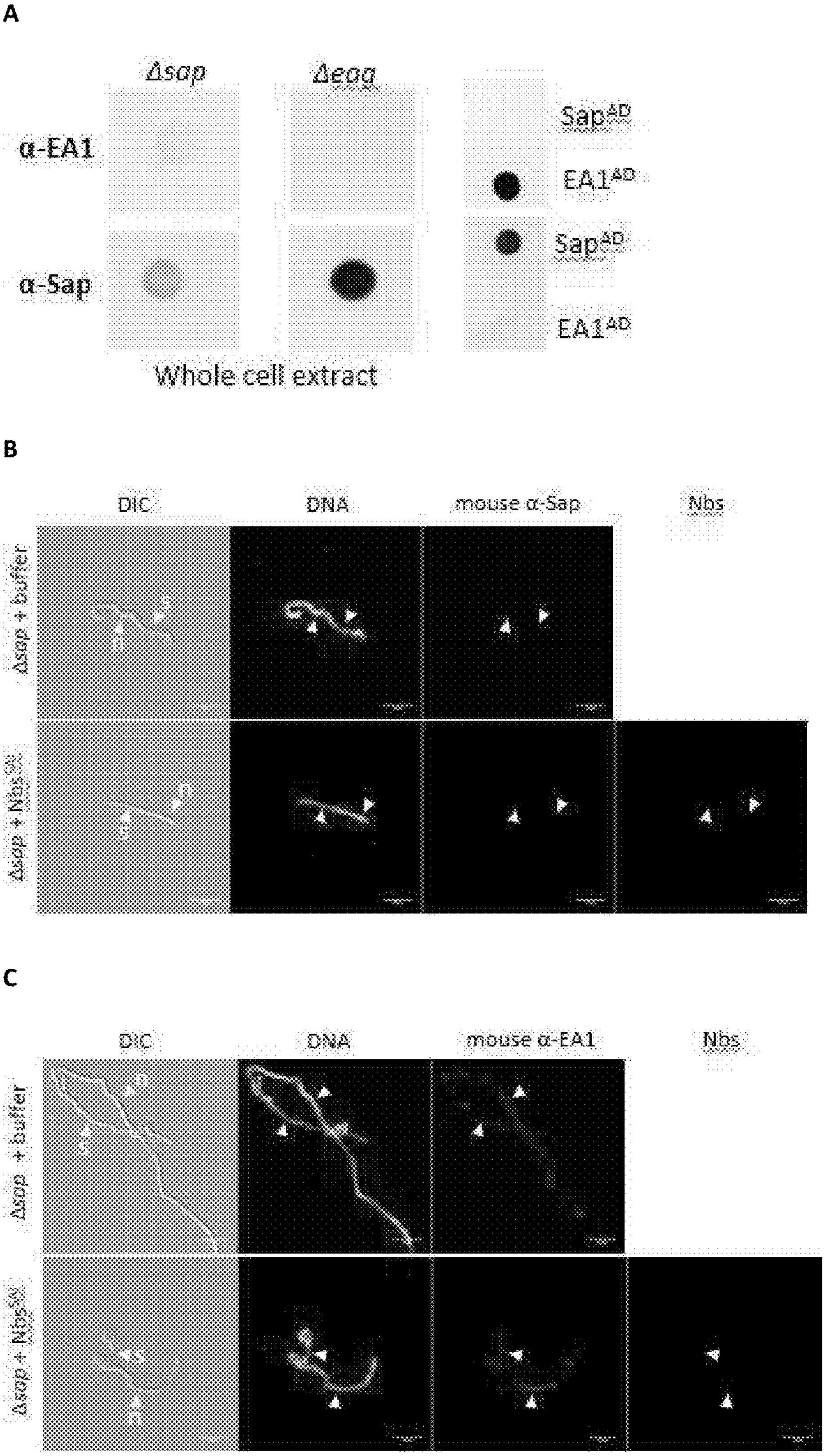
Figure 25:
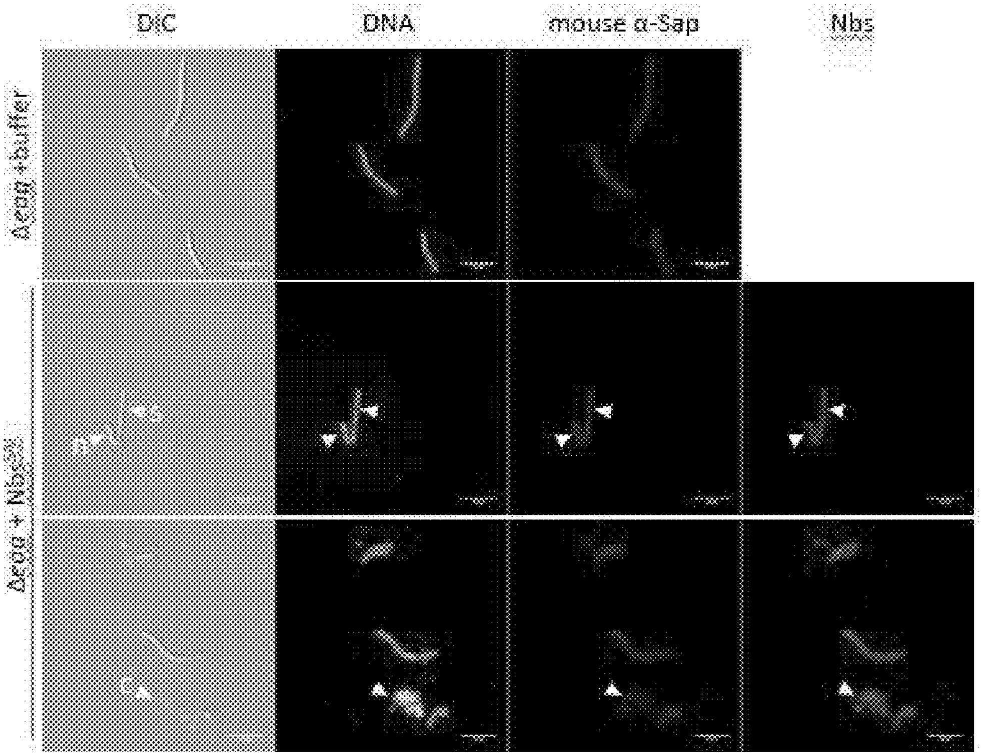
Figure 25:
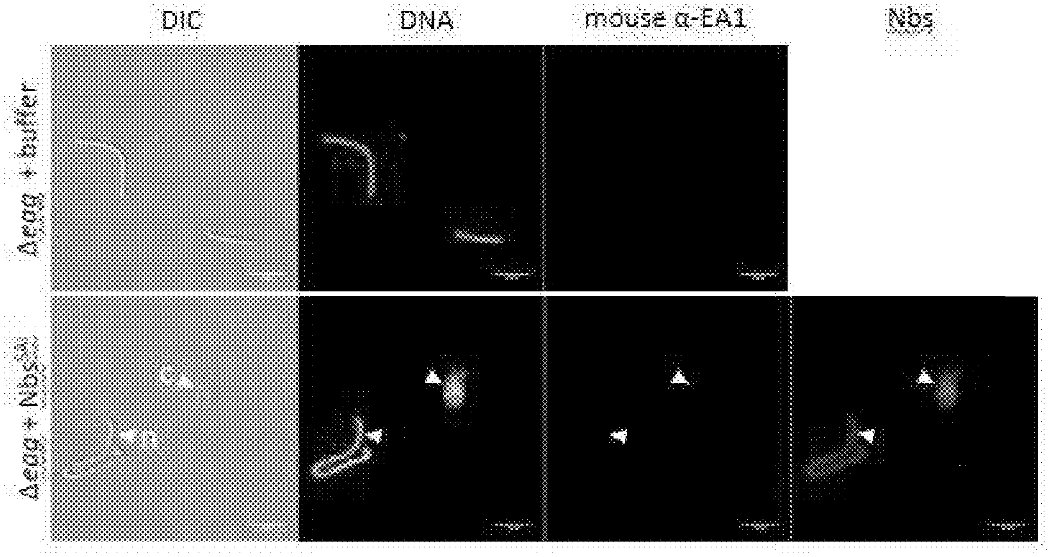

FIG. 25. $Nbs^{SAI}$ affect cell morphology of Δeag mutant *B. anthracis* but not Δsap cells.

(a) Confirmation of Sap or EA1 negative phenotype in *B. anthracis* Δeag or Δsap using whole cell dot blot and α-Sap or α-EA1 mouse polyclonal antibodies. (b-d) DIC and fluorescent microscopy of buffer or $Nbs^{SAI}$ treated Δeag (B and C) and Δsap (D and E) *B. anthracis* cells grown in BHI medium and harvested in exponential phase (2 hours post inoculation). Cells are stained with Syto9 nucleic acid stain, Dylight594 labeled $Nbs^{SAI}$ and DyLight 633 conjugated mouse α-Sap (b and d) or α-EA1 (c and e) polyclonal antibodies to localize the respective S-Layer proteins. *B. anthracis* Δsap cultures show cells with normal (n) as well as scoured (s) morphology both in buffer and $Nbs^{SAI}$ treated samples, whereas in *B. anthracis* Δeag cultures the scoured morphology is seen only in $Nbs^{SAI}$ treated samples, demonstrating that the scoured cell surface morphology is specific to cells lacking Sap, either by genetic knockout or treatment with Sap effacing nanobodies ($Nbs^{SAI}$). The collapsed (c) cell morphology was observed in $Nbs^{SAI}$ treated Sap positive cells only (panels D and E). Scale bars correspond to 10 μm.

Figure 26:
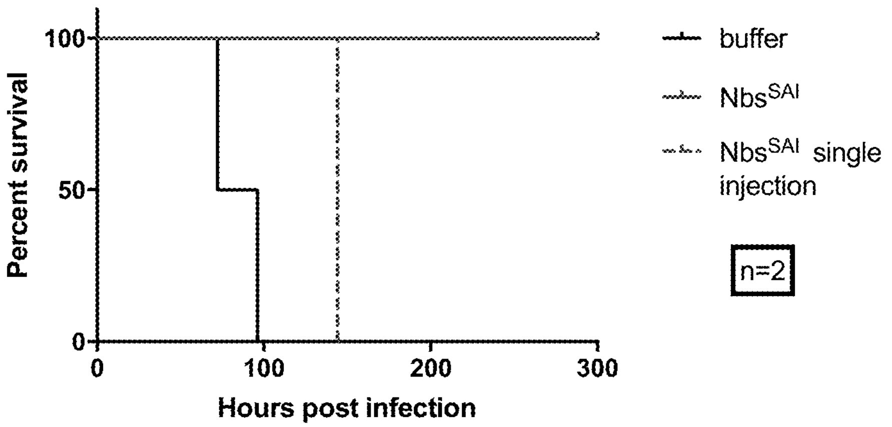
Figure 26:
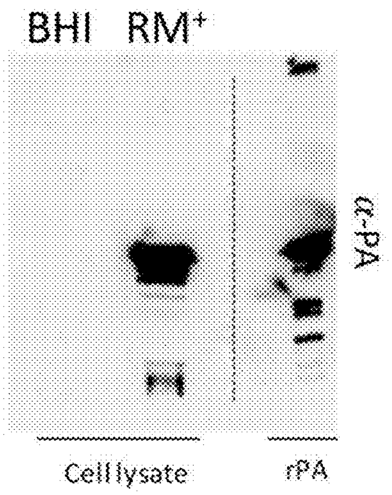
Figure 26:
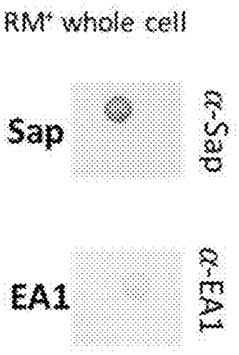
Figure 26:
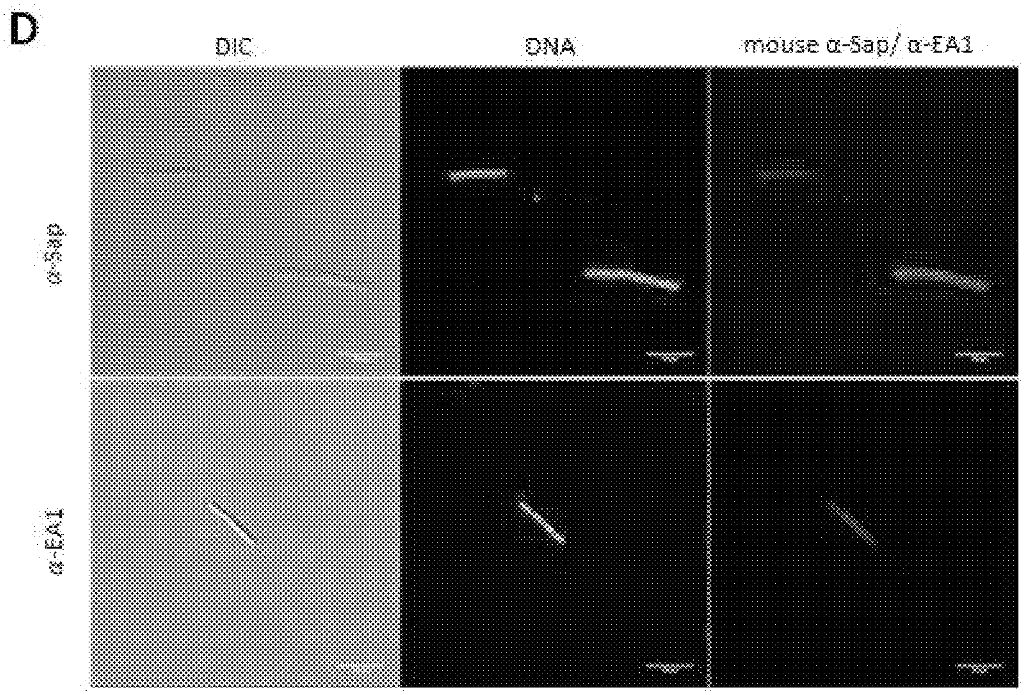
Figure 26:
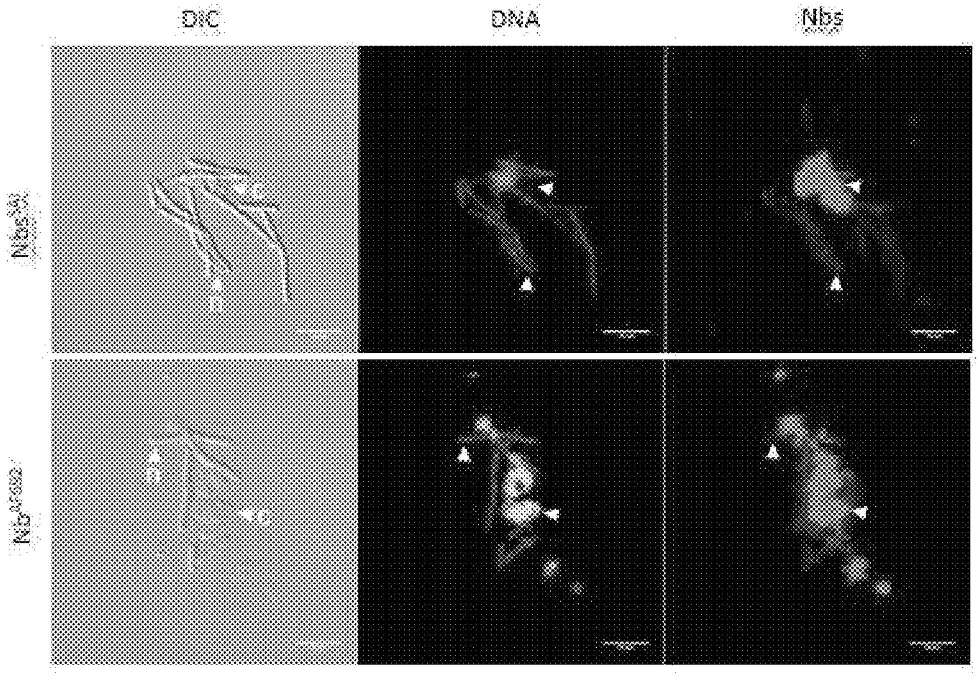

FIG. 26. *B. anthracis* S-Layer composition and $Nbs^{SAI}$ induced cell morphology defects in cells grown in toxin producing medium $RM^{+}$.

(a) Survival curves for a pilot mouse experiment showing that $Nbs^{SAI}$ treatment of *B. anthracis* infected cells requires consecutive treatment doses and that providing a single $Nbs^{SAI}$ dose at the time of infection doesn't prevent mice developing lethal anthrax disease. (b) Immunoblot analysis of BHI and $RM^{+}$ medium culture supernatants using mouse monoclonal α-Protective Antigen (PA). Recombinant PA (rPA) was used as positive control. *B. anthracis* cells grown in $RM^{+}$ but not BHI medium produce the anthrax toxins and represent the inoculum used for the mice infection experiments. (c). Whole cell dot blots analysis of *B. anthracis* cells grown in $RM^{+}$ medium show that Sap is the dominant S-Layer protein (d) DIC and fluorescent microscopy of *B. anthracis* cells grown in $RM^{+}$ medium. Cells are stained with Syto9 nucleic acid stain and DyLight 594 conjugated mouse α-Sap or α-EA1 polyclonal antibodies to reveal S-Layer composition. Cells predominantly express the Sap S-Layer. (e) DIC and fluorescent microscopy of *B. anthracis* grown on $RM^{+}$ and treated with 200 μM Dylight594 labeled $Nbs^{SAI}$. $Nbs^{SAI}$ induce massive morphological defects (collapsed cells) in these toxins producing, Sap-dominant cells.

DETAILED DESCRIPTION TO THE INVENTION

The present invention will be described with respect to particular embodiments and with reference to certain drawings, but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to one embodiment' or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Definitions

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $4^{th}$ ed., Cold Spring Harbor Press, Plainsview, N.Y. (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analogue. By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

"Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances. Recombinant host cells, in the present context, are those which have been genetically modified to contain an isolated DNA molecule, nucleic acid molecule or expression construct or vector. The DNA can be introduced by any means known to the art which are appropriate for the particular type of cell, including without limitation, transformation, lipofection, electroporation or viral mediated transduction. A DNA construct capable of enabling the expression of the chimeric protein of the invention can be easily prepared by the art-known techniques such as cloning, hybridization screening and Polymerase Chain Reaction (PCR). Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989), Maniatis et al. (1982), Wu (ed.) (1993) and Ausubel et al. (1992). Representative host cells that may be used with the invention include, but are not limited to, bacterial cells, yeast cells, plant cells and animal cells. Bacterial host cells suitable for use with the invention include *Escherichia* spp. cells, *Bacillus* spp. cells, *Streptomyces* spp. cells, *Erwinia* spp. cells, *Klebsiella* spp. cells, *Serratia* spp. cells, *Pseudomonas* spp. cells, and *Salmonella* spp. cells. Animal host cells suitable for use with the invention include insect cells and mammalian cells (most particularly derived from Chinese hamster (e.g. CHO), and human cell lines, such as HeLa. Yeast host cells suitable for use with the invention include species within *Saccharomyces, Schizosaccharomyces, Kluyveromyces, Pichia* (e.g. *Pichia pastoris*), *Hansenula* (e.g. *Hansenula polymorpha*), *Yarowia, Schwaniomyces, Schizosaccharomyces, Zygosaccharomyces* and the like. *Saccharomyces cerevisiae, S. carlsbergensis* and *K. lactis* are the most commonly used yeast hosts, and are convenient fungal hosts. The host cells may be provided in suspension or flask cultures, tissue cultures, organ cultures and the like. Alternatively, the host cells may also be transgenic animals.

The terms "protein", "polypeptide", "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes posttranslational modifications of the polypeptide, such as glycosylation, phosphorylation and acetylation. Based on the amino acid sequence and the modifications, the atomic or molecular mass or weight of a polypeptide is expressed in (kilo)dalton (kDa). By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation. By "isolated" is meant material that is substantially or essentially free from components that normally accompany it in its native state. For example, an "isolated polypeptide" refers to a polypeptide which has been purified from the molecules which flank it in a naturally-occurring state, e.g., an SLP binding protein or compound which has been removed from the molecules present in the production host that are adjacent to said polypeptide. The expression "heterologous protein" may mean that the protein is not derived from the same species or strain that is used to display or express the protein.

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. "Homologue", "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

As used herein, the terms "determining," "measuring," "assessing," and "assaying" are used interchangeably and include both quantitative and qualitative determinations.

The terms "suitable conditions" refers to the environmental factors, such as temperature, movement, other components, and/or "buffer condition(s)" among others, wherein "buffer conditions" refers specifically to the composition of the solution in which the assay is performed. The said composition includes buffered solutions and/or solutes such as pH buffering substances, water, saline, physiological salt solutions, glycerol, preservatives, etc. for which a person skilled in the art is aware of the suitability to obtain optimal assay performance.

The term "antibody" as used herein, refers to an immunoglobulin (Ig) molecule or a molecule comprising an immunoglobulin (Ig) domain, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The term "active antibody fragment" refers to a portion of any antibody or antibody-like structure that by itself has high affinity for an antigenic determinant, or epitope, and contains one or more CDRs accounting for such specificity. Non-limiting examples include immunoglobulin domains, Fab, F(ab)'2, scFv, heavy-light chain dimers, immunoglobulin single variable domains, Nanobodies, domain antibodies, and single chain structures, such as a complete light chain or complete heavy chain. An additional requirement for "activity" of said fragments in the light of the present invention is that said fragments are capable of binding the S-Layer protein and inhibit polymerization of said S-Layer protein.

The term "antibody", "antibody fragment" and "active antibody fragment" as used herein refer to a protein comprising an immunoglobulin domain or an antigen binding domain capable of specifically binding the bacterial SLP. The term "immunoglobulin (Ig) domain", or more specifically "immunoglobulin variable domain" (abbreviated as "IVD") means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) (IVDs) that confer specificity to an antibody for the antigen by carrying the antigen-binding site. An "immunoglobulin single variable domains" (abbreviated as "ISVD"), which is equivalent to the term "single variable domains", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen. In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs. As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit). In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody. For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH); other single variable domains, or any suitable fragment of any one thereof. In particular, the immunoglobulin single variable domain may be a Nanobody (as defined herein) or a suitable fragment thereof. Note: Nanobody®, Nanobodies® and Nanoclone® are registered trademarks of Ablynx N.V. For a general description of Nanobodies, reference is made to the further description below, as well as to the prior art cited herein, such as e.g. described in WO2008/020079. "VHH domains", also known as VHHs, VHH domains, VHH antibody fragments, and VHH antibodies, have originally been described as the antigen binding immunoglobulin (Ig) (variable) domain of "heavy chain antibodies" (i.e., of "antibodies devoid of light chains"; Hamers-Casterman et al (1993) Nature 363: 446-448). The term "VHH domain" has been chosen to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). Fora further description of VHHs and Nanobody, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As described in these references, Nanobody (in particular VHH sequences and partially humanized Nanobody) can in particular be characterized by the presence of one or more "Hallmark residues" in one or more of the framework sequences. A further description of the Nanobody, including humanization and/or camelization of Nanobody, as well as other modifications, parts or fragments, derivatives or "Nanobody fusions", multivalent constructs (including some non-limiting examples of linker sequences) and different modifications to increase the half-life of the Nanobody and their preparations can be found e.g. in WO 08/101985 and WO 08/142164.

"Domain antibodies", also known as "Dabs", "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans. It should also be noted that single variable domains can be derived from certain species of shark (for example, the so-called "IgNAR domains", see for example WO 05/18629).

Immunoglobulin single variable domains such as Domain antibodies and Nanobody (including VHH domains and humanized VHH domains), can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996). The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats for instance to avoid glycosylation will be clear to the skilled person based on the disclosure herein.

Immunoglobulin single variable domains such as Domain antibodies and Nanobody (including VHH domains) can be subjected to humanization, i.e. increase the degree of sequence identity with the closest human germline sequence. In particular, humanized immunoglobulin single variable domains, such as Nanobody (including VHH domains) may be immunoglobulin single variable domains that are as generally defined for in the previous paragraphs, but in which at least one amino acid residue is present (and in particular, at least one framework residue) that is and/or that corresponds to a humanizing substitution. Potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person. Also, based on what is described before, (the framework regions of) an immunoglobulin single variable domain, such as a Nanobody (including VHH domains) may be partially humanized or fully humanized.

The term "antibody mimetic", as used herein, refers to artificial (poly-)peptides that, like antibodies, can specifically bind antigens, but that are not structurally related to antibodies. They are usually significantly smaller than antibodies with a molar mass of about 3 to 20 kDa. Non-limiting examples of antibody mimetics are affibodies, affilins, affimers, alphabodies, affitins, anticalins, avimers, DARPins, fynomers, Kunits domain peptides, monobodies, Z domain of Protein A, Gamma B crystalline, ubiquitin, cystatin, Sac7D from Sulfolobus acidocaldarius, lipocalin, A domain of a membrane receptor, ankyrin repeat motive, SH3 domain of Fyn, Kunits domain of protease inhibitors, the $10^{th}$ type III domain of fibronectin, 3- or 4-helix bundle proteins, an armadillo repeat domain, a leucine-rich repeat domain, a PDZ domain, a SUMO or SUMO-like domain, an immunoglobulin-like domain, phosphotyrosine-binding domain, pleckstrin homology domain, src homology 2 domain or synthetic peptide ligands, e.g., from a (random) peptide library. Synthetic peptide ligands have non-naturally occurring amino acid sequences that function to bind a particular target molecule.

An "epitope", as used herein, refers to an antigenic determinant of a polypeptide. An epitope could comprise 3 amino acids in a spatial conformation, which is unique to the epitope. Generally, an epitope consists of at least 4, 5, 6, 7 such amino acids, and more usually, consists of at least 8, 9, 10 such amino acids. A "paratope", as used herein, refers to the antigen-binding site and is a part of an antibody or antibody fragment or single domain antibody or the like, which recognizes and binds to an antigen. It is a small region (of 5 to 10 amino acids) of the antibody's variable region. Methods of determining the spatial conformation of amino acids are known in the art, and include, for example, X-ray crystallography and multi-dimensional nuclear magnetic resonance. A "conformational epitope", as used herein, refers to an epitope comprising amino acids in a spatial conformation that is unique to a folded 3-dimensional conformation of a polypeptide. Generally, a conformational epitope consists of amino acids that are discontinuous in the linear sequence but that come together in the folded structure of the protein. The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three dimensional folding of a polypeptide chain), and quaternary structure (e.g., interactions of a polypeptide chain with other protein subunits). Posttranslational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological. Macromolecules, W. H. Freeman and Company, 1980, and Creighton, Proteins: Structures and Molecular Properties, W. H. Freeman and Company, 1993.

The term "affinity", as used herein, generally refers to the degree to which a ligand (as defined further herein) binds to a target protein so as to shift the equilibrium of target protein and ligand toward the presence of a complex formed by their binding. Thus, for example, where a chimeric polypeptide and a ligand are combined in relatively equal concentration, a ligand of high affinity will bind to the chimeric polypeptide so as to shift the equilibrium toward high concentration of the resulting complex. In fact, the antigen and immunoglobulin also form a ligand and binding or interacting protein. The dissociation constant Kd is commonly used to describe the affinity between a ligand and a target protein. Typically, the dissociation constant has a value that is lower than $10^{-5}$ M. Preferably, the dissociation constant is lower than $10^{-6}$ M, more preferably, lower than $10^{-7}$ M. Most preferably, the dissociation constant is lower than $10^{-8}$ M. Other ways of describing the affinity between a ligand and its target protein are the association constant (Ka), the inhibition constant (Ki), or indirectly by evaluating the potency of ligands by measuring the half maximal inhibitory concentration ($IC_{50}$) or half maximal effective concentration ($EC_{50}$). It will be appreciated that within the scope of the present invention, the term "affinity" is used in the context of the antigen-binding chimeric protein comprising the Ig domain that binds a (conformational) epitope of the target protein, more particularly the antigen-binding chimeric protein Ig domain retaining its "functionality" to bind its target via the CDR regions of said Ig domain.

"Binding" means any interaction, be it direct or indirect. A direct interaction implies a contact between the binding partners. An indirect interaction means any interaction whereby the interaction partners interact in a complex of more than two molecules. In general, a binding domain can be immunoglobulin-based or it can be based on domains present in proteins, including but limited to microbial proteins, protease inhibitors, toxins, fibronectin, lipocalins, single chain antiparallel coiled coil proteins or repeat motif proteins. By the term "specifically binds," as used herein with respect to for instance an active antibody fragment or single domain antibody comprising an immunoglobulin domain, is meant a binding domain which recognizes a specific target protein or protein domain, but does not substantially recognize or bind other molecules in a sample. For example, an antibody that specifically binds to an antigen from one species, such as Sap protein from *B. anthracis*, may also bind to that antigen from one or more species, such as the conserved Sap SLP from *B. cereus*. But, such cross-species reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. The term "specificity", as used herein, refers to the ability of a binding domain, in particular an immunoglobulin or an immunoglobulin fragment, such as a VHH or Nanobody, to bind preferentially to one antigen, versus a different antigen, and does not necessarily imply high affinity.

The term "preventing", as used herein, may refer to stopping/inhibiting the onset of a process, such as polymerization or (self-)assembly. It may also refer to stopping or blocking a disease or disorder (e.g., by prophylactic treatment). It may further mean to delay of the onset of polymerization, or in the meaning of the disease the onset of reduced frequency of symptoms, or reduced severity of symptoms associated with the disease or disorder (e.g., by prophylactic treatment). The term "inhibitory" as used in the phrase "inhibitory single domain antibody" or "inhibitory Nanobody" herein, refers to the fact that the Nanobody can inhibit the function and/or activity of its target protein. In case of Sap, this means that the Sap function to self-assemble or polymerize is inhibited or blocked and followed by *B. anthracis* cell growth being reduced, altered or inhibited. "Inhibitory" can mean full inhibition (no polymerization activity and/or multimerization is observable, or no S-Layer assembly, and even no *B. anthracis* growth is visible) or may mean partial inhibition (polymerisation to a certain degree, minimal S-Layer formed, or cell proliferation is normal to a certain degree). For instance, inhibition can mean 10% inhibition, 20% inhibition, 25% inhibition, 30% inhibition, 40% inhibition or more. Particularly, inhibition will be at least 50%, e.g. 50% inhibition, 60% inhibition, 70% inhibition, 75% inhibition, 80% inhibition, 90% inhibition, 95% inhibition or more. % inhibition typically will be evaluated against a suitable control (e.g. treatment with an irrelevant Nanobody), as will be readily chosen by the skilled person.

DETAILED DESCRIPTION

The *Bacillus anthracis* vegetative surface is covered by a two-dimensional paracrystalline protein array known as S-Layer (surface layer). Two mutually exclusive S-Layers sequentially appear at the cell surface in a growth phase-dependent manner: the Sap exponential layer, and EA1 stationary layer. The self-assembling characteristic of S-Layer proteins (SLPs) hampers their ease of handling under non-denaturing conditions and has hitherto proven prohibitive for structural and biophysical characterization. In order to address the self-polymerization issue, the expression and purification of native monomeric Sap was optimized using its shortened protein form for crystallization ('$Sap_c$', '$Sap^{216-814}$', or '$Sap^{AD}$' as used interchangeably further herein), lacking the cell-wall anchored SLH domain. The invention is based on the use of pure monomeric $Sap^{216-814}$ protein for immunization of llamas with the aim of obtaining Nanobodies (Nbs) specific for the monomeric form, with the intent of using anti-Sap Nbs as crystallization aid and bio-tools to inhibit the assembly of S-Layer in vivo. Nanobody selection, identification and purification was successfully accomplished to define a panel of Sap-specific Nbs, which were able to inhibit the in vitro polymerization of the *B. anthracis* Sap protein. Excitingly, when applied in vivo, the Sap assembly-inhibiting (SAI) Nanobodies were able to also perturb the *B. anthracis*' S-Layer integrity, in fact by effacing the pre-existing S-Layer, leading to S-Layer disruption/disintegration thereby severely affecting cell morphology and bacterial growth. The effects on cell morphology and *B. anthracis* growth were specific for those Nanobodies (Nbs) identified as inhibiting Sap S-Layer assembly in vitro. Importantly, the Sap S-Layer assembly inhibitory Nbs, when applied as treatment in mice going through a *B. anthracis* infection, resulted in the clearance of the ongoing infection and cured them of lethal anthrax disease. In conclusion, those Sap binding agents form promising candidates for the development of new strategies to fight anthrax disease.

The first aspect of the invention relates to a compound which specifically binds to a bacterial S-Layer protein (SLP), thereby preventing its polymerization, and furthermore effacing already existing bacterial S-Layer, which were generated from polymerizing SLPs. In a particular embodiment, a compound binding the Surface array protein (Sap) constituting the S-Layer of *B. anthracis* and preventing its polymerization or self-assembly is disclosed herein, moreover affecting the S-Layers made on the *B. anthracis* surface. Self-assembling proteins are known to spontaneously oligomerize or polymerize forming multimers, which eventually lead to aggregation, or structural assemblies such as the S-Layer. The present invention provides compounds that are binding to a monomeric and/or oligomeric form of the self-assembling SLP proteins, specifically, the *B. anthracis* Sap proteins. Though, also the EA1 protein of *B. anthracis* constitutes the S-Layer at some point, and furthermore, a number of pathogenic bacteria are known to contain an S-Layer, thereby indicating a conserved role for S-Layer proteins in their involvement in bacterial infection. So, targeting the complete S-Layer by provision of binders specific to said S-Layer proteins may therefore develop into a novel way to block bacterial infection. Via inhibition of polymerization of those S-Layer proteins in a certain bacterial growth stage, or even by disintegrating or effacing the S-Layers present on said S-Layer-containing bacteria, which will affect bacterial cell morphology and growth, the pathogen will eventually be killed. So one embodiment disclosed herein refers to a compound specifically binding and disintegrating the bacterial S-Layer wherein said S-Layer is derived from an 5-Layer-containing pathogen, more specifically from one selected from the list of *Bacillus* species (*B.*

*anthracis, B. cereus, B. thuringiensis*), *Clostridium difficile, Paenibacillus larvae, Caphylobacteri fetus, Campylobacter rectus, Tannerella forsythia, Aeromonas hydrophila, Rickettsia prowazekii, Rickettsia rickettsia, Rickettsia typhi, Serratia marcescens, Aeromonas salmonicida* and *Lactobacillus acidophilus*. Non-limiting examples so include *Bacillus cereus* causing food poisoning and *B. thuringiensis*, acting as an insecticide. Other gram positive bacteria constituting an S-Layer involve *Clostridium difficile* and *Paenibacillus larvae*, a human and animal (honey bee) pathogen, respectively. Further gram negative species with SLPs are *Caphylobacteri fetus, Campylobacter rectus, Tannerella forsythia, Aeromonas hydrophila, Rickettsia prowazekii, Rickettsia rickettsia, Rickettsia typhi*, and *Serratia marcescens* for instance, which are all pathogenic to humans. Animal pathogens presenting an S-Layer include *Aeromonas salmonicida* and *Lactobacillus acidophilus*. Furthermore, also some non-pathogenic bacteria such as *Geobacillus stearothermophilus* and *Caulobacter crescentus* have S-Layers, constituted by SbsB and RsaA, respectively (Baranova et al., 2014; and Bharat et al., 2017). For completeness, also see the listed S-Layer proteins identified in a number of bacteria in Table 1 of Sara and Sleytr (2000).

S-Layer proteins constituting the S-Layers in pathogens may in fact act similarly to Sap, and therefore targeting those SLPs is disclosed herein for development of novel antibacterials, which are, among other purposes, for instance applicable when antibiotics resistance pops-in, especially for the so called class of ESKAPE pathogens. *Campylobacter* for instance is on the high priority list of pathogens for R&D on new antibiotics.

The fact that compounds binding to and inhibiting polymerization of Sap are surprisingly also capable of depolymerizing the pre-existing Sap S-Layer is novel as it was never described for any known S-Layer binding agents so far. The state of the art disclosing SLP binding agents, such as conventional antibodies, peptides or single domain antibodies only revealed that such binding agents would be suitable in detection or diagnosing of bacterial infection, or as a kind of chaperone in crystallization of the S-Layer protein. Said compounds hence are suggested to possibly act in inhibition or interference of polymerization or SLP assembly, but not in depolymerization or disintegration of pre-existing S-Layers. This novel feature specific for the compounds of the invention allows to go beyond binding or detection of S-Layers, and use said binding agents for in vivo targeting of S-Layers to overcome bacterial infection due to negatively affecting the bacterial cell morphology and growth, as demonstrated here for *B. anthracis.*

In one particular example, the compounds specifically binding to SLPs relate to SLPs from S-Layer-containing pathogens such as the SlpA from *C. difficile*, encoding the S-Layer which is the predominant surface antigen on the *C. difficile* spore. The SlpA protein has been shown to induce a strong serum IgG response in patients (See Kelleher D. et al., J. Med. Micro., 55:69-83 (2006)). The protein is divided into an N-terminal (LMW) portion and a C-terminal (HMW) portion. The SlpA HMW protein is highly conserved and therefore attractive as a target. In fact, the S-Layer of *C. difficile* has been demonstrated to play a role in sporulation, toxin production and in resistance to lysozyme and anti-microbial peptide LL-37, both components of the innate immune system. However, an S-Layer null mutant of *C. difficile* was still able to colonize and persist in the hamster gut, despite a complete attenuation of virulence, but so without impact on cell viability (Kirk et al., 2017). Also Kandalaft et al. (2015) isolated SLP-specific VHHs to target the S-Layer of *C. difficile*, but those VHHs were only capable of affecting motility in vitro. No indication for in vivo efficacy or modulation of cell growth was reported, neither of protection against death. Moreover, the role for *C. difficile* SLPs in adhesion to the host and growth and survival has been disclosed, but so far no antibodies or other agents were identified that lead to effacing S-Layers resulting in a cure of *C. difficile* infection. The compounds of the invention targeting pre-existing S-Layers to result in disintegration were shown to attenuate bacterial growth and alter cell morphology. Hence the SLP-binding compounds of the invention provide for a unique interference mechanism on virulence and cell growth or colonization by affecting the S-Layer of such S-Layer-containing pathogens, leading to disintegration and survival of the host, which has not been observed before.

The term "disintegrating" as used herein, refers to a disruption or disassembling of a certain fixed structure, such as an S-Layer. In fact, the outcome of the S-Layer disintegration by the compounds of the invention will be that pre-existing multimeric Sap or SLP structures are broken down resulting in an effacing S-Layer. A skilled person can easily without undue burden prove or identify compounds specifically binding to an SLP capable of disintegrating the bacterial S-Layer. As exemplified in detail and described herein, an in vitro method may be applied using S-Layer-containing bacterial cells (isolated cells or bacteria itself), comprising the steps of visualizing said cells via microscopy, in particular electron microscopy to allow sensitivity and resolution required for S-Layer monitoring, following addition of the compound of interest binding to the SLP of said cells, and determine via a time-lapse experiments whether the S-Layer structure remains or falls apart, i.e. gets disintegrated due to the presence of said compound.

In one embodiment, said compound binding bacterial SLP proteins or in particular *B. anthracis* Sap to prevent SLP polymerization or to efface the S-Layer is a small entity compound. In fact, once the size of the compound is too large to penetrate to the S-Layer, the disintegration may not be possible anymore. So a cut-off in size for the compound is most likely required. Therefore, the compound of the invention is in one embodiment a small molecule compound. The term "compound" as used herein comprises organic or inorganic compounds, derived synthetically or from natural resources. The compounds include polynucleotides, lipids or hormone analogues that are characterized by low molecular weights. The term "small molecule", as used herein, refers to a low molecular weight (e.g., <900 Da or <500 Da) organic compound. In another embodiment, said compound is a peptide or peptidomimetic. Said compounds include small peptides or peptide-like molecules, peptidomimetics as called herein, comprising from about 2 to about 40 amino acids. In fact, in a specific embodiment, said compound of the invention is a peptide that is not part of the $Sap^{AD}$ proteins. Peptidomimetics are compounds whose essential elements (pharmacophore) mimic a natural peptide or protein in 3D space and which retain the ability to interact with the biological target and produce the same biological effect. Peptidomimetics are designed to circumvent some of the problems associated with a natural peptide: e.g. stability against proteolysis (duration of activity) and poor bioavailability. The design process begins by developing structure-activity relationships (SAR) that can define a minimal active sequence or major pharmacophore elements and identify the key residues that are responsible for the biological effect. Finally, larger polypeptides are encompassed by the invention, comprising from about 40 to about 500 amino acids, or from about 40 to about 400 amino acids, or to about 350 amino acids, or to about 300 amino acids, or to about 250 amino acids such as small entity antibodies or antibody conjugates. Alternatively, said compound of the invention is an antibody mimetic. In fact, a preferred embodiment provides said compound as an active antibody fragment, a single-domain antibody, or more specifically, a Nanobody. The compound of the invention for prevention of SLP protein polymerization and S-Layer disintegration in fact is preferably not a conventional antibody, since those larger molecules have been shown to most likely suffer from steric constraints, which prevents access to the S-Layer.

More particularly, embodiments are provided in which several Nanobodies binding to Sap where shown to inhibit polymerization as determined in a DLS assay and using EM (see Examples). Said method or assay allows a skilled person to select for the SLP binding agents that have the capacity to prevent polymerization. Specific embodiments relate to compounds of the present invention, which are Nbs, depicted in SEQ ID NO: 20-25. Crystallization of Sap using Nb684 and Nb694 allowed to determine how the Nbs depicted in SEQ ID NOs: 20-25 (Nb683, Nb688, Nb692, Nb702, Nb704, and Nb707) were bound to Sap: to which domains, and at which position when the Sap proteins are aligned in the S-Layer (see FIG. 4, 14). From the structure, as well as from the selected Nbs, it was found that the Sap protein domains 1, 2, 4, and 6 are potential targets of Nb compounds to inhibit polymerization and with the property to efface existing S-Layers. Indeed, said domains were shown to allow independent expression, allowing to be used as an antigen. With the term "protein domain", a distinct functional and/or structural unit in a protein is generally meant. Usually a protein domain is responsible for a particular function or interaction, contributing to the overall role of a protein. Domains may exist in a variety of biological contexts, where similar domains can be found in proteins with different functions. The Sap domains as annotated here, are structural units, each involved in typical interactions required for S-Layer assembly probably.

The identified Nanobodies involved in inhibitory activity of Sap assembly and disruption of S-Layers were shown to bind to domain 1 and/or domain 2 of Sap. One embodiment relates to compounds that bind a protein comprising said domains 1 and/or 2 sequences, SEQ ID NO: 6, or SEQ ID NO:7, respectively. Another embodiment relates to said compounds that bind a protein comprising the sequence of domain 4 or domain 6 of Sap, i.e. SEQ ID NO:9 or SEQ ID NO:11, resp., since it is very obvious from the structural determination of Sap that those domains constitute the intermolecular regions, which are therefore prone to destabilization by inhibiting compounds of self-assembly (see FIG. 4).

In a particular embodiment, the epitope of Nb684, which was used for the crystallization of Sap, constitutes a number of residues at the interface of domain 1 and 2, which therefore might form a candidate epitope to contribute to inhibition of self-assembly of Sap. So said particular embodiment provides compounds binding to residues 221-222, 271 to 276, residues 316-320, and 328-333 as depicted in SEQ ID NO:1. In a more specific embodiment, the compounds of the invention that prevent Sap assembly or polymerization, are provided by a compound that contains an immunoglobulin domain, such as an antibody fragment or antibody-derivative, or more specifically a Nanobody, wherein the sequence SGSIFR in CDR1 and YDYW in CDR3 are present. Specifically, according to Kabat numbering, SGSIFR starting at residue 25 of the Immunoglobulin domain, and YDYW ending at the typical 109 residue of CDR3. Both sequence stretches comprised in said CDR1 and CDR3, respectively, contribute to the Sap binding site required to inhibit its polymerization or assembly.

In an alternative embodiment, the Nanobody of the invention is a humanized variant of any of the Nanobodies comprising SEQ ID NO: 20, SEQ ID NO: 21, SEQ ID NO: 22, SEQ ID NO: 23, SEQ ID NO: 24, or SEQ ID NO: 25, or of a Nanobody comprising the sequence SGSIFR in CDR1 and YDYW in CDR3, or of a Nanobody binding the Sap residues 221-222, 271 to 276, residues 316-320, and 328-333 as depicted in SEQ ID NO:1. The humanized sequence variants should retain the favourable properties of the original VHH, which include antigen binding affinity, and biochemical and biophysical properties. It should be noted that the Nanobodies of the invention in their broadest sense are not limited to a specific biological source or to a specific method of preparation. For example, the nanobody of the invention can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "mutation" of a naturally occurring VHH domain to reduce binding to pre-existing antibodies, or by expression of a nucleic acid encoding such a mutated VHH domain; (5) by "camelization" of a naturally occurring VH domain from any animal species, and in particular from a mammalian species, such as from a human being, or by expression of a nucleic acid encoding such a camelized VH domain; (6) by "camelization" of a "domain antibody" or "Dab" as described in the art, or by expression of a nucleic acid encoding such a camelized VH domain; (7) by using synthetic or semisynthetic techniques for preparing proteins, polypeptides or other amino acid sequences known per se; (8) by preparing a nucleic acid encoding a Nanobody using techniques for nucleic acid synthesis known per se, followed by expression of the nucleic acid thus obtained; and/or (9) by any combination of one or more of the foregoing. It should be noted that humanized immunoglobulin single variable domains of the invention can be obtained in any suitable manner known per se (i.e. as indicated under points (1)-(9) above) and thus are not strictly limited to polypeptides that have been obtained using a polypeptide that comprises a naturally occurring VHH domain as a starting material. Humanized immunoglobulin single variable domains, in particular Nanobodies, may have several advantages, such as a reduced immunogenicity, compared to the corresponding naturally occurring VHH domains. By humanized is meant mutated so that immunogenicity upon administration in human patients is minor or non-existent. Such humanization generally involves replacing one or more amino acid residues in the sequence of a naturally occurring VHH with the amino acid residues that occur at the same position in a human VH domain, such as a human VH3 domain. Humanizing a single domain antibody or Nanobody according to the present invention comprises a step of replacing one or more of amino acids by their human counterpart as found for instance in the human consensus sequence, without that polypeptide losing its typical character, i.e. the humanization does not significantly affect the antigen binding capacity of the resulting polypeptide. The skilled person will be able to select humanizing substitutions or suitable combinations of humanizing substitutions which optimize or achieve a desired or suitable balance between the favourable properties provided by the humanizing substitutions on the one hand and the favourable properties of naturally occurring VHH domains on the other hand. A human consensus sequence can be used as target sequence for humanization, but also other means are known in the art. One alternative includes a method wherein the skilled person aligns a number of human germline alleles, such as for instance but not limited to the alignment of the IGHV3 alleles, to use said alignment for identification of residues suitable for humanization in the target sequence. Also a subset of human germline alleles most homologous to the target sequence may be aligned as starting point to identify suitable humanisation residues. Alternatively, the VHH is analyzed to identify its closest homologue in the human, and used for humanisation construct design. A humanisation technique applied to Camelidae VHHs may also be performed by a method comprising the replacement of specific amino acids, either alone or in combination. Said replacements may be selected based on what is known from literature, are from known humanization efforts, as well as from human consensus sequences compared to the natural VHH sequences, or the human alleles most similar to the VHH sequence of interest. As can be seen from the data on the VHH entropy and VHH variability given in Tables A-5-A-8 of WO 08/020079, some amino acid residues in the framework regions are more conserved between human and Camelidae than others. Generally, although the invention in its broadest sense is not limited thereto, any substitutions, deletions or insertions are preferably made at positions that are less conserved. Also, generally, amino acid substitutions are preferred over amino acid deletions or insertions. For instance, a human-like class of Camelidae single domain antibodies contain the hydrophobic FR2 residues typically found in conventional antibodies of human origin or from other species, but compensating this loss in hydrophilicity by other substitutions at position 103 that substitutes the conserved tryptophan residue present in VH from double-chain antibodies. As such, peptides belonging to these two classes show a high amino acid sequence homology to human VH framework regions and said peptides might be administered to a human directly without expectation of an unwanted immune response therefrom, and without the burden of further humanisation. Indeed, some Camelidae VHH sequences display a high sequence homology to human VH framework regions and therefore said VHH might be administered to patients directly without expectation of an immune response therefrom, and without the additional burden of humanization. Other VHH sequences in fact require humanization techniques to typically lead to a variant with favourable conditions to react with the target protein when administered to a subject.

In another aspect of the invention, a compound of the invention is used as a tool in structural analysis, so as to bind the SLP proteins, and thereby facilitate crystallography, cryo-EM, or as purification aid in stabilizing SLPs.

Another aspect of the invention relates to a compound specifically binding the bacterial SLP protein, in particular Sap, and inhibiting its self-assembly, and/or by such binding to the S-Layer initiate the disruption of already existing SLP aggregates, leading to inhibition of bacterial growth and infection, for use as a medicine. In particular the compound is used as a medicine to treat bacterial infection. The term "medicine" or "medicament", as used herein, refers to a substance/composition used in therapy, i.e., in the prevention or treatment of a disease or disorder. According to the invention, the terms "disease" or "disorder" refer to any pathological state, in particular to pathogenic infections, more particular to anthrax. In one particular embodiment, said compound of the invention is used to treat *B. anthracis* infection. The term "treatment" or "treating" or "treat" can be used interchangeably and are defined by a therapeutic intervention that slows, interrupts, arrests, controls, stops, reduces, or reverts the progression or severity of a sign, symptom, disorder, condition, or disease, but does not necessarily involve a total elimination of all disease-related signs, symptoms, conditions, or disorders. The term "treating" or "treatment" as stated throughout this document is used conventionally, e.g. the management or care of a subject for the purpose of combating, alleviating, reducing, relieving, improving the condition of a disease cited herein.

In another embodiment of the invention, said compound of the invention is used for diagnosing or detecting bacterial infection, particularly a *Bacillus* infection such as *B. anthracis* or *B. cereus* infection within a subject, through specific Sap detection using said compounds of the present invention. In a specific embodiment, the present invention provides a kit or assay kit, comprising said compound of the invention or a composition comprising said compound and means to allow detection of the bacteria or SLP or S-Layer in a sample. Such means may be buffers, labelling agents, mounting chips or devices, among other detection tools.

In other embodiments, the compounds of the invention specifically binding SLP protein, more particularly SLPs of an S-Layer-containing pathogen, for disruption of pre-existing S-Layers, for use as a medicine. For instance, but non-limiting, examples of pathogens with SLP proteins forming an S-Layer are: other *Bacillus* species, such as *B. anthracis*, causing anthrax disease, *B. cereus* causing food poisoning, and *B. thuringiensis*, acting as an insecticide, respectively. Other gram positive bacteria constituting an S-Layer involve *C. difficile* and *P. larvae*, a human and animal (honey bee) pathogen, respectively. Further gram negative species with SLPs are *C. fetus, C. rectus, T. forsythia, A. hydrophila, R. prowazekii, R. rickettsia, R. typhi* and *S. marcescens* for instance, which are all pathogenic to humans. Animal pathogens constituting an S-Layer include *A. salmonicida* and *L. acidophilus.*

Finally, in one embodiment, said compounds of the present invention will also inhibit *B. cereus* Sap polymerization, as the protein of *B. cereus* is 95% conserved as compared to the *B. anthracis* sequence. In specific embodiments, said compounds are used as a medicament, and specifically for treatment of *B. cereus* infection.

A patient, for the purpose of this invention, is an animal, a mammal, including a human, in need of treatment for a bacterial pathogen infection, such as anthrax (which is caused by *Bacillus anthracis* infection). Therefore, the present invention includes compositions such as pharmaceutical or vaccine compositions that are comprised of a pharmaceutically acceptable carrier and a pharmaceutically effective amount of the compound of the present invention, the protein for vaccination, or salt thereof of the present invention. Said composition may hence by used as a medicine, or for use in treating bacterial infection, for S-Layer-containing pathogens, or in particular for use in treatment of *B. anthracis* infection. Said composition may also be used in diagnostic purposes as mentioned herein, or applied as a tool in structural analysis, as disclosed herein. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound of the invention or salt thereof is preferably that amount which produces a result or exerts an influence on the subject infected with anthrax. The compound of the present invention can be administered with pharmaceutically-acceptable carriers well known in the art using any effective conventional dosage unit forms, including immediate, slow and timed-release preparations, or repeated dosage forms, orally, parenterally, topically, nasally, ophthalmically, optically, intrathecally, intracerebroventricularly, sublingually, rectally, vaginally, via inhalation, and the like.

In fact, a further aspect of the invention relates to said compounds of the invention comprising a half-life extension, such as for instance a serum albumin binding single domain antibody. Currently, half-life extension (HLE) of biotherapeutics is dominated by strategies utilizing albumin binding or fusion, fusion to an immunoglobulin Fc region and PEGylation. Due to the possibility that steric hindrance affects the potency and efficacy of the compound to reach the S-Layer, the compounds comprising also a half-life extension entity should remain as small as possible. Hence, the use of for instance serum albumin binding VHHs for half-life extension or increased half-life for the compound is certainly a very auspicious application of said invention. In fact, the compound or small entity compound of the invention is provided in this case by linking or coupling the compound to the half-life extension. In a particular case, the HLE is a serum albumin binding compound, which can basically be any type of molecule, and preferably is a protein, or more particularly comprises an IVD. Said coupling or linking may be directly or via a linker. So, in a particular embodiment, the invention relates to a compound of the invention, comprising an SLP binding agent linked to a half-life extension, in particular, linked to a Serum albumin binding agent.

A "composition" of the invention may be provided in form of a kit comprising a first container comprising (lyophilised) compound and a second container comprising a solution for resuspension of the lyophilised compound, such as proteins. The protein powder may comprise one or more lyoprotectants such as sucrose, dextran, sorbitol and amino acids to stabilise the protein during lyophilisation. Alternatively, the composition is provided in a single container comprising the compound in suspension or solution. Either solution may contain one or more excipient(s). The solutions are typically water-based. Therefore, purified water may form the main excipient. For example, dilution of the protein to give the desired final concentration will usually be performed with water for injection (WFI). The solution typically contains a buffer. Therefore, further excipients include buffering agents and pH regulators such as sodium citrate, sodium dihydrogen phosphate monohydrate, and sodium hydroxide. In some instances, a thickening agent such as xanthan may be present as a further excipient. A surfactant, in particular a non-ionic surfactant such as polysorbate 80, may also be present. Other excipients include sucrose, sorbitol, inorganic salts, amino acids and vitamins.

This invention also relates to "pharmaceutical compositions" comprising one or more compounds of the invention, or a mixture comprising at least one or more compounds according to the invention. Said mixture represents a combination of active compounds affecting the same or different SLP proteins of one or more bacterial species. In fact, in *B. anthracis*, a mixture of compounds binding Sap and EA1 SLP proteins may be beneficial in targeting any S-Layer formation during bacterial growth. Alternatively, a mixture of a compound targeting the S-Layer of one pathogen and another compound targeting the S-Layer of another pathogen may be combined in one composition, as to use in a broader application for treatment or prevention of disease. Another embodiment discloses the composition comprising at least one compound binding the S-Layer of a pathogen, and at least one compound binding a toxin of said pathogen. So, in a particular embodiment, the pharmaceutical composition comprises a single or a mixture of compounds with at least one compound according to the invention and a pharmaceutically acceptable carrier or diluent. These pharmaceutical compositions can be utilized to achieve the desired pharmacological effect by administration to a patient in need thereof. The present invention includes pharmaceutical compositions that are comprised of a pharmaceutically acceptable carrier and a pharmaceutically effective amount of a compound, or salt thereof, of the present invention. A pharmaceutically effective amount of compound is preferably that amount which produces a result or exerts an influence on the particular condition being treated. In general, "therapeutically effective amount", "therapeutically effective dose" and "effective amount" means the amount needed to achieve the desired result or results. One of ordinary skill in the art will recognize that the potency and, therefore, an "effective amount" can vary depending on the identity and structure of the compound of the invention. Also the number of doses over time needed to cure from infection may determine the "therapeutically effective amount". One skilled in the art can readily assess the potency of the compound. By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Such ingredients and procedures include those described in the following references, each of which is incorporated herein by reference: Powell, M. F. et al. ("Compendium of Excipients for Parenteral Formulations" PDA Journal of Pharmaceutical Science & Technology 1998, 52(5), 238-311), Strickley, R. G ("Parenteral Formulations of Small Molecule Therapeutics Marketed in the United States (1999)-Part-1" PDA Journal of Pharmaceutical Science & Technology 1999, 53(6), 324-349), and Nema, S. et al. ("Excipients and Their Use in Injectable Products" PDA Journal of Pharmaceutical Science & Technology 1997, 51 (4), 166-171).

The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, stabilizing agents, flavouring agents or colorants. A "diluent", in particular a "pharmaceutically acceptable vehicle", includes vehicles such as water, saline, physiological salt solutions, glycerol, ethanol, etc. Auxiliary substances such as wetting or emulsifying agents, pH buffering substances, preservatives may be included in such vehicles.

The compounds of the invention and a pharmaceutically acceptable carrier can be administered with non-immunogenic pharmaceutically acceptable carriers well known in the art using any effective conventional dosage form, including immediate, slow and timed release preparations, and can be administered by any suitable route such as any of those commonly known to those of ordinary skill in the art. For therapy, the pharmaceutical composition of the invention can be administered to any patient in accordance with standard techniques.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch. In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both. Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate. The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents. Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin. Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents. The compounds of this invention may also be administered parenterally, that is, subcutaneously, intravenously, intraocularly, intrasynovially, intramuscularly, or intraperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quaternary ammonium salts, as well as mixtures. The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Finally, for inhalation routes of administration, aerosol devices may be applied comprising the compound or composition of the invention.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51 (4), 166-171.

Commonly used pharmaceutical ingredients that can be used as appropriate to formulate the composition for its intended route of administration include:

- acidifying agents (examples include but are not limited to acetic acid, citric acid, fumaric acid, hydrochloric acid, nitric acid); alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine); adsorbents (examples include but are not limited to powdered cellulose and activated charcoal); aerosol propellents (examples include but are not limited to carbon dioxide, $CCl_2F_2$, $F_2ClC—CClF_2$ and $CClF_3$) air displacement agents (examples include but are not limited to nitrogen and argon); antifungal preservatives (examples include but are not limited to benzoic acid, butylparaben, ethylparaben, methylparaben, propylparaben, sodium benzoate); antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal); antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (examples include but are not limited to block polymers, natural and synthetic rubber, polyacrylates, polyurethanes, silicones, polysiloxanes and styrene-butadiene copolymers); buffering agents (examples include but are not limited to potassium metaphosphate, dipotassium phosphate, sodium acetate, sodium citrate anhydrous and sodium citrate dihydrate) carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection) chelating agents (examples include but are not limited to edetate disodium and edetic acid) colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);
- clarifying agents (examples include but are not limited to bentonite);
- emulsifying agents (examples include but are not limited to acacia, cetomacrogol, cetyl alcohol, glyceryl monostearate, lecithin, sorbitan monooleate, polyoxyethylene 50 monostearate);
- encapsulating agents (examples include but are not limited to gelatin and cellulose acetate phthalate);
- flavorants (examples include but are not limited to anise oil, cinnamon oil, cocoa, menthol, orange oil, peppermint oil and vanillin);
- humectants (examples include but are not limited to glycerol, propylene glycol and sorbitol);
- levigating agents (examples include but are not limited to mineral oil and glycerin);
- oils (examples include but are not limited to arachis oil, mineral oil, olive oil, peanut oil, sesame oil and vegetable oil);
- ointment bases (examples include but are not limited to lanolin, hydrophilic ointment, polyethylene glycol ointment, petrolatum, hydrophilic petrolatum, white ointment, yellow ointment, and rose water ointment);
- penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)
- plasticizers (examples include but are not limited to diethyl phthalate and glycerol);
- solvents (examples include but are not limited to ethanol, corn oil, cottonseed oil, glycerol, isopropanol, mineral oil, oleic acid, peanut oil, purified water, water for injection, sterile water for injection and sterile water for irrigation);
- stiffening agents (examples include but are not limited to cetyl alcohol, cetyl esters wax, microcrystalline wax, paraffin, stearyl alcohol, white wax and yellow wax);
- suppository bases (examples include but are not limited to cocoa butter and polyethylene glycols (mixtures);

- surfactants (examples include but are not limited to benzalkonium chloride, nonoxynol 10, oxtoxynol 9, polysorbate 80, sodium lauryl sulfate and sorbitan monopalmitate);
- suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);
- sweetening agents (examples include but are not limited to aspartame, dextrose, glycerol, mannitol, propylene glycol, saccharin sodium, sorbitol and sucrose);
- tablet anti-adherents (examples include but are not limited to magnesium stearate and talc);
- tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
- tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
- tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
- tablet direct compression excipients (examples include but are not limited to dibasic calcium phosphate);
- tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);
- tablet glidants (examples include but are not limited to colloidal silica, corn starch and talc);
- tablet lubricants (examples include but are not limited to calcium stearate, magnesium stearate, mineral oil, stearic acid and zinc stearate);
- tablet/capsule opaquants (examples include but are not limited to titanium dioxide);
- tablet polishing agents (examples include but are not limited to carnuba wax and white wax);
- thickening agents (examples include but are not limited to beeswax, cetyl alcohol and paraffin);
- tonicity agents (examples include but are not limited to dextrose and sodium chloride);
- viscosity increasing agents (examples include but are not limited to alginic acid, bentonite, carbomers, carboxymethylcellulose sodium, methylcellulose, polyvinyl pyrrolidone, sodium alginate and tragacanth); and
- wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A between 0.01-5 mg/mL solution of the desired compound of this invention can be made using sterile, injectable water, and the pH is adjusted if necessary. The solution is diluted for administration to 0.02-2 mg/mL with sterile 5% dextrose and is administered as an IV infusion over about 60 minutes.

Lyophilised powder for IV administration: A sterile preparation can be prepared with (i) 1-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

0.01-5 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 1-100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 1-100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 1-100 mg of active ingredient, 0.2 mg of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration:

Based upon standard laboratory techniques known to evaluate compounds useful for the treatment of diseases cited herein, by standard toxicity tests and by standard pharmacological assays for the determination of treatment of the conditions identified above in mammals, and by comparison of these results with the results of known medicaments that are used to treat anthrax, the effective dosage of the compounds of this invention can readily be determined for treatment of anthrax. The amount of the active ingredient to be administered in the treatment can vary widely according to such considerations as the particular compound and dosage unit employed, the mode of administration, the period of treatment, the age and sex of the patient treated, and the nature and severity of the anthrax infection treated.

The total amount of the active ingredient to be administered will generally range from about 0.001 mg/kg to about 200 mg/kg body weight per day, and preferably from about 0.01 mg/kg to about 50 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight. The average daily oral dosage regimen will preferably be from 0.01 to 100 mg/kg of total body weight. The average daily intrathecal dosage regimen will preferably be from 0.01 to 100 mg/kg of total body weight.

It is evident for the skilled artisan that the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination of the Pharmaceutical Compositions of the Invention with Antibiotics for the Treatment of Anthrax and Other Agents Before October 2001, the first-line treatment of anthrax infection and prophylaxis was penicillin; however, this is not the case for bioterrorism-related cases because of the concern for genetically engineered penicillin-resistant anthrax strains. The Centre for Disease Control and Prevention (CDC) recommends ciprofloxacin or doxycycline. Doxycycline should not be used in suspected meningitis because it has poor penetration of the central nervous system. Quinolones are not routinely indicated for pediatric patients because of the risk of musculoskeletal disorders. However, in 2008, the US Food and Drug Administration (FDA) approved the use of levofloxacin in children as young as 6 months for the treatment of inhalational (and inhalational exposure to) anthrax. Treatment duration is 60 days, but safety has not been evaluated beyond 14 days. Pregnant women or woman on breastfeeding can use amoxicillin. Resistance exists to third-generation cephalosporins, trimethoprim, and sulfisoxazole. For patients with severe anthrax, therapy with corticosteroids and intravenous antibiotics is recommended. Individuals with inhalational anthrax should receive a multidrug regimen of either ciprofloxacin or doxycycline along with at least one more agent, including a quinolone, rifampin, tetracycline, vancomycin, imipenem, meropenem, chloramphenicol, clindamycin, or an aminoglycoside. After susceptibility testing and clinical improvement, the regimen may be altered.

Raxibacumab, a monoclonal antibody directed at the protective antigen of *B. anthracis*, is available from the CDC for treatment of inhalational anthrax in adults and children. It is used as part of a combination regimen with appropriate antibiotic drugs. It is also approved for prophylaxis of inhalational anthrax when alternative therapies are not available or not appropriate.

Human anthrax immune globulin (Anthrasil) is indicated for treatment of inhalational anthrax in adults and children in combination with antibiotic therapy.

Cases of gastrointestinal and cutaneous anthrax can be treated with ciprofloxacin or doxycycline for 60 days. Penicillin such as amoxicillin or amoxicillin-clavulanate may be used to complete the course if the strain is susceptible.

It is to be understood that although particular embodiments, specific configurations as well as materials and/or molecules, have been discussed herein for engineered cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Anthrax is an ancient and deadly disease caused by the Gram-positive spore-forming bacterial pathogen *B. anthracis*. Today, anthrax mostly affects wildlife and livestock, but remains a concern for human public health primarily in persons handling contaminated animal products and as a bioterror threat due to the high resilience of spores, the high case-fatality rate even with the aggressive use of antibiotics, and the lack of a civilian vaccine program (Jernigan et al., 2002; Sweeney et al., 2011). The bacterium's cell surface is covered by a protective paracrystalline monolayer composed of the S-Layer proteins Sap or EA1. In the following examples, we demonstrate the generation of nanobodies to inhibit Sap self-assembly, the determination of the structure of the Sap S-Layer assembly domain ($Sap^{AD}$) and we show that S-Layer disintegration inhibits *B. anthracis* growth and anthrax pathology in vivo. $Sap^{AD}$ is found to consist of 6 beta-sandwich domains that fold and support S-Layer formation independently of calcium. Sap inhibitory nanobodies prevented Sap assembly and depolymerized existing Sap S-Layers in vitro. In vivo, nanobody-mediated effacement of the Sap S-Layer resulted in severe morphological defects and attenuated bacterial growth. Subcutaneous delivery of Sap inhibitory nanobodies cleared *B. anthracis* infection and prevented lethality in a mouse model of anthrax disease. These examples expose disruption of S-Layer integrity as a mechanism with therapeutic potential in S-Layer carrying pathogens. Finally, also examples of S-Layer disintegration in other bacterial species are considered as a novel mechanism for antibacterial development.

Example 1. *B. anthracis* Surface S-Layer

As part of its immune evasion strategy, *B. anthracis* presents a dynamic and complex cell surface. Atop a ~40 nm thick peptidoglycan cell wall, the vegetative bacilli are covered by one of two distinct proteinaceous paracrystalline arrays known as Surface layer or S-Layer (FIG. 14*a*)(Couture-Tosi et al., 2002). In response to host-derived signals, *B.*

*anthracis* becomes fully virulent by secretion of the anthrax exotoxins, ultimately leading to local or life-threatening systemic disease (Weiner and Glomski, 2012), and the expression of a poorly immunogenic and antiphagocytic poly-γ-D-glutamic acid (PGA) capsule (Collier & Young, 2003; Zwartouw & Smith, 1956; Makino et al., 1989). The latter is covalently attached to the peptidoglycan layer and crosses the porous S-Layer to extend as 100-200 nm long fibers from the cell surface (FIG. 14*a*) (Candela et al., 2005). S-Layers compose the cell surface of a range of different Bacteria and near all Archea (Sara & Sleytr, 2000). They have proposed roles as exoskeleton, protection against harmful environments, scaffolding structure for surface-localized enzymes and adhesins, molecular sieve for nutrient uptake and form a contact zone with the extracellular environment, including host cells in case of pathogenic bacteria (Gerbino et al., 2015). In *B. anthracis*, mutually exclusive S-Layers composed of surface array protein (Sap) or extractable antigen 1 (EA1) sequentially appear at the cell surface during exponential and stationary growth phases, respectively (Mignot et al., 2002). Although together with the PDGA capsule the two S-Layer proteins (SLPs) are the primary contact area between the bacterium and its environment, little is known about their structure and function. Strains with either or both S-Layer proteins deleted are viable when grown in vitro in rich culture media despite reported cell division defects in a sap deletion mutant that increased cell size by up to 20-fold relative to the wildtype strain (Mesnage et al., 1997; Kern et al., 2012). However, the virulence of S-Layer deletion mutants in the context of live anthrax infection has not been examined. To interrogate the physiological role of Sap, the major *B. anthracis* SLP associated with vegetative growth, we used camelid single domain antibodies, also named nanobodies, as a tool to inhibit SLP polymerization.

Sap is an ~800 residue protein highly conserved in *B. anthracis, B. cereus* and *B. thuringiensis*, with 80% average pairwise sequence identity among different isolates. An N-terminal signal peptide directs Sap to the cell surface, where it binds a ketal-pyruvylated ManNac unit in the peptidoglycan via an α-helical cell wall anchoring domain that consists of three S-Layer homology (SLH) regions (FIG. 14*b*) (Kern et al., 2011; Sychantha et al., 2018). The region corresponding to the predicted S-Layer assembly domain ($Sap^{AD}$; residues 216-814; Candela et al., 2005) was cloned for recombinant expression in *E. coli*. Recombinant $Sap^{AD}$ was isolated as soluble protein, purified and used for immunization of a llama and the selection of 20 unique Sap-binding nanobodies. A combinatorial screen of $Sap^{AD}$-nanobody complexes resulted in a set of two, $Nb^{AF684}$ and $Nb^{AF694}$, that together allowed crystallization and structure determination of $Sap^{AD}$ to 2.7 Å resolution.

Figure 1:
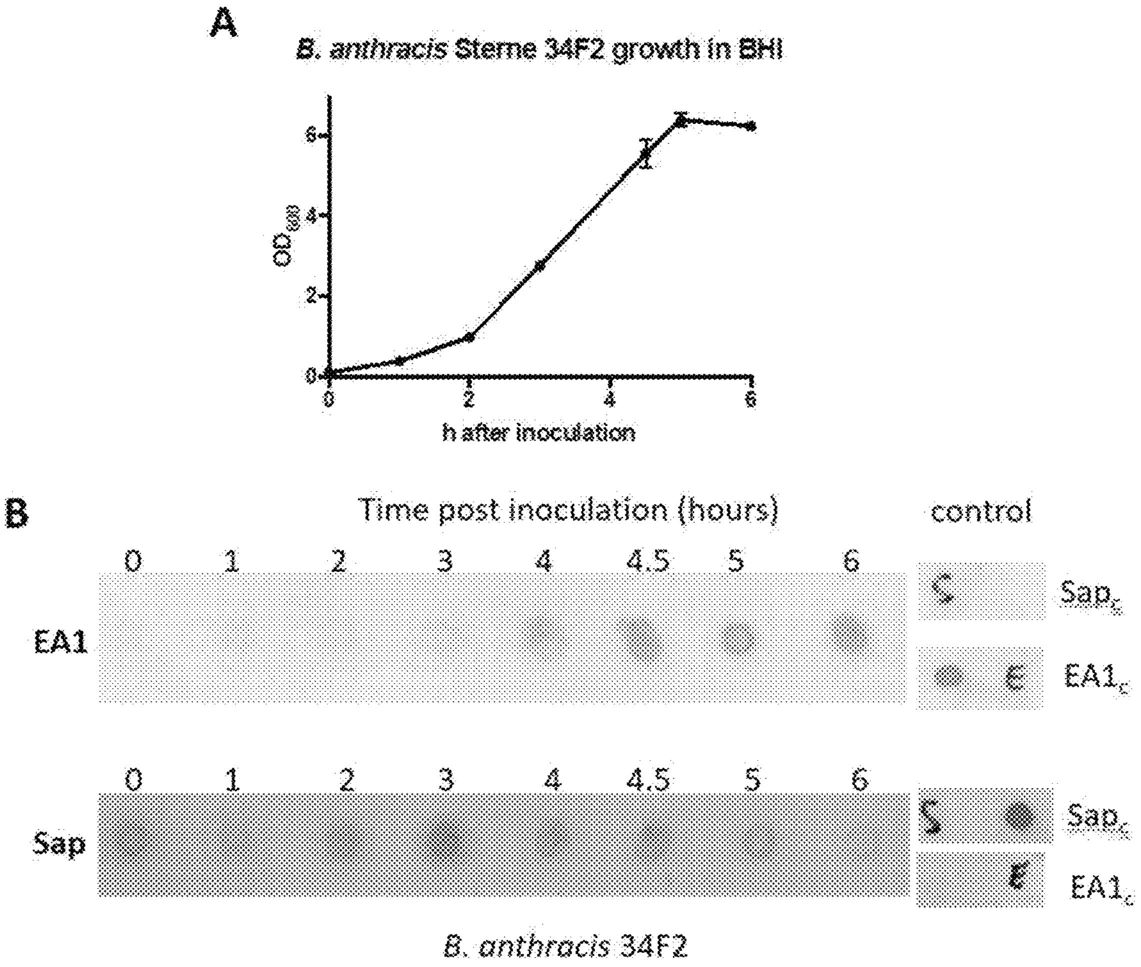
FIG. 1. Presence of Sap and EA1 S-Layers during *B. anthracis* growth.

Also see FIG. 1: Presence of Sap and EA1 S-Layers during *B. anthracis* growth (A) Growth curve of *B. anthracis* 34F2 (labelled 34F2) in BHI medium at 37° C., starting from an $OD_{600}$ 0.1 inoculum and monitored microscopically. Data represent three biological replicas and are plotted as $OD_{600nm}$ in the growth well (See FIG. 10). The growth curve shows exponential growth of the culture during the first 5 to 6 hours (h) post inoculation, before reaching confluency.

(B) During the first 6 hours post inoculation of a *B. anthracis* 34F2 culture, expression levels of the Sap and EA1 S-Layer proteins were monitored using whole cell dot blot and anti-Sap or anti-EA1 mouse polyclonal antibodies. Saps or EA1s represent spotted purified EA1 or Sap protein as positive controls for antibody specificity. The experiment shows that during the first 3 hours post inoculation (i.e. corresponding to the exponential growth phase), cells almost exclusively express the Sap S-Layer, which is gradually replaced by an EA1 S-Layer from 4-5 hours onwards, i.e. upon reaching stationary phase.

Also see FIG. 2: Recombinant production and self-assembly of *B. anthracis* Sap (A) For in vitro polymerization studies and structure determination, we generated a synthetic gene fragment encoding residues 216-814 ($Sap^{216-814}$ or $Sap_c$ or $Sap^{AD}$) of the *B. anthracis* Sap protein (Uniprot ID: P49051, SEQ ID NO:1) as a C-terminal His-tagged protein (SEQ ID NO:4). The N-terminal ~215 residues contain a pseudorepeat of three S-Layer Homology domains (SLH), which form a discrete folding unit that is responsible for the binding of Sap to the *B. anthracis* cell wall (PDB entry 3PYW; Kern et al. 2011). For this study, this N-terminal cell wall attachment domain was not included in the Sap fragment generated for recombinant protein production and structural studies. The resulting His-tagged Sap fragment (hereafter called $Sap^{216-814}$ or $Sap_c$ or $Sap^{AD}$; SEQ ID NO:4) was expressed in *E. coli* BL21 and purified to homogeneity by consecutive Ni-affinity chromatography and size exclusion chromatography. SDS-PAGE analysis shows the $Sap^{216-814}$ fragment can be isolated as a stable soluble protein.

(B) Analysis of particle size distribution in the purified $Sap^{216-814}$ fragment at 0 h and 24 h post purification, monitored by dynamic light scattering (DLS). DLS reveals that the $Sap^{216-814}$ fragment can be freshly purified as a monodisperse particle corresponding to a monomer. Over a 24 h period, the purified sample will start to assemble into a polydisperse high molecular weight species and turn the $Sap^{216-814}$ solution into an opaque, highly viscous gel.

(C) The nature of the high molecular weight particles present in the purified $Sap^{216-814}$ after a 24 h incubation was analysed by negative stain (C) and cryogenic (D) electron microscopic analysis. The electron micrographs show sheet-like particles a repetitive structure, indicative of S-Layer formation. The "power spectrum" or Fourier transform (D; inset) of representative sheets shows a strong and unique diffraction lattice, confirming the 2D crystalline nature of the particles and demonstrating that the oligomerization of the purified $Sap^{216-814}$ corresponds to the in vitro self-assembly into 2D arrays with equivalent morphology and cell parameters as the in vivo Sap S-Layer (Couture-Tosi et al., 2002). Thus, the $Sap^{216-814}$ fragment is self-sufficient as S-Layer assembly domain or "crystallization domain" and contains all required protein regions for the self-assembly of the Sap S-Layer.

Example 2. Domain Organization and X-Ray Structure of *B. anthracis* Sap

Our analysis showed that $Sap^{AD}$ consists of six beta-sandwich domains (D1-D6) connected via short linkers (FIG. 14*c*; FIG. 18). Domains D1 (residues 216-296) and D2 (residues 297-384) give rise to an L-shaped structure with an interdomain interface burying an 322 $Å^2$ surface area comprising 6 and 2 conserved H-bonds and hydrophobic contacts, respectively. $Nb^{AF684}$ and $Nb^{AF694}$ bind the D1-D2 hinge and the D1 domain respectively (FIG. 14*d*; FIG. 19). The D1-D2 'arm' is connected via a flexible linker to a central tile-shaped $Sap^{AD}$ 'body' formed by domains D3 to D6 (FIG. 14*c*). A hinge region between D4 and D5 gives rise to pairwise alignment of D3 and D6, and D4 and D5, respectively, an interface that buries 962 $Å^2$ surface area and contains, respectively, 14 and 6 conserved H-bonds and charge interactions, as well as 7 hydrophobic contacts (FIGS. 14*c, d*; FIG. 20*a*). Together, the $Sap^{AD}$ arm and body form a flat supertertiary structure of 70 Å by 130 Å (FIG. 14*c*). SAXS analysis showed this domain organization is retained in solution (FIG. 20*b,c*). Unlike bacterial SLPs of known structure (*Geobacillus stereathermophilus* SbsB (Baranova et al., 2014) and *Caulobacter crescentus* RsaA (Bharat et al., 2017)), folding of the individual domains or their condensation into the tile-like supertertiary structure of $Sap^{AD}$ does not show any requirement for calcium binding. Purified $Sap^{AD}$ readily aggregates into high molecular weight species, also in the absence of free calcium (FIG. 15*a*). Examination of $Sap^{AD}$ aggregates via negative stain transmission electron microscopy (nsTEM) showed these consist of tubules and two-dimensional sheets with a uniform lattice with P2 symmetry and unit cell vectors of a=210 Å, b=89 Å and γ=83° (FIG. 15*b*). Unit cell parameters in Sap S-Layers measured on deflated *B. anthracis* cells are a=184 Å, b=81 Å and γ=84 (Weiner and Glomski, 2012), suggesting that the tubules and 2D sheets seen in $Sap^{AD}$ solutions represent the subunit packing as found in native Sap S-Layers. The ~10% difference in vector length may represent a shrinkage of the unit cell in nsTEM of surface bound S-Layer on deflated cells versus cryoTEM on solution dispersed $Sap^{AD}$ S-Layer, or a small rearrangement due to the missing attachment domain in the latter. Observed $Sap^{AD}$ tubules have a diameter ranging from 50 to 300 nm, approaching the average ~1.3 μm width of *B. anthracis* cells. The intrinsic curvature in the lattice of the $Sap^{AD}$ tubules may be representative of that found on the bacterial cell surface.

Also see FIG. 3: Domain organization and X-ray structure of *B. anthracis* Sap.

(A) Schematic representation of the domain organization of *B. anthracis* Sap (SEQ ID NO:1; Uniprot ID: P49051). The N-terminal ~215 residues contain a pseudorepeat of three S-Layer Homology domains (SLH), which form a discrete folding unit that is responsible for the binding of Sap to the *B. anthracis* cell wall (PDB entry 3PYW; Kern et al. 2011). The X-ray structure $Sap^{216-814}$ as presented in panel B reveals that the Sap S-Layer comprises six independent domains (labelled D1-D6), with following domain boundaries: D1: 216-295 (SEQ ID NO:6), D2: 296-384 (SEQ ID NO:7), D3: 384-490 (SEQ ID NO:8), D4: 491-595 (SEQ ID NO:9), D5: 596-706 (SEQ ID NO:10) and D6: 707-814 (SEQ ID NO:11).

(B) As shown by DLS in FIG. 2, the $Sap^{216-814}$ fragment will undergo spontaneous self-assembly into Sap S-Layer like 2D crystals in a matter of hours. This S-Layer assembly potentially hampers 3D crystallization required for structure determination. To control this self-assembly step, we generated a set of camelid single domain antibodies or Nanobodies to be used as crystallization aide. For the model S-Layer protein SbsB from *Geobacillus stearothermophilus*, we have shown that Nanobodies can enable S-Layer protein 3D crystallization by binding the S-Layer protein monomers and blocking their intermolecular contact surfaces, thereby inhibiting S-Layer assembly (Baranova et al. 2012). Using a similar approach, we generated a set of Nanobodies against the *B. anthracis* Sap S-Layer protein for the use as crystallization aids. These Nanobodies were tested for their ability to stabilize monomeric $Sap^{216-814}$ and/or facilitate 3D crystallization of the protein. Two Nanobodies, Nb684 (SEQ ID NO:18) and Nb694 (SEQ ID NO:19) were found to facilitate formation of well-ordered 3D crystals amenable to X-ray diffraction and structure determination to a resolution of 2.95 Å. Panel B shows the ribbon representation of the X-ray structure of $Sap^{216-814}$ as disclosed in this document. The Sap S-Layer assembly domain (residues 216-814; as depicted in SEQ ID NO:4) comprises six independent immunoglobulin-like domains that assembly into a flat, tile-like unit resembling a laying number "6". The Nanobodies used as crystallization aides bind two independent epitopes in D1 (Nb694) and the D1-D2 interface (Nb684) (see FIG. 6).

(C) Based on the domain architecture revealed by the $Sap^{216-814}$ X-ray structure, we constructed synthetic gene fragments encoding Sap fragments corresponding to domains D1 (SEQ ID NO:6), D2 (SEQ ID NO:7), D3 (SEQ ID NO:8), D4' (SEQ ID NO:26), D5 (SEQ ID NO:10) and D6 (SEQ ID NO:11). Each of these fragments includes the domain residues of Sap, and is additionally modified to contain a C-terminal 6-His/EPEA tag to allow easy purification by Ni-affinity chromatography. When expressed in *E. coli* BL21 these gene fragments result in the production of stable protein fragments corresponding to domains D1, D3, D4', and D6, which can be purified to homogeneity by consecutive Ni-affinity and size exclusion chromatography. These purified Sap domain fragments can be stored as stable, soluble and monomeric proteins that do not undergo the self-assembly seen for the full Sap S-Layer assembly domain $Sap^{216-814}$. Unlike full-length Sap or $Sap^{216-814}$ these domains are used to produce stable, storage-compatible and stock-piling compatible solutions of monomeric Sap fragments.

Also see FIG. 4: Structural model of *B. anthracis* Sap S-Layer lattice.

The $Sap^{216-814}$ X-ray structure (shown in surface or ribbon representation) can be unambiguously docked as a rigid unit into a 2D projection map calculated from the EM-analysis of Sap S-Layers isolated from *B. anthracis* (Couture-Tosi et al. 2002). The docking of the $Sap^{216-814}$ X-ray structure in the S-Layer projection map provides insight into the inter-protomer contact zones that drive and stabilize the Sap S-Layer assembly. Within the Sap protomers, domains D3, D4, D5 and D6 fold back on each other to form a rigid unit that packs sideways through intermolecular contacts between D4 and D6. The S-Layer projection density shows that in the S-Layer, domains D1 and D2 support the lattice formation by lateral intermolecular contacts. The docked $Sap^{216-814}$ X-ray shows a small deviation from the S-Layer projection density at the height of domain D1, indicating that D1 undergoes a small rotational rearrangement around the D1-D2 linker when assembling into the Sap S-Layer. In the $Sap^{216-814}$ X-ray structure, the D1-D2 orientation within the Sap monomers is influenced by the Nb684 Nanobody that was used as crystallization aid. Nb684 binds the D1-D2 hinge region (see FIG. 6), locking the D1 and D2 into a fixed orientation. Based on the projection map of the Sap S-Layer, the D1 undergoes an outward rotation during S-Layer assembly. By stabilizing the inward rotation orientation of the D1-D2 contact, Nb684 is likely to inhibit Sap S-Layer assembly.

Example 3. Nanobodies as Crystallization Aid or S-Layer Assembly Inhibitor of *B. anthracis* Sap To facilitate the 3D crystallization and structure determination of the *B. anthracis* Sap S-Layer assembly domain ($Sap^{216-814}$), a number of camelid single domain antibodies were generated. A set of 20 different anti-Sap Nanobodies was isolated from a Nanobody (VHH) phage library generated from a llama immunized with $Sap^{216-814}$. Of those Nbs, $Nb^{AF684}$ and $Nb^{AF694}$ facilitated crystallization of $Sap^{AD}$ by providing additional lattice contacts and slowing down polymerization of the protein. When systematically screening the twenty isolated Sap binding Nbs, we found six that maintained the protein in a monomeric form for extended times (at least 7 days; FIG. 15*c*). Addition of a 15 μM cocktail of five of these Sap Assembly Inhibitory Nbs ($Nbs^{SAI}$: $Nb^{AF683}$, $Nb^{AF692}$, $Nb^{AF702}$, $Nb^{AF704}$ and $Nb^{AF707}$, 3 μM each; $Nb^{AF688}$ was not included due to its high aggregation propensity) led to a rapid reduction in tubule length and number density, resulting in the full dissolution of $Sap^{AD}$ polymers in a matter of minutes (FIG. 15*d, e*). Equivalent concentrations of a control Nb that binds an unrelated target (Nb11) neither blocked Sap S-Layer assembly, nor had an effect on tubule length or number (FIG. 15*g, f*). Follow-up studies indicated that 15 μM of a single representative inhibitory nanobody ($Sap^{AF692}$) led to $Sap^{AD}$ tubule dissolution in a timeframe corresponding to that of the $Nbs^{SAI}$ cocktail (FIG. 21*a*). Thus, in addition to blocking $Sap^{AD}$ polymerization, SAI nanobodies can depolymerize existing Sap lattices. Strikingly, the depolymerization activity of $Nbs^{SAI}$ appeared to be specific to their single domain antibodies. Sera obtained from mice or the llama that had been immunized with monomeric $Sap^{AD}$ and used to isolate Sap nanobodies, suppressed de novo polymerization of monomeric $Sap^{AD}$, but did not result in tubule dissolution (FIG. 15*g, f*). Although the mice sera (1:1000) reduced $Sap^{AD}$ self-assembly by ~70% (FIG. 15*g*), they did not destabilize preformed $Sap^{AD}$ lattices. The llama serum (1:1000) showed >90% reduction in $Sap^{AD}$ polymerization, similar to that seen with 15 μM $Nbs^{SAI}$ or $Nb^{AF692}$ (FIG. 15*g*), but resulted in only a partial destabilization of preformed $Sap^{AD}$ tubules (FIG. 15*f*). An approximately 6-fold increase in tubule density compared to buffer control and a decrease in average tubule length from 2.4 to 0.8 μm (FIG. 15*f*) indicated that treatment with llama serum (60 min) resulted in fragmentation of $Sap^{AD}$ tubules. Whilst treatment with Nbs resulted in tubule dissolution within minutes, the tubule density and length distribution of serum-treated samples remained similar over several hours (data not shown). Close inspection of llama serum-treated samples showed aligned and kinked tubule fragments, indicating that tubule breakage occurred after deposition of intact tubules on the EM grid, possibly upon staining and desiccation of the grids (FIG. 22). In contrast, although the earliest timepoints (1 min) in $Nbs^{SAI}$ and $Nb^{AF692}$ treated $Sap^{AD}$ tubules show a ~3-fold increase in tubule number density (FIG. 15*f*, FIG. 21), no aligned or kinked tubules were seen on the inspected grids (>40) (FIG. 22), suggesting that contrary to llama serum the Nb-treatment leads to rapid tubule disintegration in solution. Together, these observations suggest that although antibodies in llama serum can bind polymerization sensitive epitopes, these are only partially reached in preassembled Sap S-Layers and lead to S-Layer destabilization rather than dissolution. Isolated VHH single domain fragments of the llama serum with Sap polymerization inhibitory activity, i.e. $Nbs^{SAI}$, readily reach polymerization sensitive epitopes in intact S-Layers and lead to S-Layer disassembly, possibly due to a reduced steric hindrance of the VHH format compared to intact IgG2 or IgG3 (approximately 15 vs. 80 kDa), or a higher effective concentration.

Also see FIG. 5: Nanobodies used as crystallization aid or S-Layer assembly inhibitor of *B. anthracis* Sap.

(A) To facilitate the 3D crystallization and structure determination of the *B. anthracis* Sap S-Layer assembly domain ($Sap^{216-814}$), we generated a number of camelid single domain antibodies. A set of 20 different anti-Sap Nanobodies was isolated from a Nanobody (VHH) phage library generated from a llama immunized with $Sap^{216-814}$. Of these, two Nanobodies, Nb684 (SEQ ID NO:18) and Nb694 (SEQ ID NO:19), facilitated crystallization of the $Sap^{216-814}$ S-Layer assembly domain, and six Nanobodies proved to be potent inhibitors of $Sap^{216-814}$ self-assembly (see FIG. 8): Nb683 (SEQ ID NO:12), Nb688 (SEQ ID NO:13), Nb692 (SEQ ID NO:14), Nb702 (SEQ ID NO:15), Nb704 (SEQ ID NO:16) and Nb707 (SEQ ID NO:17).

Nanobody-antigen recognition is most frequently determined by three complement determining regions (CDRs): CDR1, CDR2 and CDR3 bind their antigens. These CDR regions are unique for different Nanobodies and form three adjacent loop regions on the Nanobody immunoglobulin fold. When isolating a group of antigen-specific Nanobodies from a llama immunized with the antigen, the resulting Nanobodies can be grouped into families depending on the sequence similarity or diversity in the CDR regions. Nanobodies within families share substantial similarity in the CDR regions, indicating they bind a shared epitope in the antigen, while a lack of similarity in the CDRs is indicative of antibodies that belong to different families and that bind independent epitopes in the antigen.

Multiple sequence alignment of the eight Nanobodies disclosed in this document shows they belong to three antibody families based on pairwise sequence conservation or diversity in CDR1, CDR2 and CDR3. A high degree of sequence similarity in the CDRs of Nb683, Nb684, Nb688, Nb692, Nb702 and Nb707 shows they belong to one family, and that Nb694 and Nb704 represent a second and third family, respectively. Based on the X-ray structure of $Sap^{216-814}$ in complex with Nb684 and Nb694, we can determine the Sap epitope targeted by either family, as well as the paratope in the Nanobodies that is responsible for the antigen recognition. The X-ray structure shows that for family 1 (Nb683, Nb684, Nb688, Nb692, Nb702) the binding paratope comprises a conserved segment of CDR1 and CDR3 (boxed area in the multiple sequence alignment), as well as a variable region in CDR3 (boxed in dotted line in the multiple sequence alignment). Structural details of the antigen~Nanobody binding are displayed in FIGS. 6 and 7.

Also see FIG. 6: Nanobody binding to *B. anthracis* Sap.

(A) Surface representation of the $Sap^{216-814}$ X-ray structure with Nb694 and Nb684 shown as ribbon representation. The structure shows the two independent binding sites of the Na nobodies on D1 (Nb694) and the D1-D2 hinge region (Nb684).

(B) Nb694 binds the Sap D1 domain with its CDR3 paratope shown in panel B in stick representation and as primary sequence.

(C) Nb684 interacts with Sap D1 with the YDYW paratope in the CDR3 region. The tip of CDR3 (sequence GTGGR in Nb684) is also in contact with domain D2. The D2 domain is also contacted by the CDR1 paratope SGSIFR. The YDYW paratope in CDR3, and the SGSIFR paratope in the CDR1 are conserved in Nanobodies of family 1: Nb683, Nb684, Nb688, Nb692, Nb702, indicating that these Nanobodies all bind the same D1-D2 hinge region seen for Nb684 in the $Sap^{216-814}$ X-ray structure. The tip of CDR3 is variable amongst these different Nanobodies and is the likely reason for the variation in Sap binding affinities measured for the different Nanobodies by isothermal titration calorimetry (ITC). These affinities range from dissociation constant of 35±31 nM for Nb683 to 120±40 nM for Nb688.

Also see FIG. 7: Nanobody binding interactions in *B. anthracis* $Sap^{216-814}$.

Ribbon representation of the $Sap^{216-814}$ X-ray structure showing a close-up of the Nb684 binding site on the D1-D2 hinge region. The binding epitope in the Sap protomer is displayed in stick representation. The Sap epitopes in D1 and D2 that form the interaction with the Nb684 are underlined in the sequence shown to right of the figure. Sap is highly conserved within the *Bacillus cereus* group (taxid: 86661; comprising *B. cereus, B. anthracis* and *B. thuringiensis*), with >95% protein sequence identity across the available genomes.

Also see FIG. 8: Anti-Sap Nanobodies act as Sap polymerization inhibitors.

To assess the influence of anti-Sap Nanobodies on the S-Layer assembly properties of Sap, we used dynamic light scattering to monitor the particle size distribution in purified $Sap^{216-814}$ solutions over time. Upper left and right DLS panels show $Sap^{216-814}$ solution at 0 h and 24 h post purification. Freshly purified $Sap^{216-814}$ is present as soluble monomers, but starts to assemble into high molecular weight polymers within hours of purification. EM analysis demonstrated these high molecular weight polymers are formed by S-Layer like 2D crystals (see FIG. 2). Freshly purified $Sap^{216-814}$ was mixed with equimolar amounts of the different anti-sap Nanobodies and analysed by DLS 24 h post purification. Contrary to the control sample where no Nanobody was added, six Nanobodies were found to prevent the formation of S-Layer like high molecular weight polymers within the monitored 24 h period: Nb683, Nb688, Nb692, Nb702, Nb704 and Nb707. Of these six Nb with S-Layer assembly inhibitory activity, 5 belong to family 1, for which structural information in the binding epitope and paratopes is available (See FIGS. 5, 6 and 7): Nb683, Nb688, Nb692, Nb702, Nb704. The sequence conservation in CDR1 and 3 in these Nanobodies (FIG. 5, 6), and the $Sap^{216-814}$ X-ray structure shows these family 1 Nanobodies bind the hinge region of Sap domains D1 and D2. Dot blots were used to monitor the binding of the different Nanobodies to $Sap^{216-814}$ or to the individual immunoglobulin-like domains (D1, D2, D3, D4, D5, and D6). These show that family 1 Nanobodies bind D1, albeit with lower affinity than binding of purified $Sap^{216-814}$. The dot blots show a reduced binding of family 1 Nanobodies to D1 compared to $Sap^{216-814}$(D1-D6). This observation is in accordance with the $Sap^{216-814}$ X-ray structure, which shows that the CDR1 in these Nanobodies binds D2. Full binding affinity is likely to require the presence of D1 and D2. No binding to isolated D2 was demonstrated for these Nanobodies. Nb704 has CDR1 and CDR3 regions that differ markedly from those of family 1, so that it can reasonably be expected to bind a different epitope. Dot blots of Nb704 incubated with the different isolated Sap domains show the Nanobody to also bind D1.

Example 4. Nanobodies with Sap S-Layer Assembly Inhibitory Activity Influence Cell Morphology and Attenuate Growth of *B. anthracis*

Next, we evaluated the effect of $Nbs^{SAI}$ on *B. anthracis* growth. Grown at 37° C. degrees on brain hearth infusion (BHI) medium under static conditions, *B. anthracis* forms long multicellular filaments that clump together at higher cell density. When a 20 μM $Nbs^{SAI}$ cocktail was added to the inoculum, this resulted in significantly reduced bacterial growth rates compared to the buffer control or a 20 μM cocktail of Sap binding nanobodies lacking an assembly inhibitory activity ($Nbs^{S2}$: $Nb^{AF679}$, $Nb^{AF687}$, $Nb^{AF694}$, $Nb^{AF695}$ and $Nb^{AF703}$; 4 μM each) (FIG. 15*f*; FIG. 21*b*). Whilst cells treated with buffer reached confluency within 5 hours post inoculation, a $Nbs^{SAI}$ treated inoculum showed dispersed chains of *B. anthracis* cells only (FIG. 15*g*, FIG. 23*a*), demonstrating that disruption of the Sap S-Layer inhibits bacterial growth. Individual SAI nanobodies varied in their attenuation of *B. anthracis* growth, with $Nb^{AF692}$ approaching that of the $Nbs^{SAI}$ cocktail (FIG. 23*b*). Although $Nbs^{SAI}$ attenuated *B. anthracis* growth, treatment did not lead to full growth inhibition and the culture approached stationary phase densities with an approximate delay of 2 hours compared to an inoculum treated with buffer or a non-SAI Sap-binding Nb (FIG. 23*c*). The growth delay was further shortened when $Nbs^{SAI}$ was added at a later timepoint (2 hours post inoculation) rather than at the start of the inoculum (FIG. 23*c*). This suggested that part of the *B. anthracis* population becomes insensitive to $Nbs^{SAI}$ or that $Nbs^{SAI}$ become titrated below their effective concentration at higher cell densities. When added at the moment of inoculation the inhibitory activity for both $Nbs^{SAI}$ and $Nb^{AF692}$ reached saturation near 100 nM concentration (FIG. 23*d*). SDS PAGE analysis suggested free $Nbs^{SAI}$ stayed above this effective concentration throughout culturing (FIG. 24*a*). Previous studies have shown that cells lacking sap are viable and that also during exponential growth, *B. anthracis* tends to replace the Sap S-Layer for EA1 S-Layers (Mignot et al., 2002; Mesnage et al., 1197) (FIG. 24*b, c*), leaving the possibility that a change from a Sap to a EA1 expressing physiology may lead to recovery from $Nbs^{SAI}$.

To gain insight into the physiological effect of Sap assembly inhibition and Sap S-Layer disassembly, treated *B. anthracis* cultures were examined using light and fluorescence microscopy. $Nbs^{SAI}$ or $Nb^{AF692}$ treated cultures contained cells with striking morphological defects as well as unaffected, normal looking cells resembling control cultures. The affected population presented as cells with irregular, scoured cells surfaces or as collapsed cell masses that had lost the bacilliform cell shape (FIG. 16*a*). Scoured cells had intact cell membranes as judged from a lack of propidium iodide staining (FIG. 24*d*), and made up to 30% of $Nbs^{SAI}$ or $Nb^{AF692}$ treated cultures, whilst no affected cells were seen in buffer, Nb11 or $Nb^{AF703}$ treated cultures (FIG. 16*a, b*). Scoured cells in $Nbs^{SAI}$ or $Nb^{AF692}$ affected showed a small (~0.6 μm) but significant ($p<0.0001$; unpaired two-way t-test) increase in cell length compared to unaffected cells, though nothing like the multifold cell elongation reported for the sap deletion mutant *B. anthracis* RBA91 (Mignot et al., 2002; Mesnage et al., 1197). Scoured and collapsed cells showed an increased staining with fluorescent labeled $Nbs^{SAI}$ or $Nb^{AF692}$ compared to unaffected cells (FIG. 16*a*), suggesting unaffected cells may have had EA1 rather than Sap containing S-Layers. However, staining with anti-Sap or anti-EA1 polyclonal antibody showed Sap as dominant S-Layer constituent in both affected and unaffected cells, with sparse punctuate staining of EA1 only (FIG. 16*b*). Increased staining of $Nbs^{SAI}$ or $Nb^{AF692}$ as well as anti-Sap or anti-EA1 is more likely indicative of an increased antigen accessibility in scoured and collapsed cells. It is unclear whether unaffected cells represent a resilient or an as yet unaffected population of the culture. *B. anthracis* RBA91 cultures showed cells with normal and scoured cell morphology independent of $Nbs^{SAI}$ or $Nb^{AF692}$ treatment, unlikely the eag deletion mutant *B. anthracis* SM91 (Mignot et al., 2002; Mesnage et al., 1197), which showed affected cells in $Nbs^{SAI}$ treated cultures only (FIG. 25). The latter, but not the sap deletion mutant, also showed the collapsed cell masses seen in $Nbs^{SAI}$-treated WT cells, suggesting that disruption of an existing Sap S-Layer by Nbs intervention may be more detrimental than a genetic lack of Sap, which may be (partially) accommodated by changes in cell physiology.

Also see FIG. 9: Nanobodies with S-Layer assembly inhibitor activity influence *B. anthracis* cell envelope morphology.

Fluorescent and differential interference contrast (DIC) micrograph of *B. anthracis* 34F2 cells at exponential growth phase treated with a combination or mix of five* $Nbs^{SAI}$ Nanobodies with S-Layer assembly inhibitor activity (=Nb683, Nb692, Nb702, Nb704 and Nb707) shown as $Nbs^{SAI}$ in row 1 (*: Nb688 was not included due to its high aggregation propensity), or with phosphate buffered saline (shown as buffer in row 2). The mixed $Nbs^{SAI}$ were labeled with DyLight 650 and allowed to bind *B. anthracis* 34F2 cells for 25 minutes. In the images, the localization of the Nb-Dylight 650 conjugates correspond to the Far-Red fluorescent signal. The cells' chromosome was co-stained with Syto9 as a measure of cell integrity. In the mock experiment, *B. antracis* cells were treated with PBS 1× during 25 min and cells' chromosomes were co-stained with Syto9 to show their integrity (row 2, panel A). The microscopy images demonstrate that the mix of five* Nanobodies with S-Layer assembly inhibitory activity influence *B. anthracis* cell morphology in a severe way. $Nbs^{SAI}$ affected cells are labelled with white arrows. From these images two stages of morphology disturbance $Nbs^{SAI}$ induced can be observed. An initial wrinkled morphology of $Nbs^{SAI}$ affected cells (w=wrinkled morphology in the DIC panel) and what we believe to be a final stage of disturbance, the bubbling stage (b=bubbling morphology in the DIC panel). In the bubbling stage of $Nbs^{SAI}$ affected cells the wild type (wt) cellular morphology is far-gone. The experiment reveals for the first time that Sap assembly inhibitors lead to severe *B. anthracis* morphology defects and may therefore attenuate *B. anthracis* growth.

One of the $Nbs^{SAI}$, Nb692, is able to affect *B. anthracis* morphology at high concentration as the $Nbs^{SAI}$ mix, inducing cellular defects as has been observed in FIG. 9, row 3 (wrinkled and bubbling morphologies). In row 4 and 5, images of the effect of Nbs controls are shown to prove that the morphology defects observed on *B. anthracis* $Nbs^{SAI}$ treated cells are the consequence of disruption and disturbance of the Sap S-Layer assembly at the cellular surface. Nb703 is an anti-Sap Nbs that doesn't show any assembly inhibitory activity in vitro (Data not shown) or in vivo (see row 4), where instead is able to bind the cellular *B. anthracis* surface without compromising its wt morphology (pointed in the figure with a white arrow). Nb208 is an anti-GFP Nb, a non-related *B. anthracis* S-Layer Nb that behaves as the PBS1× treated cells. Scale bars correspond to 10 μm.

Also see FIG. 10: $Nbs^{SAI}$ *B. anthracis* affected cells are Propidium Iodide negative LIVE/DEAD™ BacLight™ assay to establish bacterial viability of $Nbs^{SAI}$ *B. anthracis* 34F2 affected cells. *B. anthracis* 34F2 cells at exponential growth phase were treated with PBS 1× (mock experiment, Syto9 positive cells, row 1), Triton 10% (propidium iodide (PI) positive cells, row 2) and the $Nbs^{SAI}$ (row 3 and 4). For all the three sets of experiments, cells were first incubated in parallel during 25 minutes with PBS, Triton or labeled DyLight 650 $Nbs^{SAI}$. In order to monitor post-treatment viability of *B. anthracis* cells as a function of their membrane integrity, cells were then incubated with Syto9 and PI stains together as suggested by the manufacturer. Cells with a compromised membrane that are considered to be dead or dying will stain red, whereas cells with an intact membrane will stain green. From this LIVE/DEAD™ BacLight™ assay chromosomes of $Nbs^{SAI}$ *B. anthracis* 34F2 affected cells, in both their phenotypes (bubbling row 3, wrinkled row 4), stained with Syto9 dye and they were PI negative. With this result we can conclude that $Nbs^{SAI}$ *B. anthracis* 34F2 affected cells despite the severe morphology defects presented, maintain an intact membrane and are considered to be alive. That being said, such morphological defects could affect cellular division and growth. Scale bars correspond to 10 μm.

Also see FIG. 11: Nanobodies with Sap S-Layer assembly inhibitory activity attenuate *B. anthracis* growth.

(A) Phase contrast frames from a time-lapse experiment in BHI medium imaging the growth of *B. anthracis* 34F2 cells at indicated time points and treated with 40 μM each of the mix of Nanobodies with Sap S-Layer assembly activity; or treated with buffer. Cells were pretreated with the anti-Sap Nanobodies. The control culture goes into a rapidly dividing—exponential growth phase that leads to full cell confluence within 5 h post inoculation (hours post inoculation indicated in A). In sharp contrast, the culture treated with the anti-Sap Na nobody mix shows a strongly reduced growth rate and is unable to reach confluency in 5 h times post inoculation in rich medium.

(B) Plotted time trace of the *B. anthracis* 34F2 growth curves in presence ($Nbs^{SAI}$) or absence ($Nbs^{S2}$=pool of Nbs that lack Sap S-Layer inhibitory activity) of anti-Sap Nb Sap S-Layer assembly inhibitors reiterates the strongly reduced growth rate of the SAI inhibitory Nanobody treated bacteria.

(C) Plotted time trace of the *B. anthracis* 34F2 growth curves treated with 40 μM each of the mix of Nanobodies of $Nbs^{SAI}$, single $Nbs^{SAI}$ 200 μM or PBS1×. Nb692 200 μM induces a strongly reduced growth rate of the treated bacteria comparable to the $Nbs^{SAI}$ treated ones.

These demonstrate for the first time that in vivo interference with Sap S-Layer assembly during exponential growth of *B. anthracis* influences cell morphology and attenuates cell growth. The data suggest that Sap S-Layer assembly inhibitors have a therapeutic value by suppressing *B. anthracis* growth and/or infection. Similarly, Sap assembly inhibitory antibodies raised as part of an immune response induced by vaccination of an individual with purified Sap, or Sap domains (especially of interest are Domains 1, 2, 4 and 6 based on the structural data provided in this study), can be expected to provide protection against development and/or progression of anthrax disease.

Example 5. In Vivo Clearance of *B. anthracis* Infection Via $Nb^{SAI}$ Treatment The present invention demonstrates that the inhibition of Sap S-Layer assembly during in vitro culturing of *B. anthracis* 34F2 attenuates bacterial growth. Sap assembly inhibitors, for example the Nanobodies as depicted in SEQ ID NOs: 20-25, can thus have a therapeutic effect when administered intravenously for pulmonary or intestinal anthrax (both systemic diseases), or administered topically in case of cutaneous anthrax. Such Sap assembly inhibitors may also be administered in supplement to current antibiotic treatments. It has been reported that mice infected intraperitoneally with an inoculum of 100,000-1,000,000 colony forming units (CFUs) of *B. anthracis* 34F2 (lacking pXO2) succumb to anthrax disease within 3-4 days post-inoculation, providing a good animal model for the evaluation of new therapeutic treatments.

The therapeutic potential of $Nbs^{SAI}$ was evaluated here in a rodent model of lethal *B. anthracis* infection. Whereas sham-operated and Nb11-treated mice succumbed to lethal anthrax disease within 3-5 days post-inoculation, all animals that were subcutaneously treated with 10 doses of 20 nmole $Nbs^{SAI}$ or $Nb^{AF692}$ administered over a 6 days period survived (FIG. 17*a*). However, mice given a single $Nbs^{SAI}$ treatment concomitant with the infectious inoculum succumbed to anthrax disease (FIG. 26*a*), demonstrating the need for consecutive treatment doses during ongoing infection. Mice in the repeated dosing arm of the cohort fully recovered from anthrax symptoms over the first days of Nb therapy and showed no signs of illness up to a week after coming off treatment when the experiment was halted, suggesting they had fully cleared the infection. Treatment remained effective also when the first treatment dose was administered briefly (15 min) after infection rather than concomitant with the infectious inoculum (FIG. 17*b*).

For mouse infection, the *B. anthracis* 34F2 inoculum was grown on RM+ medium to induce expression of the anthrax exotoxins (FIG. 26*b*). Cells grown on RM+ predominantly express the Sap S-Layer (FIG. 26*c, d*). When treated with $Nbs^{SAI}$ or $Nb^{AF692}$ these cells show abundant morphological defects and increased areas corresponding to collapsed cell masses (FIG. 26*e*).

Also see: FIG. 12. To evaluate the therapeutic value of our Sap Assembly Inhibitors, either as stand-alone treatment or as supplementation therapy to current antibiotic treatments, mice were injected subcutaneously (in the right flank) with 100,000 *B. anthracis* 34F2 CFUs resuspended in 100 µl $Nbs^{SAI}$ 200 µM or PBS1× (in the mock experiment) and treated twice daily with subcutaneous doses of a $Nbs^{SAI}$ or PBS1×. As shown in FIG. 12(A), mice treated with $Nbs^{SAI}$ were able to clear *B. anthracis* 34F2 infection and survived lethal anthrax disease. In a following experiment, shown in FIG. 12(B) we evaluated the necessity of providing $Nbs^{SAI}$ with the inoculum at the moment of infection. Mice pre and post treated with $Nbs^{SAI}$ were equally able to clear *B. anthracis* 34F2 infection and survive lethal anthrax disease. In the experiment shown in FIG. 12(C), we evaluated the effect of treating infected mice with an equal concentration of our negative control Nb208. Nb208 mice treated succumbed to lethal anthrax disease. Nb692 alone was tested with the mice based on its in vivo observed effect on the bacterium (FIGS. 9, A3 and 11C). 50% of the Nbs692 treated mice were able to clear *B. anthracis* 34F2 infection and survive lethal anthrax disease. In all performed mice experiments the survival of mice was followed up during 10 days from the end of the experiment; n is equal to the number of mice per group used in an experiment.

Example 6. Evaluation of Monomeric $Sap^{AD}$, D1, D4 and D6 Protective Effect Against Anthrax in Mice The present invention demonstrates that the inhibition of Sap S-Layer assembly during in vitro culturing of *B. anthracis* 34F2 attenuates bacterial growth. We demonstrate here that the immunization of a Llama with fresh, non-assembled solutions of the Sap S-Layer assembly domain ($Sap^{AD}$) (SEQ ID NO: 4) resulted in the isolation of single domain antibodies with an inhibitory activity towards Sap S-Layer assembly. We show that when added during *B. anthracis* growth, Nbs with Sap assembly inhibitory activity (for example SEQ ID NOs: 20-25) result in cell envelope defects and attenuated bacterial growth. For therapeutic purposes, when injected subcutaneously in mice undergoing a *B. anthracis* infection, such Sap Assembly inhibitors worked as successful therapy that cured the infected mice from lethal anthrax disease. Alternatively, we hypothesised that for prophylactic purposes, a humoral response with an activity as Sap assembly inhibitors could be generated by immunization of hosts with the Sap S-Layer assembly domain (SEQ ID NO:4) or by the individual Sap domains that are here identified as important for maintaining the lattice contacts in the Sap S-Layer: D1, D4 and D6 (FIG. 4). Unlike purified Saps (SEQ ID NO:1), the individual domains such as D1, D4 or D6 do not self-assembly into S-Layer polymers. Self-assembled Sap forms a viscous gel-like solution that is difficult to administer and correspond to an antigen that may shield the protective epitopes from the immune system. Therefore, vaccine formulations based on individual domains such as D1, D4 or D6 were expected to have advantageous storage properties and maximise the presentation of protective epitopes to the immune system.

To test the potential of a vaccination with monomeric fresh $Sap^{AD}$ (SEQ ID NO:4) or the storable individual domains D1 (SEQ ID NO:6), D4 (SEQ ID NO:9) or D6 (SEQ ID NO:11) important for S-Layer assembly, mice were immunized with the corresponding proteins and challenged with *B. anthracis* 34F2, as described in the material and method section. As shown in FIG. 13A, all mice immunised with monomeric fresh $Sap^{AD}$ or immunised with D1 had an abundant immune response, as judged by the strong increase in Sap-specific IgG antibodies in the post immunization sera measured by ELISA. Sera of animals immunized with D4 or D6 showed low and heterogeneous titres in Sap-binding IgG, pointing to the lower immunogenicity of these two regions when presented as individual domains.

Despite the observed immunogenicity of the monomeric $Sap^{AD}$ and D1, the single domains involved in Sap S-Layer assembly, the humoral response raised in the immunised mice did not result in a statistically significant protection against anthrax disease (FIG. 13B; Survival: PBS1×: 1/8; $Sap_c$2/8; D1 2/8; D4 1/8; D6 0/8). Possibly, conventional two domain antibodies with molecular mass of 150 kDa and above cannot access their binding epitopes buried in the Sap interfaces involved in S-Layer assembly due to steric constraints. Steric occlusion may thus prevent Sap-binding antibodies to act as in vivo S-Layer assembly inhibitors, contrary to single domain antibodies such as the $Nbs^{SAI}$ or active antibody fragments of the present invention.

Finally, when mice immunized with monomeric $Sap^{AD}$ or individual Sap domains ($Sap^{D1}$, $Sap^{D4}$ or $Sap^{D6}$) were challenged with live *B. anthracis*, they succumbed to lethal anthrax disease within a week of infection (FIG. 17*c*), despite robust anti-Sap titers in their sera (FIG. 17*d*) and a Sap assembly inhibitory activity of the sera (FIG. 15*g*). Unlike $Nbs^{SAI}$ or $Nb^{AF692}$, mice sera had no dissolving activity towards $Sap^{AD}$ tubules, suggesting that the Nbs S-Layer disrupting activity of the Nbs may be critical for therapeutic efficacy.

In conclusion, we show that camelid single domain antibodies provide a unique platform to generate S-Layer penetrating and disrupting affinity reagents that have growth inhibitory activity on *B. anthracis* and can provide a therapeutic potential during ongoing anthrax disease. These observations provide tantalizing evidence that in vivo S-Layers disruption can be detrimental to bacterial growth and that S-Layers may provide good therapeutic targets in additional human pathogens, including *Clostridium difficile, Serratia marcescens* and *Rickettsia's* (Kirk et al., 2017).

Example 7. SlpA Specific Nanobodies that Affect *Clostridium difficile* S-Layer and Survival In order to further validate the prove of principle described herein, namely that in vivo inhibition of S-layer assembly and disintegration of pre-existing S-layer affects cell morphology, bacterial growth and virulence in S-layer carrying pathogens, we produce the *C. difficile* S-layer protein SlpA, for llama immunization, using the method as described herein for the *B. anthracis* Sap SLP (see Material and Methods). The Nbs specific for the low and high molecular weight components (LMW and HMW, respectively) of SlpA are isolated using panning procedures as described herein, and screened in vitro for S-layer assembly inhibitory activity using DLS and EM. Additionally, assembly inhibitory Nbs are screened with EM or atomic force microscopy to identify those with S-layer depolymerising activity on a reconstituted SlpA S-layer and/or S-layer carrying bacteria. Identified Nbs with such activities are then tested for in vivo activity on bacterial cells as described herein. Cell morphology and growth rate of *C. difficile* cells treated with Nbs are monitored and where anti-SlpA Nbs induce morphology and growth defects, further, these are used for the evaluation of therapeutic application in a mouse model of *C. difficile* infection, as described herein for the *B. anthracis* in vivo experiments.

Material and Methods

Production of Soluble Monomeric Recombinant *B. anthracis* $Sap_c$ (=$Sap^{AD}$) and $EA1^{AD}$.

Cloning of Sap. In order to ensure a good overexpression of the *B. anthracis* genes $Sap_c$ or $Sap^{216-814}$ or $Sap^{AD}$ (SEQ ID NO:2, with a 35% GC content) and EA1AD (SEQ ID NO:27) in *E. coli*, a synthetic codon-optimised gene encoding $Sap_c$ or $Sap^{216-814}$ or $Sap^{AD}$ (functional domain of the protein sufficient to form the 2D paracrystalline layer, named also Sap crystallization domain or S-Layer Assembly Domain, that contains residues 216-814 of the mature protein UniProtKB P49051, C-terminal 6-His tagged, as depicted in SEQ ID NO:5) and of $EA1^{AD}$ (functional domain of the protein sufficient to form the 2D paracrystalline layer, that contains residues 214-862 of the mature protein UniProtKB P94217, N-terminal 6-His tagged, as depicted in SEQ ID NO: 28), were generated by gene assembly using overlap PCR of a series of component oligonucleotides. The synthetic $Sap^{216-814}$ and $EA1^{AD}$ were cloned by Gateway technology into a pDEST14 and pET300 expression vector, creating pAFSLP1 and pAFSLP10, respectively.

$Sap^{216-814}$ production and purification. *E. coli* BL21 (DE3) cells were transformed with pAFSL1 or pAFSLP10. Cells transformed with pAFSL1 ($Sap^{AD}$ expression) were grown in LB medium supplemented with Amp (100 μg/mL) and 0.1% glucose at 37° C. and induced with 10 μM isopropyl 1-thio-D-galactopyranoside when an $OD_{600}$ of 0.6-8 was reached. After O/N induction at 37° C., 50 mL of cells were harvested by centrifugation and resuspended in 50 mL of buffer A (50 mM tris pH 8, 300 mM NaCl) supplemented with protease inhibitors (4-(2-aminoethyl) benzenesulfonyl fluoride and leupeptin, 0.1 mg/mL and 1 μg/mL final concentrations, respectively), 0.1% Triton-100, 20 mM imidazole pH 8. Cell were lysated using a cell disruptor system (Constant Systems) and centrifugated at 20,000 g. The supernatant containing His6-tagged $Sap^{216-814}$ was applied to 5 mL of WorkBeads™ agarose resin beads 40 $IDA^{high}$ charged with $Ni^{2+}$ (Bio-Works), pre-equilibrated with buffer A. After extensive washing with buffer 4% buffer B (50 mM Tris pH 8, 300 mM NaCl, 500 mM Imidazole pH 8), the protein was eluted with 100% buffer B and filtered with a 0.2 μm filter (Acrodisc LC 13 mm, Syringe filter Life Science) and consequently injected in the Gel filtration column. Size-exclusion chromatography (Superdex 200 16/60) was performed as final step of purification in $Sap^{216-814}$ storage buffer containing 10 mM Tris pH 8, 100 mM NaCl, 5% glycerol. Pooled fractions corresponding to the monomeric form of the protein (column elution volume 68-78 mL) were filtered as before, adjusted to a concentration of 0.2 mg/mL and stored at 30° C. until further use. Production and purification of $EA1^{AD}$ were performed as described elsewhere (Wang et al., 2015). Monodispersity and polymerization state of $Sap^{216-814}$ or $EA1^{AD}$ preparations were evaluated by Dynamic Light scattering (DLS) or negative stain transmission electron microscopy (see below).

Selenomethionine labeled $Sap^{216-814}$ To produce selenomethionine labeled $Sap_c$ for structural studies, the methionine auxotrophic *E. coli* strain B843 was transformed with pAFSL1 and cultured in LB media as described previously (Moonens et al., 2016) and pre-cultured in M9-based minimal media, supplemented with SelenoMet Medium Base and SelenoMet Nutrient Mix as recommended by the manufacturer (Molecular Dimensions Ltd.), 40 μg/mL L-methionine and 100 μg/mL of ampicillin. O/N culture was washed in phosphate buffered saline (PBS, 10 mM $PO_4^{3-}$, 137 mM NaCl, and 2.7 mM KCl) prior inoculation in the above minimal medium (1:100 dilution), now supplemented with 40 μg/mL L-selnomethionine (Acros Organics) instead of L-methionine. Protein expression and purification was performed as for the non-labeled protein with the exception that all buffers used for the purification were supplemented with 1 mM DTT to prevent selenomethionine oxidation.

Sap Domains Cloning, Production and Purification

The coding sequences corresponding to $Sap^{216-814}$ Domains (as depicted respectively in SEQ ID NO:6-SEQ ID NO:11 (D1-D6) and SEQ ID NO:26 (D4')) were PCR amplified from the codon optimized pAFSLP1 sequence using primers (SEQ ID NO: 30-35). The generated gene fragments correspond to the following residues of the mature protein linked to a C-terminal His6 sequence: D1 (216-295 AA), D2 (296-384 AA), D3 (385-490 AA), D4 (491-595 AA), D5 (595-706 AA) and D6 (707-814 AA), and D4' (491-624 AA). Genes were cloned by Gateway Technology into a pDEST14 expression vector, pAFSLP2, pAFSLP3, pAFSLP4, pAFSLP5, pAFSLP6 and pAFSLP7 for $Sap^{D1}$ to $Sap^{D6}$, respectively. Expression and purification of the recombinant Sap domains were performed as described for $Sap^{AD}$, with the exception that size exclusion was performed with S100 16/60 column in the following optimized storage buffers: Tris pH 8 was used for Sap domains D1, D2, D3 and D5; while Tris pH 7.5 was used for Sap D4; and Hepes pH 7 was used for Sap D6.

Induction of a Humoral Immune Response in Llama and Nanobody (Nbs) Identification Llama (Llama glama) was immunized with 6 subcutaneous injections of adjuvant (Gerbu LQ, GERBU biotechnik) emulsified monomeric $Sap^{216-814}$ (0.14 mg per injection) within 15 h from purification to ensure maximal monomeric $Sap^{216-814}$. Immunogens were administered in weekly intervals and four days after the final boost, llamas were bled and total RNA was extracted from collected peripheral blood mononuclear cells according to Domanska et al. (2011). Starting from total RNA, cDNA was synthesized and the Nbs repertoire was amplified and cloned following the method published by Conrath et al. (2001), except that phagemid pMESy4 was used as the display vector allowing the expression of C-terminal His6-EPEA tagged Nbs. The resulting library consisted of $4.6\times10^9$ independent clones and 100% of these clones contained an insert corresponding to the size of a Nbs. To identify $Sap^{216-814}$-specific binders, 1 μg of the monomeric antigen was solid phase immobilized in sodium bicarbonate buffer pH 8.2 in 96-well Maxisorp plates (Nunc). Microwells were subsequently blocked with PBS containing 2% skimmed milk powder. Following incubation with Nbs displaying phage, unspecific phage was removed by extensive washing with PBS 0.05% Tween-20 and bound phage was eluted after trypsin treatment. Two rounds of selections were performed and 94 monoclonal Nbs randomly picked from the first and second round outputs were expressed in the periplasm of *E. coli* WK6. Specific Nbs were identified via ELISA by coating 1 μg of the monomeric $Sap^{216-814}$ in Maxisorp plates. Bound Nbs were detected via the "EPEA" tag using a the CaptureSelect Biotin anti-C-tag Conjugate (Life technologies) mixed with Alkaline Phosphatase (Promega) for revelation. All $Sap^{216-814}$-specific Nbs were sequenced.

Nanobody Production and Purification

Nanobodies were expressed and purified as C-terminal His6 fusions in *Escherichia coli* WK6 periplasm, using the pMESy4 as described in Pardon et al. (2014) with the exception that size exclusion chromatography (Biorad enrich SEC70 column) was performed as final step of purification for each Nbs within 10 mM optimized buffers (Hepes pH 7: Nbs 692 & 707; Tris pH 7.5: Nbs 684 & 688; Tris pH 8: Nbs 683, 694, 702, 704) supplemented with 100 mM NaCl and 5% glycerol.

Dynamic Light Scattering (DLS)

DLS analysis. Intensity correlation functions of freshly purified Saps solutions were collected at 25° C. in 4 μL Cyclic Olefin Copolymer (COC) disposable cuvettes at an angle of 90° employing a Dynapro NanoStar DLS machine (Wyatt technology). Intensity correlograms were processed using Dynamics software provided by Wyatt distributor to determine the size distribution of $Sap^{AD}$ in solution, alone or in presence of single Nbs, $Nbs^{SAI}$, mice or llama sera.

Sample preparation. A fresh preparation of $Sap^{216-814}$ obtained with the procedure described above with a concentration of 0.22-0.3 mg/mL, maintained at 30° C., presents a monodisperse size distribution around 4 nm particle diameter, that corresponds to a folded monomeric state of the protein. The polymeric profile of $Sap_c$, with a high particle diameter of 1000 nm and more, was obtained by incubating the monomeric proteins at RT over a 24 h period or instantaneously when increasing protein concentration. Adding 1.5 fold (in μM) of single Sap Nbs to fresh monomeric $Sap^{216-814}$ prevents its polymerization over time and at higher $Sap^{216-814}$ concentration (FIG. 6: monomeric $Sap^{216-814}$ 3 μM was added to 4.5 μM of Nbs and concentrated 20 fold). $Sap^{AD}$ polymerization inhibition activity of Nbs or llama and mice sera was evaluated by DLS over time by addition of a 1.5 fold molar excess Nbs or a 1:1000 dilution of mice or llama sera to fresh monomeric $Sap^{AD}$ preparations at 3.5 μM. Samples where then concentrated 10 fold at incubated at RT prior DLS measurement. The ration monomeric/polymeric $Sap^{AD}$ was calculated by plotting the % mass of particles with size distribution below and above 10 nm diameter, respectively.

$Sap^{AD}$ Depolymerization Assays and Electron Microscopy.

$Sap^{AD}$ assembly into 2D lattices and tubules was allowed to proceed by prolonged incubation of 2 mg/mL freshly purified $Sap^{AD}$ in PBS at 25° C. $Sap^{AD}$ polymerization state was monitored by DLS (see above) and negative stain EM. To verify in vitro depolymerization activity of Nbs, mice or llama sera on $Sap^{AD}$ S-Layer lattices, $Sap^{AD}$ tubules were incubated with indicated concentrations of single Nbs (Nb11 or $Nb^{AF692}$), $Nbs^{SAI}$, a 1:1000 dilution of mice or llama sera or PBS buffer as negative control. Reactions were incubated for 24 hours and samples were taken for monitoring by nsTEM at 1, 5, 10 and 60 minutes post incubation (PI) in case of $Nbs^{SAI}$ and $Nb^{AF692}$, or at 60 minutes PI for Nb11, PBS and mice or llama sera samples (FIG. 15*d, e, f* and FIGS. 21*a* and 22). All samples were prepared for negative stain electron microscopy by applying 5 μl sample to a non-glow discharged formvar copper 400 mesh grid (EMS), rinsing with 10 μl PBS and staining for 30 seconds in 10 μl 1% uranyl formate. Negatively stained samples were imaged at 1200× magnification (pixel size 9.55 Å) using an in-house 120 kV JEM 1400 (JEOL) microscope equipped with a LaB6 filament and CMOS camera (TVIPS TemCam F-416). Five squares (15.3 μmt each) were randomly selected for tubule counts and length measurements with the ImageJ software. Length and number (labeled "c") of all individual $Sap^{AD}$ tubules in the accumulated 5 grid squares were plotted as boxplots using the GraphPad software, with the median indicated as approximate sample average (FIG. 14*e-f*).

Crystallization and Data Collection

Sample preparation for crystallization. A fresh monomeric preparation of Selenomethionine $Sap^{216-814}$ (2-3 μM) was O/N incubated at 30° C. with a 1.5 fold excess of Nb684 and Nb694 (as depicted in resp. SEQ ID NO:18 and 19). Prior 40 fold concentration at RT using an AMICON® 10 KDa centrifugal filter unit, proteins mix was filtered with a 0.2 μm filter (Acrodisc LC 13 mm, Syringe filter Life Science) in order to remove Sap polymers. After 3 weeks at 20° C. selenomethionine labeled $Sap^{216-814}$ in complex with Nb684-Nb694 ($Sap_c$ 120 μM, Nbs 180 μM) crystals formed in 0.1 M SPG (2-Amino-2-(hydroxynnethyl)propane-1,3-diol) buffer pH 6.0 25% w/v PEG 1500 using sitting-drop vapour-diffusion method.

Data collection. The crystallization buffer was supplemented with 10% glycerol and crystals were mounted in nylon loops and flash-cooled in liquid nitrogen. Diffraction data were collected at Diamond light source on beamline I03 under experiment MX12718-10. Single crystal diffraction data were collected at a wavelength of 0.9795 Å, corresponding to the Se K-edge absorption peak, truncated to 2.95 Å resolution and scaled into space group C2221 with unit cell parameters a=107.89 Å, b=115.35 Å and c=151.05 Å. Heavy atom sites were determined and refined using the programs SheIXD (Sheldrick et al., 2010) and Sharp (Bricogne et al., 2003). Experimental phases were determined according the Single Anomalous Dispersion (SAD) method and were solvent modified using the programs DM and Solomon (Abrahams et al., 1996; Collaborative Computational Project, Number 4, 1994; Cowtan et al., 1996), yielding good quality maps that allowed unambiguous tracing of the $Sap_c$ structure. The $Sap_c$ model was built manually using Coot and refined using Refmac5 (Murshudov et al., 1997) and Buster (version 2.10.3. Global Phasing Ltd, Cambridge, United Kingdom, 2017) to a R and freeR factor of 18.7% and 25.0%, respectively. See Table 1 for data collection and refinement statistics.

Coordinates and structure factors of the $Sap^{AD}$-$Nbs^{AF684}$-$Nbs^{AF684}$ complex have been deposited in PDB under accession code 6HHU.

TABLE 1

Data collection, phasing and refinement statistics

| | $Sap^{AD}$-$NbAF^{684}$-$Nb^{AF694}$ |
|---|---|
| Data collection | |
| Space group | $C222_1$ |
| Cell dimensions | |
| a, b, c (Å) | 107.6, 115.1, 152.8 |
| α, β, γ (°) | 90, 90, 90 |
| Resolution (Å) | 32.1 −2.7 (2.81-2.7) * |

TABLE 1-continued

| Data collection, phasing and refinement statistics | |
|---|---|
| | $Sap^{AD}$-$NbAF^{684}$-$Nb^{AF694}$ |
| $R_{pim}$ | 6.5 ( 53.7) * |
| I / σI | 8.3 (1.6) * |
| Completeness (%) | 99.8 (98.4) * |
| Redundancy | 12.5 (10.2) * |
| Refinement | |
| Resolution (Å) | 32.1 −2.7 |
| No. reflections | 26344 |
| $R_{work}$ / $R_{free}$ | 18.7/25.0 |
| No. atoms | |
| Protein | 6253 |
| Water | 114 |
| B-factors | |
| Protein | |
| $Sap^{AD}$ | 68.8 |
| $Nb^{AF684}$ | 58.2 |
| $Nb^{AF694}$ | 57.2 |
| Water | 52.4 |
| R.m.s deviations | |
| Bond lengths (Å) | 0.01 |
| Bond angles (°) | 1.39 |

* Values in parentheses are for highest-resolution shell.

Isothermal Titration Calorimetry

Isothermal Titration calorimetry (ITC) experiments were carried out using an iTC200 Microcalorimeter (Microcal, Inc., Northampton, Mass.). The equipment's sample cell volume is 200 μL and syringe final volume is 39 μL. calorimetric experiments were performed at 30° C. The reference cell (200 L) was loaded with water during all experiments and the sample cell (203 μL) was filled with fresh monomeric $Sap_c$ at 7 μM concentration. The injection syringe (39.5 μL) was filled with Nbs the different Nbs at 100 μM concentrations. All ITC measurements were performed in $Sap^{216-814}$ storage buffer. The binding reaction started with one injection of 0.5 L of Nb to prevent artefacts, followed by 10 injections of 3.9 μL at intervals of 180 s, reaching a final volume 39.5 μL with a stirring speed of 500 rpm. The heat variation was monitored inside the cell allowing determination of binding enthalpy of the process (DH) and the equilibrium association constant ($K_a$). All enthalpy values for binding reactions were exothermic. Control titrations were performed to subtract the heats of dilution and mixing for each experiment. Single set of sites model was utilized to determine the binding and thermodynamics constants and estimates for $K_a$, and ΔH parameters were refined by standard Marquardt nonlinear regression method provided in the Origin 7 SR4 software.

Small Angle X-Ray Scattering (SAXS).

SAXS data for monomeric $Sap^{AD}$ in complex with $Nb^{AF683}$ were collected at home source using a Rigaku BioSAXS-2000 instrument. Monomeric $Sap^{AD}$ was preincubated with a 5 fold excess of $Nb^{AF683}$ prior to sample concentration. Sample was then loaded on a Superdex 200 16/60 (GE Life sciences) equilibrated with $Sap^{AD}$ storage buffer and eluted fractions were subjected to the data collection. Scattering intensities were collected on 70 μL samples of $Sap^{AD}$-$Nb^{AF683}$ L 1, 3 and 5 mg/mL. The radial averaging and the buffer subtraction were performed using the Rigaku SAXSLab software and averaged data were analysed using the ATSAS software package (Petoukhov et al. 2012). SAXS profiles of the three sample concentrations superposed well and showed linear Guinier plots with an estimated Rg of 39.5 Å (±1.5) (FIG. 20*b*) supporting the monodispersity of the sample. For further analysis, SAXS data of the 3.0 mg/mL sample were used. The molecular mass of the scattering particle was derived using the QR method. Calculation of the probability distribution curve was done using the ATSAS program GNOM (Svergun et al., 1992) and CRYSOL (Svergun et al., 1995) was used for calculation of the theoretical scattering profile of the $Sap^{AD}$-$Nb^{AF684}$ complex extracted from the $Sap^{AD}$-$Nb^{AF684}$-$Nb^{AF694}$ crystal structure and used for fitting into the experimental SAXS volume. Ab initio shape information of the particle in the experimental scattering data was calculated using the probability distribution curve (P(R) curve) information using the DAMMIN software of the ATSAS package. The resulting dummy atom models from 10 independent DAMMIN runs were averaged and filtered with DAMAVER resulting in the final ab initio model. The Situs module pdb2vol was used to convert the averaged, filtered models into volumetric map and SUPCOMB was used to superimpose the $Sap^{AD}$-$Nb^{AF684}$ structure with the dummy atom models (Kozin et al., 2001).

*B. anthracis* 34F2 S-Layer Composition and Protective Antigen (PA) Production in BHI or $RM^+$ Media.

Cell Associated Sap and EA1 over *B. anthracis* in 34F2 Growth in BHI.

*B. anthracis* 34F2 O/N culture was refreshed in Brain Heart Infusion broth or in RM+ medium (R medium supplemented with Foetal Calf Serum; Leppla, 1988) in order to have a starting $OD_{600}$ of 0.05. Cells grown at 37° C. on BHI or on 35° C. on RM+ with shaking were harvested at the indicated time points and normalized to $OD_{600}$ 0.1 (FIGS. 24*a*, 26*b*). They were then resuspended in 1× Laemmli buffer and incubated during 1 h at 95° C. Whole cell extract were diluted 1:20 in water and 5 μL of the dilutions were spotted on the nitrocellulose membrane.

Purified proteins. 3 μL of purified protein 0.3 mg/mL, were spotted on a nitrocellulose membrane as controls.

Procedure. Spotted membranes were blocked in 10 mL of 4% milk, 1×PBS, 0.05% Tween during 30 min at RT with shaking followed by a 2 h incubation with mice polyclonal anti-Sap or anti-EA1 (1:1000, PBS 1×, 0.05% Tween) at RT with shaking. After an extensive wash with water, membranes were incubated during 45 min with Goat anti-Mouse alkaline phosphatase tagged antibody (AQ3562 Sigma-Aldrich, 1:1000 in 1×PBS/0.05% Tween). Following a last wash step, proteins presence was revealed by incubation with detection reagent (alkaline phosphatase buffer supplemented with NBT/BCIP Roche).

For the detection of protective antigen expression, *B. anthracis* 34F2 cultures grown O/N in BHI or $RM^+$ were spun down and prepared as described above. Samples were loaded and separated by 8% SDS-PAGE before transfer onto polyvinylidene difluoride (PVDF) membrane by western blotting. Blocking, incubation with antibody and washing of the membrane were done as described above with a blocking step containing 3% (w/v) non-fat dry milk. Immunoblots were incubated overnight with monoclonal mouse α-PA primary antibody (Bei Resources). Recombinant PA protein (made in house) was used as positive control. Horseradish peroxidase-conjugated goat anti-mouse (Cat. No 115-035-146, Jackson Immunoresearch Laboratories) secondary antibody was used to detect proteins by enhanced chemiluminescence.

Light and Fluorescent Microscopy

Cells samples subjected to microscopic analysis, except for the time lapse experiments, were fixed with PBS 1× supplemented with 4% paraformaldehyde (PFA) prior their observation in glass slide and coverslip. DIC and Fluorescent microscopy images for FIGS. 9 and 10, were acquired with Zeiss LSM 880 airyscan confocal microscope with a magnification of 200×.

Time-lapse acquisition of Nbs treated cells growth in BHI were performed in an Incucyte™ Zoom system (Essen Bioscience). Phase contrast Images using a 20× objective were acquired every 15 min in 4 different zones of the well in order to cover the entire well surface. Cell confluency on single images was estimated by defining region of interest (ROI) within all images and calculating the amount of pixel in the ROIs with the Incucyte™ Zoom software. The confluence results are the mean of 4 technical replicate and two biological replicates.

Samples Preparation:

Nbs effect on morphology. *B. anthracis* 34F2 cells, RBA91 (Δsap) or SM91 (Δeag) (Mesnage et al., 1997), grown as described above, were harvested in their mid-exponential growth phase (2-3 h post inoculation), when Sap is at its maximum peak of expression, or in case of cells grown in RM+, from an O/N culture. The chromosomes of harvested cells (corresponding approximately to $2\times10^6$ CFU) were first washed in PBS 1× and then stained with Syto9 (Invitrogen; 1.169 μMin 0.85% NaCl) during 15 min and then the excess was removed by centrifugation. Cells were then incubated during 20 min at RT with PBS1× supplemented with 100 or 200 μM $Nbs^{SAI}$ mix or 200 μM single Nb or Nb controls previously labeled with DyLight 650 (Thermo Scientific; FIG. 16*a*, FIG. 24*b*) or Dylight 594 (Thermo scientific; FIG. 16*c*, FIGS. 25 and 26) as described elsewhere (Coppens et al., 2015). For Sap and EA1 cell surface, bacteria were additionally immunostained with mouse antiserum raised against purified recombinant $Sap^{AD}$ or $EA1^{AD}$ (see below) followed by incubation with Dylight 633 labelled monoclonal goat-anti-mouse (1:1000; QL222838; Thermo Scientific). Between every labelling step the excess dye, Nb or serum was removed by centrifugation. For cell morphology scoring and cell length measurements, bacteria were randomly selected from samples treated with PBS, $Nbs^{SAI}$ or $Nb^{AF692}$ and analysed with the ImageJ software. The cell lengths of all counted cells (originating from slides from four independent experiments, each containing at least 40 cells) and the ratio of unaffected versus scoured cells were plotted as scatter plots with sample mean and bar graph respectively using the GraphPad software (FIG. 16*b, c*). Cells with collapsed morphology were not counted in the analysis because of the difficulty in visually determining the number of cells included in the collapsed cell masses.

Nbs effect on membrane integrity and cell viability. *B. anthracis* 34F2 cells, grown and harvest as described above, were first treated with labelled $Nbs^{SAI}$, PBS 1× or Triton 10% during 20 min. Excess of treatment was then removed by centrifugation. To monitor the post treatment viability of bacterial cells as a function of membrane integrity, bacilli were stained with Syto9 (green) and propidium iodide (red) as suggested by the manufacturer (LIVE/DEAD™ BacLight™ assay). Excess of DNA staining was then removed by centrifugation and cells were fixed and visualized as described above.

Nbs effect on growth. Cell confluency estimation over time by Incucyte™ Zoom system: Exponential growth phase cells corresponding to $2\times10^3$ CFU, grown and harvested as described above, were incubated with 200 μM $Nbs^{SAI}$ mix and single Nbs, or 1×PBS for the control experiment during 20 and 40 min at RT. Cells were then vortexed and inoculated in fresh BHI with a dilution of 1:10. Static growth in liquid BHI at 37° C. in 96 flat bottom wells plates was recorded every 15 min during 5 h post inoculation.

Cell $OD_{600}$ estimation over time: O/N cultured *B. anthracis* 34F2 (~$2\times10^6$ CFU), grown and harvested as described above, were incubated with indicated concentrations of PBS, $Nbs^{SAI}$ mix or single Nb during 20 min at RT. Cells were then gently vortexed and inoculated in fresh BHI with a 1:5 dilution and cultured at 37° C. with shaking. Prior $OD_{600}$ measurements at indicated points, cells were harvested and vortexed. In case of evaluation of Nbs effect on the growth of an early exponential phase of growth culture, 40 μM $Nbs^{SAI}$, single Nb or the equivalent volume of PBS were added to a *B. anthracis* 34F2 culture at 2 h post inoculum (FIG. 23). Confluency and OD600 results are the mean of three biological replicates.

$Nbs^{SAI}$ Applied as Therapy to Cure Anthrax Infected Mice

Bacteria Preparation:

*B. anthracis* 34F2 cells were grown over night in $RM^+$ media as described elsewhere (Leppla, 1988). Cells were harvest by centrifugation and washed in PBS1× several times to be then suspended in PBS 1×, supplemented or not with 200 μM $Nbs^{SAI}$ or single Nbs, so that 100 μl of suspension would contain ~100,000 CFUs. Bacteria were incubated 45 min at RT prior injection in the mice.

Mice Infection and Nbs Treatment:

7-12 week-old female C57BL/6 mice (purchased from Charles River Laboratories) were injected subcutaneously with 100 μl *B. anthracis* suspension, prepared as described above. Mice received an injection of Nbs treatment or PBS1× (in the case of the mock experiment) after 7, 24, 31, 48, 55, 72, 79, 96 and 120 h post infection (FIG. 17*a, b*, and FIG. 26). In case of the mice group that received a single $Nbs^{SAI}$ dose at the time of infection, animals received their first treatment only (together with the bacterial inoculum; FIG. 26*a*). In case of the post-infection treatment experiment (FIG. 17*b*), (FIG. 12, B) mice receive their first $Nbs^{SAI}$ 15 min after infection rather than as part of the infection inoculum; in this case bacteria were resuspended in PBS as for the mock experiment. Mice condition and survival was monitored twice a day during the experiment and in the first 10 days following the last treatment dose. All animal experiments were performed in accordance with institutional guidelines, following experimental protocol review and approval by the Ghent University Committee on the Use and Care of Animals (Bioethical file number EC2018-009).

Evaluation of Monomeric $Sap^{AD}$, D1, D4, and D6 and Protective Effect Against Anthrax.

Antigens preparation: Monomeric $Sap^{AD}$ was freshly prepared for each immunization using the protein production and purification protocol as described above. Sap single domains (D1, D4 or D6) were prepared as described above, stored in aliquots at −20° C., and thawed prior to each immunization.

Immunization: 16 week-old female C57BL/6 mice (purchased from Janvier Laboratories) (8 mice per group), were injected subcutaneously with 10 μg of antigen (vaccinated group) or PBS 1× (the mock control group), ones weekly over three consecutive weeks. The antigens or the PBS 1× were injected in presence of Complete or Incomplete Freund's Adjuvant (Sigma®), for the first or last two injections, respectively.

Immunoassays for anti-$Sap^{AD}$ IgG detection: Blood samples were collected pre- and one week post immunization. Serum samples were assayed for the presence of IgG antibodies specific to $Sap^{AD}$, D1, D4, and D6 in triplicates by ELISA (FIG. 17*d*). To determine the presence of $Sap^{AD}$ or single domains-specific IgG antibodies in the post-immunised sera, plates were coated with 10 μg antigens respectively (Saps in the case of the PBS 1× group to establish any non-specific binding) in 0.1 M carbonate-bicarbonate buffer, pH 9.6. Serum samples were serially diluted down the plate and the end point titre determined. Bound antibodies were detected using goat anti-mouse IgG antibodies alkaline phosphatase conjugate (AQ3562 Sigma-Aldrich).

Mice infection: *B. anthracis* 34F2 cells were grown over night in RM+ medium and prepared for mice infection as described above. Mice were challenged with 100 μl of bacterial suspension 10 days after the last immunization. Mice survival was monitored twice a day up to 14 days after challenge (FIG. 17*e*). All animal experiments were performed in accordance with institutional guidelines, following experimental protocols review and approval by the Ghent University Committee on the Use and Care of Animals (Bioethical file number EC2017-06)

Aspects of the Disclosure:

A compound binding to the *Bacillus anthracis* Surface Array protein (Sap) which prevents Sap polymerization.

A compound binding to a bacterial S-Layer protein (SLP) which prevents SLP polymerization. A compound, wherein said bacterial S-Layer protein is the *Bacillus anthracis* Surface Array protein (Sap).

Said compound which is a small molecule compound, a peptide, a peptidomimetic, an antibody mimetic, a single-domain antibody or an active antibody fragment. Said compound being a Nanobody.

Said compound of the invention, wherein said compound binds a protein comprising SEQ ID NO:6, SEQ ID NO:7, SEQ ID NO: 9, and/or SEQ ID NO:11.

Said compound of the invention, wherein said compound binds a protein comprising SEQ ID NO:6 and/or SEQ ID NO:7.

Said compound of the invention, wherein the compound binds the epitope of SEQ ID NO:1 comprising the residues 221-222, 271 to 276, residues 316-320, and 328-333.

Said compound of the invention, wherein the compound is a single domain antibody or active antibody fragment comprising the amino acid sequence SGSIFR in CDR1 and the amino acid sequence YDYW in CDR3.

Said compound of the invention, wherein the Nanobody comprises SEQ ID NO: 20, SEQ ID NO: 21, SEQ ID NO: 22, SEQ ID NO: 23, SEQ ID NO: 24, or SEQ ID NO: 25.

Said compound of the invention for use as a medicine.

Said compound of the invention for use to treat *B. anthracis* infection.

Said compound of the invention for use to diagnose a bacterial infection.

Said compound of the invention for use to diagnose *B. anthracis* infection.

Said compound of the invention for use as a tool in structural analysis.

Sequence listing.
> SEQ ID NO: 1: *B. anthracis* Surface-array-protein (Sap) full length amino acid sequence (Uniprot ID: P49051

MAKTNSYKKVIAGTMTAAMVAGVVSPVAAAGKTFPDVPADHWGIDSINYL

VEKGAVKGNDKGMFEPGKELTRAEAATMMAQILNLPIDKDAKPSFADSQG

QWYTPFIAAVEKAGVIKGTGNGFEPNGKIDRVSMASLLVEAYKLDTKVNG

TPATKFKDLETLNWGKEKANILVELGISVGTGDQWEPKKTVTKAEAAQFI

-continued

AKTDKQFGTEAAKVE*SAKAVTTQKVEVKFSKAVEKLTKEDIKVTNKANND*

*KVLVKEVTLSEDKKSATVELYSNLAAKQTYTVDVNKVGKTEVAVG*SLEAK

TIEMADQTVVADEPTALQFTVKDENGTEVVSPEGIEFVTPAAEKINAKGE

ITLAKGTSTTVKAVYKKDGKVVAESKEVKVSAEGAAVASISNWTVAEQNK

ADFTSKDFKQNNKVYEGDNAYVQVELKDQFNAVTTGKVEYESLNTEVAVV

DKATGKVTVLSAGKAPVKVTVKDSKGKELVSKTVEIEAFA*QKAMKEIKLE*

*KTNVALSTKDVTDLKVKAPVLDQYGKEFTAPVTVKVLDKDGKELKEQKLE*

*AKYVNKELVLNAAGQEAGNYTVVLTAKSGEKEAKATLALELKAPG*AFSKF

EVRGLEKELDKYVTEENQKNAMTVSVLPVDANGLVLKGAEAAELKVTTTN

KEGKEVDATDAQVTVQNNSVITVGQGAKAGETYKVTVVLDGKLITTHSFK

VVDTAPTAKGLAVEFTSTSLKEVAPNADLKAALLNILSVDGVPATTAKAT

VSNVEFVSADTNVVAENGTVGAKGATSIYVKNLTVVKDGKEQKVEFDKAV

QVAVSIKEAKPATK

In SEQ ID NO:1, the annotation is as follows: SLH domain (aa 1-215)-Domain 1 (aa 216-295)-Domain 2 (aa 296-384)-Domain 3 (aa 384-490)-Domain 4 (aa 491-595)-Domain 5 (aa 596-706)-Domain 6 (aa 707-814).

The underlined residues are epitopes of Nb684 in D1: TT (aa 221-222) & YSNLAA (aa 271-276), and in D2: ALQFT (aa 316-320); EVVSPE (aa 328-333).

SEQ ID NO:2 BAS0841 *Bacillus anthracis* sterna Sap coding sequence (NC_005945.1; gi|49183039:896643-899087; 2445 nucleotides)

SEQ ID NO:3: *E. coli* codon usage optimized *B. anthracis* sterne Sap coding sequence (2442 nts)

SEQ ID NO:4 Sap amino acid sequence w/o SLH domain (aa 216-814 of SEQ ID NO:1) with C-terminal His6 tag; 606 AA)

SEQ ID NO:5: *E. coli* codon usage optimized *B. anthracis* sterne Sap coding sequence of SAP encoded by SEQ ID NO:4 (1821 nts)

SEQ ID NO:6: Sap Domain 1 amino acid sequence (aa 216-295 of SEQ ID NO:1 incl N-terminal Met; 81 aa)

SEQ ID NO:7: Sap Domain 2 amino acid sequence (aa 296-384 of SEQ ID NO:1 incl Met; 90 aa)

SEQ ID NO:8: Sap Domain 3 amino acid sequence (aa 385-490 of SEQ ID NO:1 incl Met; 108 aa)

SEQ ID NO:9: Sap Domain 4 amino acid sequence (aa 491-595 of SEQ ID NO:1 incl Met; 106 aa)

SEQ ID NO:10: Sap Domain 5 amino acid sequence (aa 596-706 of SEQ ID NO:1 incl Met; 112 aa)

SEQ ID NO:11: Sap Domain 6 amino acid sequence (aa 707-814 of SEQ ID NO:1 incl Met; 109 aa)

SEQ ID NO:12: anti-Sap Nanobody683 amino acid sequence (incl His/EPEA; 129 aa)

SEQ ID NO:13: anti-Sap Nanobody688 amino acid sequence (incl His/EPEA; 130 aa)

SEQ ID NO:14: anti-Sap Nanobody692 amino acid sequence (incl His/EPEA; 128 aa)

SEQ ID NO:15: anti-Sap Nanobody702 amino acid sequence (incl His/EPEA; 129 aa)

SEQ ID NO:16: anti-Sap Nanobody704 amino acid sequence (incl His/EPEA; 131 aa)

SEQ ID NO:17: anti-Sap Nanobody707 amino acid sequence (incl His/EPEA; 129 aa)

SEQ ID NO:18: anti-Sap Nanobody684 amino acid sequence (incl His/EPEA; 129 aa)

SEQ ID NO:19: anti-Sap Nanobody694 amino acid sequence (incl His/EPEA; 134 aa)

SEQ ID NO:20: anti-Sap Nanobody683 amino acid sequence (119 aa)

SEQ ID NO:21: anti-Sap Nanobody688 amino acid sequence (120 aa)

SEQ ID NO:22 anti-Sap Nanobody692 amino acid sequence (118 aa)

SEQ ID NO:23: anti-Sap Nanobody702 amino acid sequence (119 aa)

SEQ ID NO:24: anti-Sap Nanobody704 amino acid sequence (121 aa)

SEQ ID NO:25: anti-Sap Nanobody707 amino acid sequence (119 aa)

SEQ ID NO:26: Sap Domain 4' amino acid sequence (aa 491-595 of domain 4 incl Met, plus N-terminal part of Domain 5; 136 aa)

SEQ ID NO:27*: B. anthracis* S-Layer protein EA1 full length amino acid sequence (Uniprot ID: P94217; 862AA)

SEQ ID NO:28: EA1 amino acid sequence w/o SLH domain (aa 214-862 of SEQ ID NO:27) with N-terminal His6 tag (665AA)

SEQ ID NO:29: *E. coli* codon usage optimized *B. anthracissterne* EA1 coding sequence of EA1 encoded by SEQ ID NO:28 (1985 nts)

SEQ ID NO: 30-35: Primer sequences for $Sap^{AD}D1^{AFfw}$, $Sap^{AD}D1^{AFrv}$, $Sap^{AD}D4^{AFfw}$, $Sap^{AD}D4^{AFrv}$, $Sap^{AD}D6^{AFfw}$, $Sap^{AD}D6^{AFrv}$.

SEQ ID NO: 36: anti-Sap Nanobody679 amino acid sequence (incl His/EPEA; 129 aa)

SEQ ID NO: 37: anti-Sap Nanobody687 amino acid sequence (incl His/EPEA; 129 aa)

SEQ ID NO: 38: anti-Sap Nanobody695 amino acid sequence (incl His/EPEA; 133 aa)

SEQ ID NO: 39: anti-Sap Nanobody703 amino acid sequence (incl His/EPEA; 135 aa)

SEQ ID NO: 40: non-Sap binding control Nanobody11 amino acid sequence (incl His/EPEA; 137 aa).

REFERENCES

Abrahams, J. P. & Leslie, A. G. W. Methods used in the structure determination of bovine mitochondrial F1 ATPase. Acta Crystallographica Section D 52, 30-42, (1996).

Baranova et al. 2012. SbsB structure and lattice reconstruction unveil Ca2+ triggered S-Layer assembly. Nature. 487(7405):119-22.

Barbas, et al. 1994. In vitro evolution of a neutralizing human antibody to human immunodeficiency virus type 1 to enhance affinity and broaden strain cross-reactivity. Proc Natl Acad Sci USA. 91(9):3809-13.

Bharat, T. A. M. et al. Structure of the hexagonal surface layer on *Caulobacter crescentus* cells. Nature microbiology 2, 17059, (2017).

Bricogne, G., Vonrhein, C., Flensburg, C., Schiltz, M. & Paciorek, W. Generation, representation and flow of phase information in structure determination: recent developments in and around SHARP 2.0. Acta crystallographica. Section D, Biological crystallography 59, 2023-2030 (2003).

Candela, T. & Fouet, A. *Bacillus anthracis* CapD, belonging to the gamma-glutamyltranspeptidase family, is required for the covalent anchoring of capsule to peptidoglycan. Molecular microbiology 57, 717-726, (2005).

Collaborative Computational Project, Number 4. The CCP4 suite: programs for protein crystallography. Acta crystallographica. Section D, Biological crystallography 50, 760-763, (1994).

Collier, R. J. & Young, J. A. Anthrax toxin. Annual review of cell and developmental biology 19, 45-70, (2003).

Conrath K E, et al. 2001. Beta-lactamase inhibitors derived from single-domain antibody fragments elicited in the camelidae. Antimicrobial agents and chemotherapy. 45: 2807-2812.

Coppens F, et al. 2015. Structural and adhesive properties of the long polar fimbriae protein LpfD from adherent-invasive *Escherichia coli*. Acta Crystallogr D Biol Crystallogr. 71(Pt 8):1615-26.

Couture-Tosi et al. 2002. J. Bacteriol. 184, 6448-6456. Sára M, Sleytr U B. 2000. S-Layer proteins. J Bacteriol. 182(4):859-68.

Cowtan, K. D. & Main, P. Phase combination and cross validation in iterated density-modification calculations. Acta Crystallographica Section D 52, 43-48, (1996).

Domanska K, et al. 2011. Atomic structure of a Nanobody-trapped domain-swapped dimer of an amyloidogenic beta2-microglobulin variant. Proc Natl Acad Sci USA. 108: 1314-1319.

Etienne-Toumelin I, et al. 1995. Characterization of the *Bacillus anthracis* S-Layer: cloning and sequencing of the structural gene. J Bacteriol. 177(3):614-20.

Gerbino E, et al. 2015. Role of S-Layer proteins in bacteria. World J Microbiol Biotechnol. 31(12):1877-87.

Hawkins et al. 1992. Selection of phage antibodies by binding affinity. Mimicking affinity maturation. J. Mol Biol. (3):889-96.

Holm, L. & Sander, C. Dali: a network tool for protein structure comparison. Trends in biochemical sciences 20, 478-480 (1995).

Jackson et al. 1995. J. Immunol. 154: 3310-9.

Jernigan, D. B. et al. Investigation of bioterrorism-related anthrax, United States, 2001: epidemiologic findings. Emerging infectious diseases 8, 1019-1028, (2002).

Johnson and Hawkins (Affinity maturation of antibodies using phage display, Oxford University Press, 1996).

Kandalaft et al. (2015). Targeting surface-layer proteins with single-domain antibodies: a potential therapeutic approach against *Clostridium difficile*-associated disease. Appl. Microbiol. Biotechn. 99: 8549-8562.

Kern et al. 2011. Structure of Surface Layer Homology (SLH) Domains from *Bacillus anthracis* Surface Array Protein. J. Biol. Chem. 286: 26042-26049.

Kern V J, et al. 2012. Surface-layer (S-Layer) proteins sap and EA1 govern the binding of the S-Layer-associated protein BslO at the cell septa of *Bacillus anthracis*. J Bacteriol. 194(15):3833-40.

Kirk, J. A. et al. New class of precision antimicrobials redefines role of *Clostridium difficile* S-Layer in virulence and viability. Science translational medicine 9, (2017).

Kozin, M. B. & Svergun, D. I. Automated matching of high- and low-resolution structural models. Journal of Applied Crystallography 34, 33-41, (2001).

Leppla, S. H. Production and purification of anthrax toxin. Methods in enzymology 165, 103-116 (1988)

Makino S I, et al. 1989. Molecular characterization and protein analysis of the cap region, which is essential for encapsulation in *Bacillus anthracis*. J Bacteriol 171:722-730.

Marks et al. 1992. Biotechnology 10:779-783, 1992

Mesnage S, et al. 1997. Molecular characterization of the *Bacillus anthracis* main S-Layer component: evidence that it is the major cell-associated antigen. Mol Microbiol. 23(6):1147-55.

Mignot T, et al. 2002. Developmental switch of S-Layer protein synthesis in *Bacillus anthracis*. Mol. Microbiol. 43(6):1615-27.

Mignot T, et al. 2003. A plasmid-encoded regulator couples the synthesis of toxins and surface structures in *Bacillus anthracis*. Mol Microbiol. 47(4):917-27.

Moonens K., et al. 2016. Structural Insights into Polymorphic ABO Glycan Binding by Helicobacter pylori. Cell Host Microbe. 19(1):55-66.

Murshudov, G. N., Vagin, A. A. & Dodson, E. J. Refinement of macromolecular structures by the maximum-likelihood method. Acta crystallographica. Section D, Biological crystallography 53, 240-255, (1997).

Nema, S. et al. 1997. Excipients and Their Use in Injectable Products" PDA Journal of Pharmaceutical Science & Technolog, 51 (4), 166-171.

Pardon E, et al. 2014. A general protocol for the generation of Nanobodies for structural biology. Nat Protoc. 9(3): 674-93.

Petoukhov, M. V. et al. New developments in the ATSAS program package for small-angle scattering data analysis. J Appl Crystallogr 45, 342-350, (2012).

Powell, M. F. et al. 1998. "Compendium of Excipients for Parenteral Formulations" PDA Journal of Pharmaceutical Science & Technology, 52(5), 238-311).

Preisz H (1909) Experimentelle Studien über Virulenz, Empfänglichkeit and Innnnunität beim Milzbrand. Zeitschr Innnnunitätsf 5:341-452.

Sára, M., & Sleytr, U. B. (2000). S-Layer Proteins. Journal of Bacteriology, 182(4), 859-868.

Sharma et al., 2016. Ultrasensitive electrochemical immunoassay for surface array protein, a *Bacillus anthracis* biomarker using Au—Pd nanocrystals loaded on boron-nitride nanosheets as catalytic labels. Biosens Bioelectron. 80:442-449.

Sheldrick, G. M. Experimental phasing with SHELXC/D/E: combining chain tracing with density modification. Acta crystallographica. Section D, Biological crystallography 66, 479-485, (2010).

Shier et al. 1995. Gene 169: 147-155.

Strickley, R. G 1999. Parenteral Formulations of Small Molecule Therapeutics Marketed in the United States (1999)-Part-1" PDA Journal of Pharmaceutical Science & Technology, 53(6), 324-349.

Svergun, D. Determination of the regularization parameter in indirect-transform methods using perceptual criteria. Journal of Applied Crystallography 25, 495-503, (1992).

Svergun, D., Barberato, C. & Koch, M. H. J. CRYSOL—a Program to Evaluate X-ray Solution Scattering of Biological Macromolecules from Atomic Coordinates. Journal of Applied Crystallography 28, 768-773, (1995).

Sweeney, D. A., Hicks, C. W., Cui, X., Li, Y. & Eichacker, P. Q. Anthrax infection. American journal of respiratory and critical care medicine 184, 1333-1341, (2011).

Sychantha, D. et al. Molecular Basis for the Attachment of S-Layer Proteins to the Cell Wall of *Bacillus anthracis*. Biochemistry 57, 1949-1953, (2018).

Wang, X. Y. et al. A S-Layer Protein of *Bacillus anthracis* as a Building Block for Functional Protein Arrays by In Vitro Self-Assembly. Small (Weinheim an der Bergstrasse, Germany) 11, 5826-5832, (2015)

Weiner, Z. P. & Glomski, I. J. Updating perspectives on the initiation of *Bacillus anthracis* growth and dissemination through its host. Infection and immunity 80, 1626-1633, (2012).

Yelton et al., 1995. Affinity maturation of the BR96 anti-carcinoma antibody by codon-based mutagenesis. J Immunol. 1995 Aug. 15; 155(4):1994-2004.

Zhang et al., 2008. Plasmid-based vaccination with candidate anthrax vaccine antigens induces durable type 1 and type 2 T-helper immune responses. Vaccine. 26: 614-622.

Zwartouw H T, Smith H (1956) Polyglutamic acid from *Bacillus anthracis* grown in vivo: structure and aggressin activity. Biochem J 63:437-454.

The invention claimed is:

1. A molecule that specifically binds to a bacterial Surface-layer protein (SLP), wherein the binding of the molecule disintegrates the bacterial surface layer (S-Layer), wherein the molecule is a small molecule, a peptide, a peptidomimetic, an antibody mimetic, an immunoglobulin single variable domain, or an active antibody fragment.

2. The molecule of claim 1, wherein the bacterial S-Layer is the S-Layer of a pathogen selected from the group consisting of *Bacillus* species, *B. anthracis, B. cereus, B. thuringiensis, Clostridium difficile, Paenibacillus larvae, Caphylobacteri fetus, Campylobacter rectus, Tannerella forsythia, Aeromonas hydrophila, Rickettsia prowazekii, Rickettsia rickettsia, Rickettsia typhi, Serratia marcescens, Aeromonas salmonicida*, and *Lactobacillus acidophilus*.

3. The molecule of claim 1, wherein the molecule is a Nanobody.

4. The molecule of claim 1, wherein the bacterial S-Layer protein is the *Bacillus anthracis* Surface Array protein (Sap).

5. The molecule of claim 4, wherein the molecule binds a protein domain comprising at least one of SEQ ID NO:6, SEQ ID NO:7, SEQ ID NO: 9, and SEQ ID NO:11.

6. The molecule of claim 5, wherein the protein domain comprises SEQ ID NO:6 and SEQ ID NO:7.

7. The molecule of claim 5, wherein the molecule binds the epitope of SEQ ID NO:1 comprising the residues 221-222, 271 to 276, residues 316-320, and 328-333.

8. The molecule of claim 1, wherein the molecule is an immunoglobulin single variable domain or active antibody fragment comprising the amino acid sequence SGSIFR in CDR1 and the amino acid sequence YDYW in CDR3.

9. The molecule of claim 3, wherein the Nanobody comprises SEQ ID NO: 20, SEQ ID NO: 21, SEQ ID NO: 22, SEQ ID NO: 23, SEQ ID NO: 24, or SEQ ID NO: 25, or a humanized variant thereof.

10. A composition comprising at least one molecule of claim 1 and a pharmaceutically acceptable carrier.

11. A method of treating a subject suffering from *B. anthracis* infection; the method comprising:

treating the subject with the composition of claim 1, so as to treat *B. anthracis* infection in the subject.

* * * * *